US009868953B2

(12) United States Patent
Squiers et al.

(10) Patent No.: US 9,868,953 B2
(45) Date of Patent: Jan. 16, 2018

(54) METHODS AND COMPOSITIONS FOR PREVENTING ISCHEMIA REPERFUSION INJURY IN ORGANS

(71) Applicant: Quark Pharmaceuticals, Inc., Fremont, CA (US)

(72) Inventors: Elizabeth C. Squiers, Half Moon Bay, CA (US); Shai Erlich, Concord, CA (US); Daniel Rothenstein, Ramat Hasharon (IL); Nir Sharon, Jerusalem (IL); Daniel J. Odenheimer, Potomac, MD (US); Elena Feinstein, Rehovot (IL)

(73) Assignee: Quark Pharmaceuticals, Inc., Fremont, CA (US)

( * ) Notice: Subject to any disclaimer, the term of this patent is extended or adjusted under 35 U.S.C. 154(b) by 0 days.

(21) Appl. No.: 15/650,297

(22) Filed: Jul. 14, 2017

(65) Prior Publication Data
US 2017/0335327 A1 Nov. 23, 2017

Related U.S. Application Data

(63) Continuation of application No. 15/312,425, filed as application No. PCT/US2015/032499 on May 27, 2015, now abandoned.

(60) Provisional application No. 62/004,239, filed on May 29, 2014.

(51) Int. Cl.
| | | |
|---|---|---|
| C12N 15/11 | (2006.01) | |
| C12N 15/113 | (2010.01) | |
| A61K 31/713 | (2006.01) | |
| A61K 45/06 | (2006.01) | |
| A61K 9/00 | (2006.01) | |

(52) U.S. Cl.
CPC ........ *C12N 15/1135* (2013.01); *A61K 9/0019* (2013.01); *A61K 31/713* (2013.01); *A61K 45/06* (2013.01); *C12N 2310/14* (2013.01); *C12N 2310/317* (2013.01); *C12N 2310/319* (2013.01); *C12N 2310/321* (2013.01); *C12N 2310/3515* (2013.01); *C12N 2320/30* (2013.01)

(58) Field of Classification Search
None
See application file for complete search history.

(56) References Cited

U.S. PATENT DOCUMENTS

| 6,593,353 B1 | 7/2003 | Gudkov et al. |
|---|---|---|
| 6,982,277 B2 | 1/2006 | Gudkov et al. |
| 7,008,956 B2 | 3/2006 | Gudkov et al. |
| 7,012,087 B2 | 3/2006 | Gudkov et al. |
| 7,910,566 B2 | 3/2011 | Feinstein |
| 8,148,342 B2 | 4/2012 | Feinstein et al. |
| 2006/0069056 A1 | 3/2006 | Feinstein et al. |
| 2009/0105173 A1 | 4/2009 | Feinstein |
| 2010/0222409 A1 | 9/2010 | Kalinski et al. |

FOREIGN PATENT DOCUMENTS

| EP | 2 170403 | 4/2014 |
|---|---|---|
| WO | WO 2010/144336 | 12/2010 |
| WO | WO 2014/043292 | 3/2014 |

OTHER PUBLICATIONS

International Search Report and Written Opinion for PCT/US2015/032499, dated Aug. 13, 2015, 15 pages.
Molitoris et al., "siRNA Targeted to p53 Attenuates Ischemic and Cisplatin-Induced Acute Kidney Injury," J. Am. Soc. Nephrol., vol. 20:1754-1764, 2009.
Kelly et al., "P53 mediated the apoptotic response to GTP depletion after renal ischemia-reperfusion: Protective role of a p53 inhibitor," J. Am. Soc. Nephrol., vol. 14:128-138, 2003.
Dagher et al. "The p53 inhibitor pifithrin—can stimulate fibrosis in a rat model of ischemic acute kidney injury," Am. J. Physiol. Renal. Physiol., vol. 302:F284-F291, 2012.
Fujino et al., "Silencing of p53 RNA through transarterial delivery ameliorates renal tubular injury and downregulates GSK-3 expression after ischemia-reperfusion injury," Am. J. Physiol., vol. 305:F1617-F1627, 2013.
Powell et al., Managing renal transplant ischemia reperfusion injury: novel therapies in the pipeline, Clinical Transplantation, vol. 27(4): 484-491, 2013.
Thompson et al., Toxicological and Pharmacokinetic Properties of Chemically Modified siRNAs Targeting p53 RNA Following Intravenous Administration, Nucleic Acid Therapeutics, vol. 22(4):255-264, 2012.

*Primary Examiner* — Ekaterina Poliakova-Georgantas
(74) *Attorney, Agent, or Firm* — Fish & Richardson P.C.

(57) ABSTRACT

The invention, in some embodiments, relates to compounds and methods for the prevention of ischemia reperfusion injury (IRI) in organs, and in particular to IRI in organs aged 35 years and older. Specific uses include prevention of IRI in native organs in vivo, in reimplantations and in transplantations of donor organs aged 35 years and older. Additional embodiments include the prophylaxis of delayed graft function (DGF) and reduction in the frequency, amount and duration of dialysis in recipients of deceased donor kidney transplantations. The methods entail contacting the organ in vivo or ex vivo with a temporary p53 inhibitor. Novel temporary dsNA p53 inhibitors are further provided.

27 Claims, 4 Drawing Sheets

METHODS AND COMPOSITIONS FOR PREVENTING ISCHEMIA REPERFUSION INJURY IN ORGANS

SEQUENCE LISTING

This application incorporates-by-reference nucleotide and/or amino acid sequences which are present in the file named "262-PCT1_ST25.txt", which is 29 Kbytes in size, and which was created on May 27, 2015 in the IBM-PC machine format, having an operating system compatibility with MS-Windows, and is submitted herewith.

FIELD OF THE INVENTION

The invention, in some embodiments, relates to methods for the prevention of ischemia reperfusion injury (IRI) in organs, and in particular to IRI in organs aged 35 years and older. Specific uses include prevention of IRI in native organs in vivo, in reimplantations and in transplantations of donor organs aged 35 years and older. Additional embodiments include the prophylaxis of delayed graft function (DGF) and reduction in the frequency, amount and duration of dialysis in recipients of deceased donor kidney transplantations. The methods entail contacting the organ in vivo or ex vivo with a temporary p53 inhibitor. Novel temporary dsRNA p53 inhibitors are further provided.

BACKGROUND OF THE INVENTION

Ischemic Reperfusion Injury

Ischemic Reperfusion Injury (IRI) is cellular damage caused to a tissue or organ when blood supply returns to the tissue after a period of ischemia. The absence of blood oxygen and nutrients during the ischemic period creates a condition in which the restoration of circulation results in oxidative damage, including cellular dysfunction, apoptosis and necrosis.

IRI can occur in any body tissue as a result of inter alia surgery, wounds, trauma, obstructions, implantations and transplantations.

Delayed Graft Function

Delayed graft function (DGF) is an important risk factor in adversely affecting the outcome of organ transplants, including renal transplant such as deceased donor renal transplant (DDRT), particularly in a recipient of a kidney from an Expanded Criteria Donor (ECD) or from a Standard Criteria Donor (SCD) with prolonged cold ischemia time.

Analysis of over 138,000 cases in the UNOS Renal Transplant Registry database, revealed that long-term graft survival (>10 years) has remained unchanged despite improvements in short term acute rejection rates (Takada M, et al.; Transplantation. 1997 Dec. 15; 64(11):1520-5.). One of the major contributing factors to poorer long-term outcomes including poor graft survival identified in this retrospective review was DGF. DGF is defined by UNOS as the need for dialysis within the first seven days after transplantation. The etiology of DGF is not well understood but is undoubtedly multifactorial, in which IRI to the graft that directly results from the transplantation plays a central role. IRI is an antigen-independent process that is a major risk factor for development of chronic allograft dysfunction as demonstrated in animal models (Goes N, et al., Transplantation. 1995 27; 59(4):565-72; Kusaka M, et al., Transplantation. 1999 67(9):1255-61; Takada M, et al; Transplantation. 1997 64(11):1520-5). Ischemic conditions caused by reduced local blood flow to the kidneys during cold storage prior to transplantation followed by oxidative stress after the restoration of blood supply after the transplantation initiates a chain of events that can lead to acute tubular injury. Renal tubular cell dysfunction and apoptotic cell death are the hallmarks of this process (Oberbauer R, et al. J Am Soc Nephrol. 1999 10(9):2006-13; Giral-Classe M, et al. Kidney Int. 1998 54(3):972-8).

Due to the growing disparity between the numbers of candidates awaiting transplantation and available donor organs, the use of kidneys from Expanded Criteria Donors (ECD) has been increasing (Organ Procurement and Transplantation Network (OPTN), Scientific Registry of Transplant Recipients (SRTR). 2008 OPTN/SRTR Annual Report: Transplant Data 1998-2007 [Internet]. Richmond (Va.): Health Resources and Services Administration's Division of Transplantation (HRSA)/U.S. Department of Health & Human Services; 2009 Oct. 7 [cited 2010 April]).

U.S. Pat. Nos. 6,593,353; 6,982,277; 7,008,956 and 7,012,087 relate to the temporary inhibition of p53 for the treatment of cancer and other diseases and disorders.

U.S. Patent Application Publication No. 2006/0069056 to the assignee of the present application, is directed to short interfering p53 molecules and methods of use.

U.S. Pat. Nos. 7,910,566 and 8,148,342 to the assignee of the present application, relate to methods for treating acute kidney injury (AKI) and acute renal failure (ARF), respectively, with short interfering p53 molecules.

WO 2010/144336 to the assignee of the present application is directed to a method of treating a subject with chronic kidney disease (CKD) resulting from exposure to a recurring renal insult with a p53 inhibitor.

U.S. Patent Application Publication No. US 2010/0222409 and EP Patent No EP 2170403 to the assignee of the present application relate to a method of reducing Delayed Graft Function (DGF) in a recipient of a kidney transplant from a deceased donor using a double-stranded RNA compound for down-regulating the expression of a p53 gene.

PCT Patent Application No. PCT/US2013/059349, to the assignee of the present application, provides modified double-stranded nucleic acid compounds for down-regulating the expression of a p53 gene.

There remains an unmet need for a method of prevention or attenuation of ischemic reperfusion injury in native and donor organs.

SUMMARY OF THE INVENTION

The present disclosure is based in part on the surprising and clinically significant finding that recipients of deceased donor kidneys aged 35 years or older, wherein the recipients are treated with a temporary p53 inhibitor show a greater improvement in clinical outcome compared to recipients of younger deceased donor kidneys and untreated patients. The present inventors have further surprisingly found that temporary inhibitors of the p53 gene are more effective in providing prophylaxis of DGF in a kidney over the age of about 30 (for example, over the age of about 35, or over the age of about 40, 45 or 50) and including kidneys from both Expanded Criteria Donors (ECD) and Standard Criteria Donors (SCD). Additionally, the treatment of recipients of deceased donor kidneys with a temporary p53 inhibitor results in the reduction in the amount and duration of dialysis post-transplantation compared to untreated recipients.

Aspects and embodiments of the invention are described in the specification herein below and in the appended claims.

According to a first aspect, there is provided herein a method of prophylaxis of ischemic reperfusion injury (IRI) of an organ, comprising contacting the organ with a temporary p53 gene inhibitor in an amount effective to provide prophylaxis of IRI in the organ; wherein the organ is aged 35 or over. Further provided is a temporary inhibitor of a p53 gene for use in prophylaxis of ischemic reperfusion injury (IRI), wherein the inhibitor is for contacting an organ that is 35 years or older at risk of IRI and use of a temporary inhibitor of a p53 gene for the manufacture of a medicament for providing prophylaxis of ischemic reperfusion injury (IRI), wherein the inhibitor is for contacting an organ that is 35 years or older at risk of IRI. In some embodiments of the method, inhibitor or use wherein the organ is at risk of IRI, the organ is an organ native to a subject, a reimplanted organ or a transplanted organ.

In some embodiments of the method, inhibitor or use the risk of IRI in the native organ is imposed by temporary cessation of blood flow to the organ or by temporary global hypoxia of the organ. The temporary cessation of blood flow is due to, for example, at least one of thrombosis, vasoconstriction, pressure on blood vessels or removal of the organ from the body of a subject with subsequent reimplantation.

The invention, in some embodiments, relates to an organ over the age of about 30 or 34; or an organ over the age of about 35; or an organ over the age of about 36; or an organ over the age of about 37; or an organ over the age of about 38; or an organ over the age of about 39; or an organ over the age of about 40; or an organ over the age of about 41; or an organ over the age of about 42; or an organ over the age of about 43; or an organ over the age of about 44; or an organ over the age of about 44; or an organ over the age of about 46; or an organ over the age of about 47; or an organ over the age of about 48; or an organ over the age of about 49; or an organ over the age of about 50; or a donor organ over the age of about 30 or 34; or a donor organ over the age of about 35; or a donor organ over the age of about 36; or a donor organ over the age of about 37; or a donor organ over the age of about 38; or a donor organ over the age of about 39; or a donor organ over the age of about 40; or a donor organ over the age of about 41; or a donor organ over the age of about 42; or a donor organ over the age of about 43; or a donor organ over the age of about 44; or a donor organ over the age of about 44; or a donor organ over the age of about 46; or a donor organ over the age of about 47; or a donor organ over the age of about 48; or a donor organ over the age of about 49; or a donor organ over the age of about 50; or a deceased Expanded Criteria Donor (ECD). Furthermore, the method includes organs that have been preserved entirely by cold storage following removal from the donor and prior to transplantation.

In some embodiments of the method, inhibitor or use the transplant organ originates from a deceased donor. In various embodiments, the contacting the organ with the temporary inhibitor comprises administering the temporary inhibitor to a subject possessing the organ at risk of IRI. The organ at risk may be a native organ of a subject and has never been removed from the body of the subject. Alternatively, the organ at risk has been reimplanted to a subject or transplanted to a subject.

In some embodiments of the method, inhibitor or use the contacting the organ with the temporary inhibitor comprises contacting the organ with the temporary inhibitor ex vivo prior to transplantation or reimplantation of the organ to a recipient.

In some embodiments of the method, inhibitor or use the organ at risk of IRI is 45 years old or older.

In some embodiments of the method, inhibitor, or use prophylaxis of IRI results in prophylaxis of IRI-associated organ dysfunction or in prophylaxis of IRI-associated delayed graft function.

In some embodiments of the method, inhibitor, or use the organ is selected from the group consisting of a kidney, a liver, a pancreas, a heart, a lung, an intestine, skin, a blood vessel, a brain, a retina, composite tissue, a blood vessel, an ear, a limb; or a part thereof. In some embodiments the organ is a lung, heart or kidney, preferably a kidney.

In various embodiments of the method, inhibitor, or use the organ is a kidney graft and wherein prophylaxis of IRI results in prophylaxis of delayed graft function (DGF). The prophylaxis of DGF results in the reduction of the amount, intensity and duration of dialytic support during at least the first 7 days post-transplant in a dialysis-dependent end stage renal disease (ESRD) patient undergoing deceased donor renal transplantation. In some embodiments, the prophylaxis of DGF results in at least one of a longer time interval between transplantation and the first dialysis treatment post-transplant, a shorter mean duration of initial post-transplantation course of dialysis and a higher measured glomerular filtration rate (mGFR) at the end of the first post-transplant month.

In some embodiments of the method, inhibitor or use, the prophylaxis of IRI results in the reduction of the amount, intensity and/or duration of dialytic support during the first 30 days, first 60 days, first 120 days and up to the first 180 days post-transplant in a dialysis-dependent end stage renal disease (ESRD) patient undergoing deceased donor renal transplantation.

In various embodiments of the method, inhibitor or use the organ, for example a kidney, is preserved entirely by cold storage following removal from the donor and prior to implantation in the recipient.

In various embodiments of the method, inhibitor or use the organ, for example a kidney is preserved by machine-perfusion for at least a portion of time following removal from the donor and prior to implantation in the recipient.

In some embodiments of the method, inhibitor or use of prophylaxis of IRI in a donor kidney, the method further comprises the steps of (a) selecting a recipient having a kidney from a deceased Expanded Criteria Donor, and (b) administering to the recipient a temporary inhibitor of a p53 gene in an amount effective to provide prophylaxis of DGF in the recipient. In some embodiments, the kidney is from a donor that is not a deceased Expanded Criteria Donor. In alternative embodiments, the kidney is from a donor that is between the ages of 50 and 59 (inclusive) who does not have at least two of the following: a history of high blood pressure, terminal serum creatinine level greater than 1.5 mg/dl, or cardiovascular cause of brain death. In some embodiments, the kidney is from a donor that is not over the age of 60.

In further embodiment of the method, inhibitor or use the prophylaxis of IRI provides prophylaxis of acute kidney injury (AKI), whereby the AKI results from at least one of cardiovascular surgery, cardiopulmonary surgery, renal surgery, acute ureteral obstruction, shock, global hypoxia and/or exposure to a nephrotoxin.

In a second aspect, provided herein is a method of prophylaxis of ischemic reperfusion injury (IRI) in a donor kidney from a deceased donor, comprising contacting the kidney with a temporary inhibitor of p53 in an amount effective to provide prophylaxis of IRI in the kidney. Further provided is a temporary inhibitor of p53 for use in prophylaxis of ischemic reperfusion injury (IRI) in a donor kidney from a deceased donor, wherein the inhibitor is for contacting the kidney. Further provided is use of a temporary inhibitor of a p53 gene for the manufacture of a medicament for providing prophylaxis of ischemic reperfusion injury (IRI) in donor kidney from a deceased donor, wherein the inhibitor is for contacting the kidney.

In some embodiments of the method, inhibitor or use the prophylaxis of IRI results in the reduction of the amount, intensity and duration of dialytic support during the first 180 days post-transplant in a dialysis-dependent end stage renal disease (ESRD) patient undergoing deceased donor renal transplantation.

In some embodiments of the methods, inhibitors or uses disclosed hereinabove, the temporary inhibitor of a p53 gene is selected from the group consisting of a small organic molecule, a protein, an antibody or fragment thereof, a peptide, a polypeptide, a peptidomimetic and a nucleic acid molecule; or a pharmaceutically acceptable salt or prodrug thereof. The temporary inhibitor of a p53 gene may be a nucleic acid molecule selected from the group consisting of a single stranded antisense nucleic acid (ssNA), a double-stranded NA (dsNA), a small interfering NA (siNA), a short hairpin NA (shNA), a micro RNA (miRNA), an aptamer, and a ribozyme, or a pharmaceutically acceptable salt or prodrug thereof. The nucleic acid molecule may be modified or chemically modified. In some embodiments of the method, inhibitor or use, the nucleic acid molecule is a ssNA or a dsNA, comprising one or more of a modified nucleotide, an unmodified nucleotide, a nucleotide analogue and an unconventional moiety.

In some preferred embodiments of the method, inhibitor or use, the dsNA selected from the group consisting of an unmodified dsNA or a chemically modified dsNA; or a salt or prodrug thereof. In some embodiments, the dsNA comprises an antisense strand having a nucleic acid sequence set forth in Table 2 (SEQ ID NOS:21-33, 35, 37). In various embodiments, the dsNA comprises an antisense strand sequence 5' UGAAGGGUGAAAUAUUCUC 3' and a sense strand sequence 5' GAGAAUAUUUCACCCUUCA 3'.

In some specific embodiments of the method, inhibitor or use, the dsNA molecule is a synthetic small interfering ribonucleic acid (siRNA) having the structure:

```
                                        (SEQ ID NO: 37)
5' UGAAGGGUGAAAUAUUCUC 3' (antisense strand)

(SEQ ID NO: 36)
3' ACUUCCCACUUUAUAAGAG 5' (sense strand)
``` wherein each of A, C, U and G is a ribonucleotide and each consecutive ribonucleotide is joined to the next ribonucleotide by a covalent bond; and wherein alternating ribonucleotides in both the antisense strand and the sense strand are 2'-O-methyl sugar modified ribonucleotides and a 2'-O-methyl sugar modified ribonucleotide is present at both the 5' terminus and the 3' terminus of the antisense strand and an unmodified ribonucleotide is present at both the 5' terminus and the 3' terminus of the sense strand. The dsNA may be terminally phosphorylated or non-phosphorylated at one or more of the 5' termini and or 3' termini. In some embodiments, the dsNA is non-phosphorylated at the 5' termini and at the 3' termini. The dsNA molecule is preferably in the form of a pharmaceutically acceptable salt, for example a sodium salt.

In various embodiments of the method, inhibitor or use disclosed hereinabove, the prophylaxis of IR injury provides prophylaxis of wherein the temporary inhibitor of a p53 gene is administered at a dose of about 1.0 mg/kg to about 50 mg/kg, preferable about 10 mg/kg.

In some embodiments of the method, inhibitor or use, the temporary inhibitor of a p53 gene is formulated as a composition. In some embodiments the temporary inhibitor may be administered as a liquid composition comprising a pharmaceutically acceptable carrier.

In some embodiments of the method, inhibitor or use, the composition further comprises a cell targeting moiety. The cell targeting moiety may be covalently or non-covalently attached to the temporary inhibitor of a p53 gene.

In some embodiments of the method, inhibitor or use, the temporary inhibitor is administered to the recipient as an injectable composition comprising a pharmacologically acceptable aqueous excipient. The temporary inhibitor may be administered by intravenous (IV) injection. The intravenous (IV) injection is administered in a single treatment, which may be a single dose or multiple dose. In some embodiments of the method, inhibitor or use, the single treatment is a single dose or multiple doses, preferably a single dose. The single treatment is for example, a single intravenous push (IVP).

In some embodiments of the method, inhibitor or use, the intravenous (IV) injection is administered intraoperatively following autograft/reimplantation or allograft/transplantation reperfusion. The intravenous (IV) injection is administered directly into a proximal port of a central venous line or through a peripheral line.

Administration mode and dose of the temporary inhibitor is determined by the attending physician or hospital staff and will be decided according to various factors including the organ, the indication, the overall health and age of the subject. In some embodiments, the temporary inhibitor is administered systemically, subcutaneously, topically, by inhalation, by instillation (lungs). Depending on the target organ, the temporary inhibitor may be conjugated or formulated, for example, in liposomes, lipoplex, microparticles or nanoparticles.

In some embodiments of the method, inhibitor or use, wherein the recipient received an organ form a donor, the recipient is further administered a medication selected from the group consisting of an antiviral agent, an antifungal agent, an antimicrobial agent, an immunosuppressant agent, and any combination thereof. In some embodiments, the medication is an immunosuppressant agent that is a calcineurin inhibitor. In various embodiments, the immunosuppressant agent is selected from the group consisting of tacrolimus (TAC), mycophenolate mofetil (MMF), mycophenolic acid (MPA), a corticosteroid, a cyclosporine, an azathioprine, a sirolimus, and any combination thereof. In some embodiments, the immunosuppressant agent is tacrolimus (TAC). The recipient may further be administered an antibody induction therapy agent, for example peri-operatively and prior to transplant reperfusion. In various embodiments, the antibody induction therapy agent comprises a polyclonal anti-thymocyte globulin (ATG) or an anti-CD25 (anti-IL-2R) monoclonal antibody.

In some embodiments of the method, inhibitor or use, the inhibitor is present in a kit comprising the inhibitor and instructions for use. For example, the inhibitor is present within a container in liquid or solid form. The kit may further include a diluent and/or a means for administration, for example a syringe.

According to an aspect of some embodiments of the invention, there is provided an inhibitor of a p53 gene for use in prophylaxis of Delayed Graft Function in a recipient of a kidney transplant, wherein the recipient has received the kidney from a donor having a Kidney Donor Risk Index (KDRI) of at least 1.25. According to an aspect of some embodiments of the invention, there is provided the use of an inhibitor of a p53 gene for the manufacture of a medicament for providing prophylaxis of DGF in a recipient of a kidney transplant, wherein the recipient has received the kidney from a donor having a Kidney Donor Risk Index (KDRI) of at least 1.25.

In some embodiments of the method, inhibitor or use described herein, the kidney is from a donor having a KDRI of at least 1.50, at least 1.75, at least 2.0, or even at least 2.5. In some embodiments, the kidney is from a donor having a KDRI in the range for 1.25 to 1.50, 1.5-175, 1.75-2.0, 2.0-2.5 or even 2.5-3.0.

In some embodiments, the kidney is from a donor having a Kidney Donor Profile Index (KDPI) of at least 70%. In some embodiments, the KDPI is greater than 75%, greater than 80%, or even greater than 85%.

In some embodiments, the deceased donor kidney is preserved entirely by cold storage following removal from the donor and prior to implantation in the recipient.

In some embodiments, the deceased donor kidney is preserved by machine perfusion for at least a portion of time following removal from the donor and prior to implantation in the recipient.

In some embodiments, the outcomes of prophylaxis of Delayed Graft Function comprise at least one of prolonged time-to-first post-transplantation dialysis, shorter mean number and duration of post-transplantation dialysis and improved measured glomerular filtration rate (mGFR) during the first post-transplantation month.

In some embodiments, the deceased ECD donor is of age at least about 60 years.

In some embodiments, the deceased ECD donor is of age at least about 50 years, the donor having at least two conditions selected from the group consisting of history of hypertension, terminal serum creatinine level above about 1.5 mg/dL and cardiovascular accident as cause of death.

Unless otherwise defined, all technical and scientific terms used herein have the same meaning as commonly understood by one of ordinary skill in the art to which the invention pertains. In case of conflict, the specification, including definitions, takes precedence.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

As used herein, the term "Expanded criteria donor (ECD)" refers to a kidney donor over the age of 60, or a donor between the ages of 50 and 59 (inclusive) with at least two of the following: a history of high blood pressure, terminal serum creatinine level greater than 1.5 mg/dl, or cerebrovascular cause of brain death.

As used herein, the "standard criteria donor (SCD)" is a donor who is under 50 years of age and suffered brain death from any number of causes. This would include donors under the age of 50 who suffer from traumatic injuries or other medical problems such as a stroke. Pediatric donors are considered standard criteria donors; or a donor between the ages of 50 and 59 (inclusive) without two or more of the following: a history of high blood pressure, terminal serum creatinine level greater than 1.5 mg/dl, or cerebrovascular cause of brain death.

As used herein, the term "delayed graft function (DGF)" refers to the need for dialytic support within 7 days following kidney transfer, excluding allografts that fail within 24 hours post transplantation.

As used herein, the term "Kidney Donor Risk Profile (KDRI)" refers to the relative risk of post-transplant kidney graft failure (in an average, adult recipient) from a particular deceased donor compared to the median (50th percentile) donor, as defined by the U.S. Organ Procurement and Transplantation Network at http://optn.transplant.hrsa.gov/ContentDocuments/Kidney_Proposal_FAQ.pdf As used herein, the term "Kidney Donor Profile Index (KDPI)" refers to the risk of graft failure after kidney transplant, as defined by the U.S. Organ Procurement and Transplantation Network at http://optn.transplant.hrsa.gov/ContentDocuments/Kidney_Proposal_FAQ.pdf As used herein, the term "prophylaxis" of DGF refers to prevention or reduction of the intensity and duration of dialytic support, as manifested, for example, as a longer time interval between transplantation and the first dialysis treatment post-transplant, shorter mean duration of the initial post-transplantation course of dialysis or higher measured glomerular filtration rate at the end of the first post-transplant month.

As used herein, and unless otherwise specified, a "therapeutically effective amount" of a compound or molecule (i.e. temporary inhibitor) is an amount sufficient to provide a therapeutic benefit in the treatment or management of disorders associated with increased expression of p53 or to delay or minimize one or more symptoms associated with disorders associated with increased expression of p53.

As used herein, and unless otherwise specified, a "prophylactically effective amount" of a compound (i.e. inhibitor) is an amount sufficient to prevent, delay the onset or reduce the severity of disorders associated with increased expression of p53, or one or more symptoms associated with disorders associated with increased expression of p53 or prevent or delay its recurrence.

As used herein, the term "cold storage" refers to storage at a temperature of about 0° C. or less, for example, storage on ice. Such storage reduces the rate of energy consumption, for example, by the organ.

As used herein, the term "machine-perfusion" refers to storage at below-normal body temperatures, together with pump-driven circulation of a preservation solution through the blood vessels of the kidney. Such perfusion helps to sustain or replenish residual, intracellular energy stores while also reducing the rate at which they are consumed.

An "organ 35 years or older", refers to a body organ such as a kidney, a liver, a pancreas, a heart, a lung, an intestine, skin, a blood vessel, a brain, a retina, composite tissue, a blood vessel, an ear, a limb; or a part thereof, present in its native host, reimplanted to its native host, removed from a donor, or transplanted to a recipient, wherein the age is counted from birth of the host or donor.

A "method of prophylaxis of ischemic reperfusion injury (IRI)" refers to preventing, attenuating or reducing the damage caused by IRI, for example, preventing, attenuating or reducing cellular death and/or apoptosis and/or necrosis and/or oxidative stress.

As used herein, "an organ at risk of IRI" refers to an organ experiencing temporary cessation of blood flow or temporary global hypoxia. In a non-limiting example, a temporary cessation of blood flow may be due to thrombosis, vasoconstriction, and pressure on blood vessels for any reason or removal of the organ from the body with subsequent reimplantation or transplantation.

As used herein, "delayed graft function" or "DGF" refers to organ dysfunction following organ transplantation. When referring to a renal transplant, according to UNOS, DGF is defined as the requirement for dialysis within the first 7 days post-transplant.

As used herein, the term "prophylaxis" of DGF when referring to a renal transplant, refers to prevention or reduction of the frequency and/or duration of dialytic support, as manifested, for example, as a longer time interval between transplantation and the first dialysis treatment post-transplant, shorter mean duration of the initial post-transplantation course of dialysis or higher measured glomerular filtration rate at the end of the first post-transplant month.

Temporary Inhibitors of p53

Temporary inhibitors of p53 are intended to reduce the expression or function of a p53 gene for a length of time sufficient to evoke a therapeutic or prophylactic effect, for example on an organ or in a subject, without increasing the risk for cancerous growth. A method of temporary p53 inhibition is disclosed in, inter alia, U.S. Pat. Nos. 6,593,353; 6,982,277; 7,008,956 and 7,012,087, incorporated herein by reference in their entirety.

As used herein the term "inhibitor" refers to a compound, which is capable of reducing (partially or fully) the expression of a gene or the activity of a product of such gene (mRNA, protein) to an extent sufficient to achieve a desired biological or physiological effect. For example, the expression may be reduced to 90%, 80%, 70%, 60%, 50%, 40%, 30%, 20%, 10%, 5% or less than that observed in the absence of an inhibitor. Preferably, the inhibitor is a temporary inhibitor that reversibly reduces p53 expression or activity.

A "temporary" inhibitor of p53 refers to a molecule that exerts its effect for up to 24 hours, up to 36 hours, up to 48 hours, up to 72 hours, up to 96 hours, up to 120 hours or no longer than 120 hours, 7 days, 10 days, 20 days or 30 days.

An inhibitor of a "p53 gene" may be a small organic molecule, a protein, an antibody or fragment thereof, a peptide, a polypeptide, a peptidomimetic or a nucleic acid molecule; or a pharmaceutically acceptable salt or prodrug thereof.

A small organic molecule may be, for example, pifithrin.

By "nucleic acid aptamer" as used herein is meant a nucleic acid molecule that binds specifically to a target molecule wherein the nucleic acid molecule has sequence that comprises a sequence recognized by the target molecule, preferably in vivo. The target molecule can be any molecule of interest. For example, the aptamer can be used to bind to a ligand-binding domain of a protein, thereby preventing interaction of the naturally occurring ligand with the protein.

The term "antibody" refers to IgG, IgM, IgD, IgA, and IgE antibody, inter alia. The definition includes polyclonal antibodies or monoclonal antibodies. This term refers to whole antibodies or fragments of antibodies comprising an antigen-binding domain, e.g. antibodies without the Fc portion, single chain antibodies, miniantibodies, fragments consisting of essentially only the variable, antigen-binding domain of the antibody, etc. The term "antibody" may also refer to antibodies against polynucleotide sequences obtained by cDNA vaccination. The term also encompasses antibody fragments which retain the ability to selectively bind with their antigen, for example a p53 gene product, and are exemplified as follows, inter alia:

(1) Fab, the fragment which contains a monovalent antigen-binding fragment of an antibody molecule which can be produced by digestion of whole antibody with the enzyme papain to yield a light chain and a portion of the heavy chain;
(2) (Fab')2, the fragment of the antibody that can be obtained by treating whole antibody with the enzyme pepsin without subsequent reduction; F(ab'2) is a dimer of two Fab fragments held together by two disulfide bonds;
(3) Fv, defined as a genetically engineered fragment containing the variable region of the light chain and the variable region of the heavy chain expressed as two chains; and
(4) Single chain antibody (SCA), defined as a genetically engineered molecule containing the variable region of the light chain and the variable region of the heavy chain linked by a suitable polypeptide linker as a genetically fused single chain molecule, including a scFv.

CDR grafting may be performed to alter certain properties of the antibody molecule including affinity or specificity. A non-limiting example of CDR grafting is disclosed in U.S. Pat. No. 5,225,539.

Single-domain antibodies are isolated from the unique heavy-chain antibodies of immunized Camelidae, including camels and llamas. The small antibodies are very robust and bind the antigen with high affinity in a monomeric state. U.S. Pat. No. 6,838,254 describes the production of antibodies or fragments thereof derived from heavy chain immunoglobulins of Camelidae.

A monoclonal antibody (mAb) is a substantially homogeneous population of antibodies to a specific antigen, and is well known in the art. Monoclonal antibodies are obtained by methods known to those skilled in the art.

A mAb may be of any immunoglobulin class including IgG, IgM, IgE, IgA, and any subclass thereof. A hybridoma producing a mAb may be cultivated in vitro or in vivo. High titers of mAbs are obtained in vivo for example wherein cells from the individual hybridomas are injected intraperitoneally into pristine-primed Balb/c mice to produce ascites fluid containing high concentrations of the desired mAbs. mAbs of isotype IgM or IgG may be purified from such ascites fluid, or from culture supernatants, using column chromatography methods well known to those of skill in the art.

By "specific binding affinity" is meant that the antibody binds to a p53 polypeptide or fragment thereof with greater affinity than it binds to another polypeptide under similar conditions.

The term "epitope" is meant to refer to that portion of a molecule capable of being bound by an antibody which can also be recognized by that antibody. An "antigen" is a molecule or a portion of a molecule capable of being bound by an antibody which is additionally capable of inducing an animal to produce antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies that may be evoked by other antigens.

Epitopes or antigenic determinants usually consist of chemically active surface groupings of molecules such as amino acids or sugar side chains and have specific three-dimensional structural characteristics as well as specific charge characteristics.

The antibody may be a human or nonhuman antibody. A nonhuman antibody may be humanized by recombinant methods to reduce its immunogenicity in man. Methods for humanizing antibodies are known to those skilled in the art.

A mAb or fragment, chimera or humanized antibody thereof may be used as an inhibitor of the p53 gene product, per se, or may be used to conjugate to a temporary inhibitor of a p53 gene. When conjugated to a temporary inhibitor of a p53 gene, the antibody may serve to target an organ at risk of IRI.

As used herein, the term "peptide" is used broadly to mean peptides, proteins, fragments of proteins and the like. One skilled in the art will recognize that the peptides disclosed herein may be synthesized as peptide mimetics. A peptide mimetic or "peptidomimetic", is a molecule that mimics the biological activity of a peptide but is not completely peptidic in nature. The term "peptidomimetic," as used herein, means a peptide-like molecule that has the activity of the peptide upon which it is structurally based. Such peptidomimetics include chemically modified peptides, peptide-like molecules containing non-naturally occurring amino acids, and peptides and have an activity such as selective targeting activity of the peptide upon which the peptidomimetic is derived. A peptidomimetic can include amino acid analogs and can be a peptide-like molecule which contains, for example, an amide bond isostere such as a retro-inverso modification; reduced amide bond; methylenethioether or methylenesulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein. A peptide, protein or fragment thereof may be used as an inhibitor of the p53 gene product, per se, or may be used to conjugate to a temporary inhibitor of a p53 gene. When conjugated to a temporary inhibitor of a p53 gene, the peptide may serve to target facilitate delivery of the inhibitor to an organ at risk of IRI.

As used herein a "composition" or "therapeutic composition" refers to a preparation of one or more of the active ingredients with other components such as pharmaceutically acceptable carriers and excipients. The purpose of a therapeutic composition is to facilitate administration of an active ingredient to a subject.

The term "pharmaceutically acceptable carrier" refers to a carrier or a diluent that does not cause significant irritation to a subject and does not substantially abrogate the activity and properties of the administered active ingredients. An adjuvant is included under these phrases. The term "excipient" refers to an inert substance added to a therapeutic composition to further facilitate administration of an active ingredient.

Therapeutic compositions used in implementing the teachings herein may be formulated using techniques with which one of average skill in the art is familiar in a conventional manner using one or more pharmaceutically acceptable carriers comprising excipients and adjuvants, which facilitate processing of the active ingredients into a therapeutic composition and generally includes mixing an amount of the active ingredients with the other components. Suitable techniques are described in "Remington's Pharmaceutical Sciences," Mack Publishing Co., Easton, Pa., latest edition, which is incorporated herein by reference. For example, therapeutic compositions useful in implementing the teachings herein may be manufactured by one or more processes that are well known in the art, e.g., mixing, blending, homogenizing, dissolving, granulating, emulsifying, encapsulating, entrapping and lyophilizing processes.

Therapeutic compositions suitable for implementing the teachings herein include compositions comprising active ingredients in an amount effective to achieve the intended purpose (a therapeutically effective amount). Determination of a therapeutically effective amount is well within the capability of those skilled in the art, for example, is initially estimated from animal models.

Federal law requires that the use of pharmaceutical compositions in the therapy of humans be approved by an agency of the Federal government. In the United States, enforcement is the responsibility of the Food and Drug Administration, which issues appropriate regulations for securing such approval, detailed in 21 U.S.C. section 301-392. Similar approval is required for most countries. Regulations vary from country to country, but individual procedures are well known to those in the art and the compositions and methods provided herein preferably comply accordingly.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced.

In the Figures.

DESCRIPTION OF SOME EMBODIMENTS OF THE INVENTION

Figure 1:
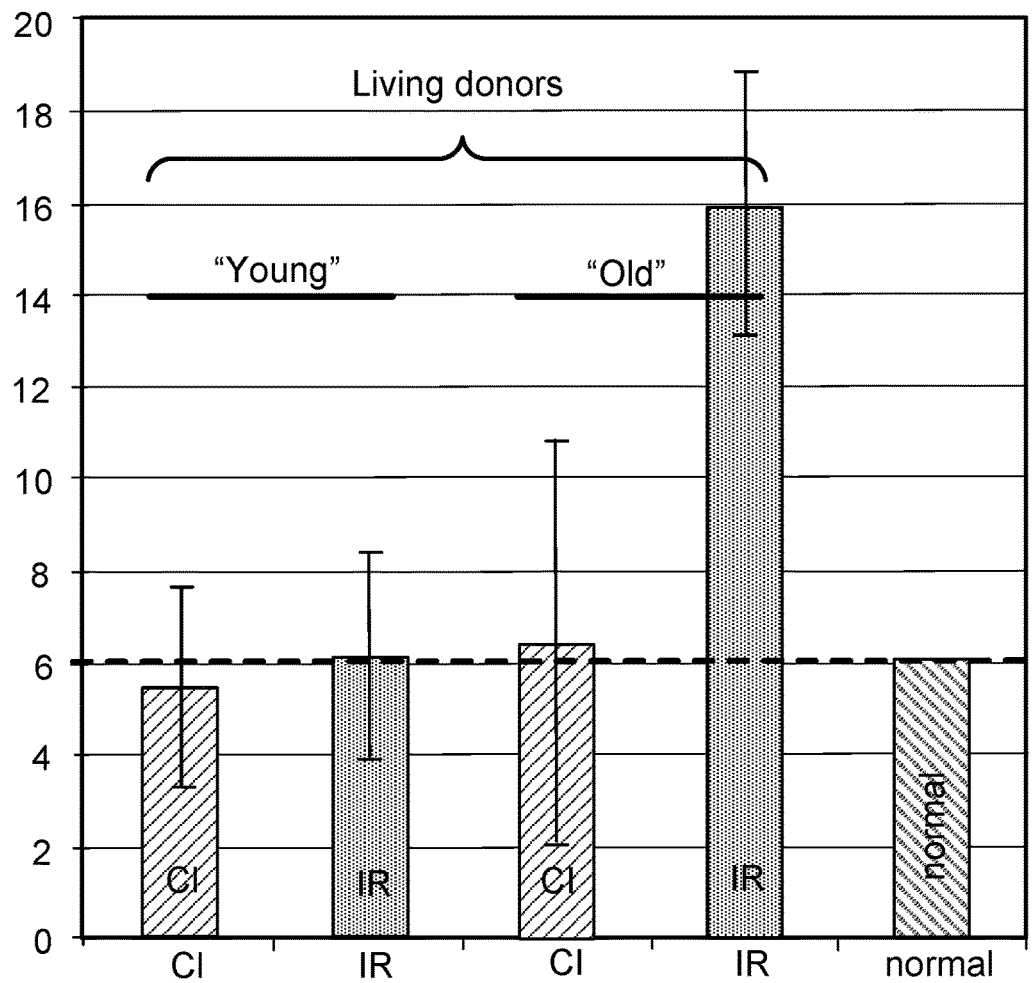
FIG. 1 is a graph showing protein levels of ischemia induced activation of p53 in kidneys from young and old rat donors.

Provided herein are compounds and compositions that temporarily inhibit the p53 gene, and the use of such compounds for prophylaxis of IRI in organs, a reduction in the amount and duration of dialysis in deceased donor kidney transplant recipients and for prevention of Delayed Graft Function (DGF) in recipients of Expanded Criteria Donor (ECD) kidneys.

Temporary Inhibitors of p53

Temporary inhibitors of p53 are intended to reduce the expression or function of a p53 gene for a length of time sufficient to evoke a therapeutic or prophylactic effect, for example in an organ or in a subject, without increasing the risk for cancerous growth. A method of temporary p53 inhibition is disclosed in, inter alia, U.S. Pat. Nos. 6,593,353; 6,982,277; 7,008,956 and 7,012,087, incorporated herein by reference in their entirety.

As used herein the term "inhibitor" refers to a compound, which is capable of reducing (partially or fully) the expression of a gene or the activity of a product of such gene (mRNA, protein) to an extent sufficient to achieve a desired biological or physiological effect. For example, the expression may be reduced to 90%, 80%, 70%, 60%, 50%, 40%, 30%, 20%, 10%, 5% or less than that observed in the absence of an inhibitor. Preferably, the inhibitor is a temporary inhibitor that reversibly reduces p53 expression or activity.

A "temporary" inhibitor of p53 refers to a molecule that exerts its effect for up to 24 hours, up to 36 hours, up to 48 hours, up to 72 hours, up to 96 hours, up to 120 hours or no longer than 30 days.

An inhibitor of a "p53 gene" may be a small organic molecule, a protein, an antibody or fragment thereof, a peptide, a polypeptide, a peptidomimetic or a nucleic acid molecule; or a pharmaceutically acceptable salt or prodrug thereof.

A small organic molecule of may be, for example, pifithrin.

An inhibitor of the p53 gene can be an "aptamer", which are nucleic acid or peptide molecules that bind to a specific protein target molecule (see, for example, patent documents: Sundaram, et al., Eu. J. Pharm. Sci. 2013, 48:259-271; WO 1992/014843 U.S. Pat. Nos. 5,861,254; 5,756,291; 6,376,190.

Aptamers may be used to inhibit target genes or to target other inhibitors to specific target cells or organs (see for example US 2006/0105975).

Aptamers are meant to include "thiophosphate oligonucleotide aptamers," "thioaptamers" or "TAs", which are a class of ligand that structurally differs from RNA and DNA capable of binding proteins with high (nM) affinity. TAs may also be used to inhibit target genes or as targeting moieties, per se.

In certain preferred embodiments the compounds that down-regulate or inhibit expression of the p53 gene are nucleic acid molecules (for example, antisense molecules, short interfering nucleic acid (siNA), short interfering RNA (siRNA), double-stranded NA (dsNA), micro-RNA (miRNA) or short hairpin RNA (shRNA)) that bind a nucleotide sequence (such as an mRNA sequence) or portion thereof, encoding p53, for example, the mRNA coding sequence (SEQ ID NO:1-7) for human p53, encoding one or more proteins or protein subunits. In various embodiments the nucleic acid molecule is selected from the group consisting of unmodified or chemically modified dsNA compound such as a dsRNA, a siRNA or shRNA that down-regulates the expression of a p53 gene.

In some embodiments the nucleic acid molecule is a synthetic, unmodified double stranded RNA (dsRNA) compound that down-regulates p53 expression.

In some preferred embodiments the nucleic acid molecule is a synthetic, chemically modified double-stranded RNA (dsRNA) compound that down-regulates p53 expression. In certain preferred embodiments, "p53" refers to human p53 gene. In certain preferred embodiments, "target gene" refers to human p53 gene.

The chemically modified nucleic acid molecules and compositions provided herein exhibit beneficial properties, including at least one of increased serum stability, improved cellular uptake, reduced off-target activity, reduced immunogenicity, improved endosomal release, improved specific delivery to target tissue or cell and increased knock down/down-regulation activity when compared to corresponding unmodified nucleic acid molecules.

Nucleic Acid Compounds

In the context of this disclosure, the terms "nucleic acid compound" or "nucleic acid molecule" refer to an oligomer (oligonucleotide) or polymer (polynucleotide) of deoxyribonucleic acid (DNA) or ribonucleic acid (RNA) or a combination thereof. This term includes compounds composed of naturally occurring nucleobases, sugars and covalent internucleoside linkages.

A "dsRNA" is a small double stranded nucleic acid molecule which includes RNA and RNA analogs. A "dsNA" is a small double stranded nucleic acid molecule which includes RNA, modified nucleotides and/or unconventional nucleotides. The terms dsRNA and dsNA may be used interchangeably.

The term "dsRNA" relates to two strands of anti-parallel polyribonucleic acids held together by base pairing. The two strands can be of identical length or of different lengths provided there is enough sequence homology between the two strands that a double stranded structure is formed with at least 80%, 85%, 90%, 95%, 96%, 97%, 98%, 99% or 100% complementarity over the entire length. According to one embodiment, there are no nucleotide overhangs for the dsRNA molecule. According to another embodiment, the dsRNA molecule comprises overhangs, which may be selected from nucleotide overhangs, non-nucleotide overhangs or a combination thereof. According to other embodiments, the strands are aligned such that there are between 1-10 bases, preferably between 1-6 bases at least at the end of the strands, which do not align such that an overhang of 1-10 residues occurs at one or both ends of the duplex when strands are annealed.

In some embodiments, the dsRNA in the present application is between 15 and 100 bp, between 15 and 50 bp, between 15 and 40 bp, between 15 and 30, or between 15 and 25 bp. In a further embodiment, the 5' and/or 3' ends of the sense and/or antisense strands of the dsRNA comprise 1, 2, 3, 4, 5, 6, 7, 8, 9, 10 or more nucleotide overhangs. In some embodiments, the dsRNA comprises between 1-6 nucleotide overhangs on the 5' and/or 3' ends of the sense and/or antisense strands. In another embodiments, the ends of the dsRNA are blunt.

The term "siRNA" relates to small inhibitory dsRNA (generally between 15-25 bp) that may interact with the RNA interference (RNAi) machinery and induce the RNAi pathway. Typically, siRNA are chemically synthesized as 15-25 mers, preferably comprising a central 15-19 bp duplex region with or without symmetric 2-base or more 3' overhangs on the termini.

The strands of a double stranded interfering RNA (e.g. siNA and siRNA) may be connected to form a hairpin or stem-loop structure (e.g. a shRNA). Thus, as mentioned the RNA silencing agent of some embodiments of the invention may also be a short hairpin RNA (shRNA).

The term "shRNA", as used herein, refers to a RNA molecule having a stem-loop structure, comprising a first and second region of complementarity sequence, the degree of complementarity and orientation of the regions being sufficient such that base pairing occurs between the regions, the first and second regions being sufficient such that base pairing occurs between the regions, the first and second regions being bound by a loop region, the loop resulting from lack of base pairing between nucleotides (or nucleotide analogs) within the loop region.

As used herein the term "modified nucleotide" refers to a nucleotide comprising at least one modification which may be a sugar modification, a nucleobase modification or an internucleotide linkage modification (between said nucleotide and a consecutive nucleotide) or a combination thereof. Such modified nucleotides are often preferred over the naturally occurring forms because of desirable properties such as, for example, enhanced cellular uptake, enhanced affinity for a nucleic acid target and enhanced nuclease stability.

Internucleotide Linkage Modifications:

The naturally occurring internucleoside linkage that makes up the backbone of RNA and DNA is a 3' to 5' phosphodiester linkage. The nucleic acid compounds according to some embodiments of the invention may comprise at least one modified (non-naturally occuring) internucleotide linkage. Modified internucleoside linkages may include internucleoside linkages that retain a phosphorus atom and internucleoside linkages that do not have a phosphorus atom.

Non-limiting examples of modified internucleoside linkages containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-allylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, phosphonoacetate (PACE) and thiophosphonoacetate, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage.

Non-limiting examples of modified internucleotide linkages that do not include a phosphorus atom therein include a short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane linkages; sulfide, sulfoxide and sulfone linkages; formacetyl and thioformacetyl linkages; methylene formacetyl and thioformacetyl linkages; riboacetyl linkages; alkene containing linkages; sulfamate linkages; methyleneimino and methylenehydrazino linkages; sulfonate and sulfonamide linkages; amide linkages; and other linkages having mixed N, O, S and $CH_2$ component parts.

Non-limiting examples of heteroatom internucleoside linkages include —$CH_2$—NH—O—$CH_2$—, —$CH_2$—N($CH_3$)—O—$CH_2$— (known as a methylene (methylimino) or MMI linkage), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the naturally occuring phosphodiester internucleotide linkage is represented as —O—P(=O)(OH)—O—$CH_2$—).

Sugar Modifications:

Sugar moieties in nucleic acid compounds disclosed herein may include 2'-hydroxylpentofuranosyl sugar moiety without any modification. Alternatively, nucleic acid compounds of the invention may contain one or more substituted or otherwise modified sugar moieties. A preferred position for a sugar substituent group is the 2'-position not usually used in the native 3' to 5'-internucleoside linkage. Other preferred positions are the 3' and the 5'-termini. 3'-sugar positions are open to modification when the linkage between two adjacent sugar units is a 2'-5'-linkage. Preferred sugar substituent groups include: —OH; —F; —O-alkyl, —S-alkyl, or —N-alkyl; —O-alkenyl, —S-alkenyl, or —N-alkenyl; —O-alkynyl, —S-alkynyl or —N-alkynyl; or —O-alkyl-O-alkyl, wherein the alkyl, alkenyl and alkynyl may be substituted or unsubstituted C1 to C10 alkyl or C2 to C10 alkenyl and alkynyl, C1 to C10 lower alkyl, substituted lower alkyl, alkenyl, alkynyl, alkaryl, aralkyl (e.g. -propargyl, -propyl, -ethynyl, -ethenyl and propenyl). Non-limiting examples of sugar modification include methoxy (—O—$CH_3$), methylthio (—S—$CH_3$), —OCN, —$OCF_3$, amino-propoxy (—$OCH_2CH_2CH_2NH_2$), allyl (—$CH_2$—CH=$CH_2$), —O-allyl (—O—$CH_2$—CH=$CH_2$), —O[($CH_2)_nO]_mCH_3$, —O($CH_2)_nOCH_3$, —O($CH_2)_nNH_2$, —O($CH_2)_nCH_3$, —O($CH_2)_nONH_2$, and —O($CH_2)_nON[($CH_2)_nCH_3]_2$, where n and m are from 1 to about 10, 2'-methoxyethoxy (2'-O—$CH_2CH_2OCH_3$), 2'-dimethylaminooxyethoxy (2'-O($CH_2)_2ON(CH_3)_2$), —N-methylacetamide (2'-O—$CH_2$—C(=O)—N(H)$CH_3$), —F, —Cl, —Br, —I, —CN, —$SOCH_3$, —$SO_2CH_3$, —$ONO_2$, —$NO_2$, —$N_3$, —$NH_2$, imidazole, carboxylate, thioate, heterocycloalkyl, heterocycloalkaryl, aminoalkylamino, polyalkylamino and substituted silyl.

The 2'-sugar substituent groups described supra may be incorporated in the arabino (up) position or ribo (down) position. An example of 2'-arabino modification is 2'-F (2'-F-arabino modified nucleotide is typically referred to as fluoroarabimo nucleic acid (FANA)). According to some embodiments, sugar moieties may be modified such as, 2'-deoxy-pentofuranosyl sugar moiety.

In some preferred embodiments, the modified nucleotide comprises at least one 2'-O-methyl sugar modified ribonucleotide.

Similar modifications to the ones described supra may also be made at positions other than the 2' position of the sugar moiety, particularly at the 3' position of the sugar of a 3' terminal nucleoside or in a 2'-5' linked nucleotides and the 5' position of a 5' terminal nucleotide.

Nucleobase Modifications:

The nucleic acid compounds disclosed herein may comprise "unmodified" or "natural" nucleobases including the purine bases adenine (A) and guanine (G), and the pyrimidine bases thymine (T), cytosine (C) and uracil (U). Alternatively, nucleic acid compounds of the invention may contain one or more substituted or otherwise modified nucleobase. Non-limiting examples of nucleobase modifications include 5-methylcytosine (5-me-C), 5-hydroxymethyl cytosine, xanthine, hypoxanthine, 2-aminoadenine, 6-methyl adenine, 6-methyl guanine, 2-propyl adenine, 2-propyl guanine and other alkyl derivatives of adenine and guanine, 2-thiouracil, 2-thiothymine, 2-thiocytosine, 5-halouracil, 5-halocytosine, 5-propynyl uracil, 5-propynyl cytosine and other alkynyl derivatives of pyrimidine bases, 6-azo uracil, 6-azo cytosine, 6-azo thymine, 5-uracil (pseudouracil), 4-thiouracil, 8-halo adenine, 8-halo guanines, 8-amino adenine, 8-amino guanine, 8-thiol adenine, 8-thiol guanine, 8-thioalkyl adenine, 8-thioalkyl guanine, 8-hydroxyl adenine, 8-hydroxyl guanine and other 8-substituted adenines and guanines, 5-halo (e.g. 5-bromo) uracil, 5-halo (e.g. 5-bromo) cytosine, 5-trifluoromethyl uracil, 5-trifluoromethyl guanine and other 5-substituted uracils and cytosines, 7-methylguanine and 7-methyladenine, 2-F-adenine, 2-amino-adenine. Modified nucleobases moieties may also include those in which the purine or pyrimidine base is replaced with other heterocycles, for example 8-azaguanine, 8-azaadenine, 7-deaza-guanine, 7-deaza-adenine, 3-deazaguanine and 3-deazaadenine. Additional examples include nucleobases having non-purinyl and non-pyrimidinyl bases such as 2-aminopyridine, 2-pyridone and triazine.

Nucleotide Analogues:

The nucleic acid compounds, according to some embodiments of the invention, may comprise one or more nucleotide analogues. The term "Nucleotide analogues" alternatively referred to as "nucleotide mimetics" as used herein refers to nucleotides wherein the furanose ring or the furanose ring and the internucleotide linkage are replaced with alternative groups. The nucleobase moiety (modified or unmodified) is maintained.

Non-limiting examples of nucleotide analogues include a peptide nucleic acid (PNA), in which the sugar-backbone of a nucleotide is replaced with an amide containing backbone, in particular an aminoethylglycine backbone; a morpholino nucleic acid, in which the furanose ring is replaced with a morpholine ring; a cyclohexenyl nucleic acid (CeNA), in which the furanose ring is replaced with a cyclohenyl ring; a nucleic acid comprising bicyclic sugar moiety (BNAs), such as "Locked Nucleic Acids" (LNAs) in which the 2'-hydroxyl group of the ribosyl sugar ring is linked to the 4' carbon atom of the sugar ring thereby forming a 2'-C,4'-C-oxymethylene linkage to form the bicyclic sugar moiety, a 2'-O,4'-ethylene-bridged nucleic acid (ENA) and the like; a threose nucleic acid in which the hydroxylpentofuranosyl sugar moiety is replaced with threose sugar moiety; an arabino nucleic acid (ANA) in which the ribose sugar moiety is replaced with arabinose sugar moiety; an unlocked nucleic acid (UNA), in which the ribose ring is replaced with an acyclic analogue, lacking the C2'-C3' bond; a mirror nucleotide in which the typical D-ribose ring is replaced with a L-ribose ring, thus forming a nucleotide which is a mirror image of natural nucleotide and a nucleotide comprising a 2'-5' linkage, in which the typical 3' to 5' internucleotide linkage is replaced with a 2' to 5' linkage (preferably a 2'-5' phosphate based internucleotide linkage). It is to be emphasized that the nucleotide analogues described, may be further modified as described above for "modified nucleotide".

The nucleic acid compound according to some embodiments of the invention may further comprise at least one unconventional moiety. The term "unconventional moiety" as used herein refers to as an "abasic nucleotide" or an "abasic nucleotide analog". Such abasic nucleotide encompasses sugar moieties lacking a base or having other chemical groups in place of base at the 1' position. The abasic nucleotide may comprise an abasic ribose moiety (unmodified or modified as described supra) or an abasic deoxyribose moiety (unmodified or modified). Additionally, the abasic nucleotide may be a reverse abasic nucleotide, e.g., where a reverse abasic phosphoramidite is coupled via a 5' amidite (instead of 3' amidite) resulting in a 5'-5' phosphate linkage. The term "abasic nucleotide analog encompasses any nucleotide analog as defined above, wherein the sugar moiety is lacking a base or having other chemical groups in place of base at the 1' position.

Terminal Modifications:

Modifications can be made at terminal phosphate groups. Non-limiting examples of different stabilization chemistries can be used, for example to stabilize the 3'-end of nucleic acid sequences, include [3-3']-inverted deoxyribose; deoxyribonucleotide; [5'-3']-3'-deoxyribonucleotide; [5'-3']-ribonucleotide; [5'-3']-3'-O-methyl ribonucleotide; 3'-glyceryl; [3'-5']-3'-deoxyribonucleotide; [3'-3']-deoxyribonucleotide; [5'-2']-deoxyribonucleotide; and [5-3']-dideoxyribonucleotide. In addition to modified and unmodified backbone structures indicated, these structures can be combined with different internucleotide linkage modifications, sugar modifications and/or nucleobase modifications as described above.

The nucleic acid compounds according to some embodiments disclosed herein may comprise blunt ends (i.e., ends do not include any overhanging nucleotides). Alternatively, the nucleic acid compounds of the invention may comprise at least one overhang, said overhangs may be selected from the group consisting of nucleotide overhangs (e.g. 3'-terminal nucleotide overhangs) and non-nucleotide overhangs.

In particular embodiments, chemically modified dsNA compounds that target p53, compositions and kits comprising same and methods of use thereof in the treatment of a condition or pathology involving apoptosis (programmed cell death), are provided herein. In particular embodiments the invention, relates to use of such compounds for prophylaxis of Delayed Graft Function (DGF) in a recipient of a kidney from a deceased Expanded Criteria Donor (ECD), including as a kidney that has been preserved entirely by cold storage following removal from the donor and prior to implantation in the recipient.

In some embodiments the nucleic acid compounds that target and down-regulate the p53 gene are having oligonucleotide sequences (SEQ ID NOS: 8-37). In some embodiments pharmaceutically acceptable salts of such compounds are used. In some embodiments of nucleic acid compounds having a double-stranded structure, the oligonucleotide sequence of one of the strands is selected from one of SEQ ID NOS: 8-20, 34 and 36 and the oligonucleotide sequence of the other strand is selected from one of SEQ ID NOS: 21-33, 35 and 37. For example, SEQ ID NO:21; SEQ ID NO:22; SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; SEQ ID NO:32; SEQ ID NO:33; SEQ ID NO:35; or SEQ ID NO:37.

In some embodiments, the inhibitors of p53 are nucleic acid molecules, or pharmaceutically acceptable salts of such molecules, having a double-stranded structure in which (a) the nucleic acid molecule is a duplex which includes a sense strand and a complementary antisense strand; (b) each strand of the nucleic acid molecule is 19 nucleotides in length; (c) a 19 nucleotide sequence of the antisense strand is complementary to a consecutive sequence of a mRNA encoding mammalian p53 (e.g., SEQ ID NOS: 1-7) or portion thereof; and (d) the sense strand and antisense strand are selected from the oligonucleotide sequences set forth in Table 1 below (SEQ ID NOS: 8-37).

TABLE 1

Selected sense strand and antisense strand oligonucleotide sequences for nucleic acid compounds targeting p53

| SEQ ID NO | Sense strand (5' > 3') | SEQ ID NO | Antisense strand (5' > 3') |
|---|---|---|---|
| 8 | 5' CAGACCUAUGGAAACUACU 3' | 21 | 5' AGUAGUUUCCAUAGGUCUG 3' |
| 9 | 5' GGAUGUUUGGGAGAUGUAA 3' | 22 | 5' UUACAUCUCCCAAACAUCC 3' |
| 10 | 5' GACUCAGACUGACAUUCUA 3' | 23 | 5' UAGAAUGUCAGUCUGAGUC 3' |

TABLE 1-continued

Selected sense strand and antisense strand oligonucleotide sequences for nucleic acid compounds targeting p53

| SEQ ID NO | Sense strand (5' > 3') | SEQ ID NO | Antisense strand (5' > 3') |
|---|---|---|---|
| 11 | 5' GGGUUGGUAGUUUCUACAA 3' | 24 | 5' UUGUAGAAACUACCAACCC 3' |
| 12 | 5' GGGAUGUUUGGGAGAUGUA 3' | 25 | 5' UACAUCUCCCAAACAUCCC 3' |
| 13 | 5' GGAUCCACCAAGACUUGUA 3' | 26 | 5' UACAAGUCUUGGUGGAUCC 3' |
| 14 | 5' GAGGGAUGUUUGGGAGAUA 3' | 27 | 5' UAUCUCCCAAACAUCCCUC 3' |
| 15 | 5' GGGCCUGACUCAGACUGAA 3' | 28 | 5' UUCAGUCUGAGUCAGGCCC 3' |
| 16 | 5' GACUCAGACUGACAUUCUU 3' | 29 | 5' AAGAAUGUCAGUCUGAGUC 3' |
| 17 | 5' GCAUUUGCACCUACCUCAA 3' | 30 | 5' UUGAGGUAGGUGCAAAUGC 3' |
| 18 | 5' GGAUGUUUGGGAGAUGUAU 3' | 31 | 5' AUACAUCUCCCAAACAUCC 3' |
| 19 | 5' GGGCCUGACUCAGACUGAU 3' | 32 | 5' AUCAGUCUGAGUCAGGCCC 3' |
| 20 | 5' CAGACCUAUGGAAACUACA 3' | 33 | 5' UGUAGUUUCCAUAGGUCUG 3' |
| 34 | 5' CCGAGUGGAAGGAAAUUUG 3' | 35 | 5' CAAAUUUCCUUCCACUCGG 3' |
| 36 | 5' GAGAAUAUUUCACCCUUCA 3' | 37 | 5' UGAAGGGUGAAAUAUUCUC 3' |

All positions given in Table 1 are 5'>3' on the sense strand and on the antisense strand.

In other embodiments, the inhibitors of p53 are nucleic acid compounds (e.g., dsNA molecules), or pharmaceutically acceptable salts of such compounds, in which (a) the nucleic acid molecule is a duplex which includes a sense strand and a complementary antisense strand; (b) each strand of the nucleic acid molecule is 19 nucleotides in length; (c) a 19 nucleotide sequence of the antisense strand is complementary to a consecutive sequence of a mRNA encoding mammalian p53 (e.g., SEQ ID NOS: 1-7) or portion thereof; and (d) the sense strand and antisense strand comprise sequence pairs set forth in Table 2 below.

TABLE 2

Selected pairs of sense and antisense strands for generating double-stranded nucleic acid compounds targeting p53

| Pair Name | SEQ ID NO | Sense strand (5' > 3') | SEQ ID NO | Antisense strand (5' > 3') |
|---|---|---|---|---|
| p53_1 | 36 | 5' GAGAAUAUUUCACCCUUCA 3' | 37 | 5' UGAAGGGUGAAAUAUUCUC 3' |
| p53_13 | 8 | 5' CAGACCUAUGGAAACUACU 3' | 21 | 5' AGUAGUUUCCAUAGGUCUG 3' |
| p53_34 | 9 | 5' GGAUGUUUGGGAGAUGUAA 3' | 22 | 5' UUACAUCUCCCAAACAUCC 3' |
|  | 9 | 5' GGAUGUUUGGGAGAUGUAA 3' | 31 | 5' AUACAUCUCCCAAACAUCC 3' |
| p53_35 | 10 | 5' GACUCAGACUGACAUUCUA 3' | 23 | 5' UAGAAUGUCAGUCUGAGUC 3' |
| p53_36 | 11 | 5' GGGUUGGUAGUUUCUACAA 3' | 24 | 5' UUGUAGAAACUACCAACCC 3' |
| p53_37 | 12 | 5' GGGAUGUUUGGGAGAUGUA 3' | 25 | 5' UACAUCUCCCAAACAUCCC 3' |
| p53_38 | 13 | 5' GGAUCCACCAAGACUUGUA 3' | 26 | 5' UACAAGUCUUGGUGGAUCC 3' |
| p53_39 | 14 | 5' GAGGGAUGUUUGGGAGAUA 3' | 27 | 5' UAUCUCCCAAACAUCCCUC 3' |
| p53_40 | 15 | 5' GGGCCUGACUCAGACUGAA 3' | 28 | 5' UUCAGUCUGAGUCAGGCCC 3' |
| p53_41 | 16 | 5' GACUCAGACUGACAUUCUU 3' | 29 | 5' AAGAAUGUCAGUCUGAGUC 3' |
| p53_42 | 17 | 5' GCAUUUGCACCUACCUCAA 3' | 30 | 5' UUGAGGUAGGUGCAAAUGC 3' |
| p53_43 | 18 | 5' GGAUGUUUGGGAGAUGUAU 3' | 31 | 5' AUACAUCUCCCAAACAUCC 3' |
|  | 18 | 5' GGAUGUUUGGGAGAUGUAU 3' | 22 | 5' UUACAUCUCCCAAACAUCC 3' |
| p53_44 | 19 | 5' GGGCCUGACUCAGACUGAU 3' | 32 | 5' AUCAGUCUGAGUCAGGCCC 3' |
|  | 19 | 5' GGGCCUGACUCAGACUGAU 3' | 28 | 5' UUCAGUCUGAGUCAGGCCC 3' |

TABLE 2-continued

Selected pairs of sense and antisense strands for generating
double-stranded nucleic acid compounds targeting p53

| Pair Name | SEQ ID NO | Sense strand (5' > 3') | SEQ ID NO | Antisense strand (5' > 3') |
|---|---|---|---|---|
| p53_45 | 20 | 5' CAGACCUAUGGAAACUACA 3' | 33 | 5' UGUAGUUUCCAUAGGUCUG 3' |
|  | 20 | 5' CAGACCUAUGGAAACUACA 3' | 21 | 5' AGUAGUUUCCAUAGGUCUG 3' |

All positions given in Table 2 are 5'>3' on the sense strand and on the antisense strand.

In preferred embodiments the sense strand and the antisense strand of the double-stranded nucleic acid molecule are selected from the group consisting of a sense strand SEQ ID NO: 36 and an antisense strand SEQ ID NO: 37; a sense strand SEQ ID NO: 16 and an antisense strand SEQ ID NO: 29; a sense strand SEQ ID NO: 19 and an antisense strand SEQ ID NO: 32; and a sense strand SEQ ID NO: 19 and an antisense strand SEQ ID NO: 28.

QP-1002

QPI-1002 (also known as "I5NP", CAS Number 1231737-88-4) having molecular weight 12,319.75 Daltons (protonated form), QPI-1002 Sodium Salt: 13,111.10 Daltons (sodium salt) is nuclease-resistant, chemically modified, synthetic, double-stranded (19-base pair) RNA oligonucleotide designed to temporarily inhibit the expression of the pro-apoptotic gene, p53, via activation of the RNA interference (RNAi) pathway. The sodium salt of QPI-1002 has the molecular formula: $C_{380}H_{448}O_{262}N_{140}P_{36}Na_{36}$. The RNA duplex is partially protected from nuclease degradation using a modification on the 2' position of the ribose sugar.

The structure of QPI-1002 is as follows:

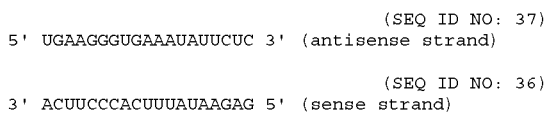

wherein each of A, C, U and G is a ribonucleotide and each consecutive ribonucleotide is joined to the next ribonucleotide by a covalent bond; and wherein alternating ribonucleotides in both the antisense strand and the sense strand are 2'-O-methyl sugar modified ribonucleotides and a 2'-O-methyl sugar modified ribonucleotide is present at both the 5' terminus and the 3' terminus of the antisense strand and an unmodified ribonucleotide is present at both the 5' terminus and the 3' terminus of the sense strand. Such that in the antisense strand each of the first, third, fifth, seventh, ninth, eleventh, thirteenth, fifteenth, seventeenth and nineteenth ribonucleotide is a 2'-O-Methyl sugar modified ribonucleotide; and in the sense strand each of the second, fourth, sixth, eighth, tenth, twelfth, fourteenth, sixteenth and eighteenth ribonucleotide is a 2'-O-Methyl sugar modified ribonucleotide.

p53 protein is activated as a consequence of the acute renal tubular (ischemia-reperfusion) injury that can occur in donor kidneys transplanted following hypothermic preservation, particularly prolonged hypothermic preservation, such as for periods of 26 hours or more, and after removal of patients from cardiopulmonary bypass following major cardiac surgery, leading to the induction of apoptosis/programmed cell death. The temporary inhibition of p53 expression by QPI-1002 affords proximal tubular epithelial cells time to repair cellular damage and, therefore, avoid induction of apoptosis. Temporarily blocking induction of apoptosis has been shown by the present inventors reduce the severity, frequency or duration of reperfusion injury following prolonged ischemia.

The administered dose of the temporary inhibitor of p53 must be effective to achieve prophylaxis, including but not limited to improved survival rate or more rapid recovery, or improvement or attenuation or prevention of symptoms and other indicators as are selected as appropriate measures by those skilled in the art. The compounds disclosed herein can be administered by any of the conventional routes of administration. It should be noted that the compound can be administered as the compound or as pharmaceutically acceptable salt and can be administered alone or as an active ingredient in combination with pharmaceutically acceptable carriers, solvents, diluents, excipients, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. Liquid forms may be prepared for injection, the term including subcutaneous, transdermal, intravenous, intramuscular, intrathecal, and other parental routes of administration. The liquid compositions include aqueous solutions, with and without organic cosolvents, aqueous or oil suspensions, emulsions with edible oils, as well as similar pharmaceutical vehicles. In addition, under certain circumstances the compositions for use in the novel treatments of the present invention may be formed as aerosols, for intranasal and like administration. The patient being treated is a warm-blooded animal and, in particular, mammals including man. The pharmaceutically acceptable carriers, solvents, diluents, excipients, adjuvants and vehicles as well as implant carriers generally refer to inert, non-toxic solid or liquid fillers, diluents or encapsulating material not reacting with the active ingredients of the invention and they include liposomes, lipidated glycosaminoglycans and microspheres. Many such implants, delivery systems, and modules are well known to those skilled in the art.

The invention has been described in an illustrative manner, and it is to be understood that the terminology which has been used is intended to be in the nature of words of description rather than of limitation.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Example 1: Ischemia-Reperfusion Induced p53 Activation in Kidneys from Rat Donors Kidneys were harvested from young (3-month old) and old (14-month old) SD rats (n=4-6) and subjected to cold ischemia (CI) for 5 hours. One kidney from each animal was processed for protein extraction whereas the second kidney was transplanted into 3-month old syngeneic rats. The transplanted kidneys were harvested 24 hours after the surgery and the resultant onset of ischemia-reperfusion injury (IR) and also processed for protein extraction. Protein extracts were analyzed in ELISA for p53 expression levels.

Results: In FIG. 1, the Y-axis shows arbitrary units corresponding to p53 protein levels measured in ELISA. FIG. 1 shows that the p53 protein level is significantly increased in transplanted kidneys from older rats, compared to transplanted kidneys from young rats (3 months old). Note that following p53 activation occurring via a variety of post-translational modifications, its steady-state levels are increased due to marked protein stabilization.

Example 2: Use of an Inhibitor of a p53 Gene for Prophylaxis of Ischemic Reperfusion Injury (IRI) and Delayed Graft Function (DGF) in a Kidney Transplantation Recipient A placebo-controlled, randomized, prospective, double-blind, multicenter, phase II, dose-escalation study of the clinical activity of QPI-1002 (10 mg/kg single bolus IV dose given at 30 minutes after the reperfusion) for prophylaxis of delayed graft function in ESRD dialysis-dependent patients undergoing deceased donor kidney transplantation as well as the safety and PK of QPI-1002 in these patients.

The primary objectives of the study were 1) to assess the efficacy of QPI-1002 in the prevention of DGF and 2) to further assess the safety of a single-dose IV bolus infusion of QPI-1002 in high-risk patients following deceased donor renal transplantation.

Materials and Methods

Test product: QPI-1002 was provided by Quark Pharmaceuticals Inc., Fremont Calif., formulated as a preservative free, sterile solution formulated in phosphate buffered saline. The product was filled into clear Type I glass vials sealed with Teflon-coated butyl rubber stoppers with aluminum flip-off overseals. Each vial was provided for single use. Vials were stored at 2-8° C., protected from light. The solution was warmed to room temperature prior to use.

QPI-1002 was administered via bolus intravenous injection at a dose of 10 mg/kg at about 30 minutes following completion of surgery and removal of the patient from the cardiopulmonary bypass machine, or following reperfusion of the transplanted kidney.

Cold storage: Following removal from the donor, kidneys preserved by cold storage were flushed with cold preservative solution and placed in a sterile bag immersed in the solution. The sterile bag was placed inside an additional bag containing crushed ice.

Machine-perfusion: Following removal from the donor, kidneys preserved by machine-perfusion were connected to a perfusion device configured to continuously pump perfusion fluid through the organ. non-limiting examples of commonly used devices for machine perfusion of donor kidneys include the Waters RM3 (IGL/Waters Medical Systems, Rochester Minn.) and the LifePort kidney transporter (Organ Recovery Systems, des Plaines, Ill., USA). Non-limiting examples of suitable preservation solutions include UW (University of Wisconsin) solution and HTK (histidine-tryptophan-ketoglutarate) solution. During machine perfusion, the perfusion pressure was monitored and verapamil administered as required to vasodilate the kidney.

Patients: After obtaining written, informed consent, 332 patients scheduled for DDRT were randomized 1:1 to receive either a single IV dose of QPI-1002, 10.0 mg/kg or isotonic saline placebo (0.9% NaCl) in double-blind fashion, intraoperatively following allograft reperfusion (establishment of blood flow of the transplanted kidney). 331 patients received study drug (QPI-1002 or Placebo). Due to a pharmacy dispensing error, one patient did not receive a study drug.

The following table provides details of patient analysis sets:

TABLE A

| Analysis Sets | |
|---|---|
| ITT (Intent-to-treat): | All patients randomized, transplanted and dosed, analyzed as randomized |
| ITTEE: | Efficacy evaluable (EE) patients: All patients randomized, transplanted and dosed, analyzed as randomized, (excludes four patients who experienced graft loss in first 24 hrs post-transplant and one patient who did not receive study drug) - this population was used in the analysis of the primary efficacy endpoint |
| MITT (Modified intent-to-treat): | Same as ITT but analyzed as treated - this population was used in safety analysis |
| mITT(EE): | Same as ITTEE but analyzed as treated - this population was used in efficacy analysis (secondary endpoints) |

The primary endpoint was the incidence of DGF, whereas DGF was defined in the protocol as the necessity for dialysis during the first 7 days following the transplantation. The secondary endpoints included parameters measuring dialysis severity in dialyzed patients, kidney function in non-dialyzed patients immediately post-transplant (within 5 days) as well as kidney function at an intermediate-term observation point, i.e. at 30 days after transplantation.

Key eligibility criteria were designed to enroll patients scheduled to receive kidney transplant from a deceased donor in 4 subgroups formed based on the protocol-specified donor type and preservation modality (entirely cold-stored (CS) or at least partially machine-perfused (MP)):

ECD/CS: ECD kidney that has been preserved by cold storage for the entire period of cold ischemia time (CIT), regardless of duration ECD/MP: ECD kidney that has been preserved by machine perfusion for any interval of time during the period of cold ischemia, where total CIT has been at least 26 hours SCD/SCD kidney that has been preserved by cold storage where total CIT has been at least 26 hours SCD kidney that has been preserved by machine perfusion for any interval of time during the period of cold ischemia, where total CIT has been at least 26 hours.

Thus, estimated CIT duration did not limit study eligibility in the ECD/CS patients study group (Entirely cold stored ECD kidneys). Estimated CIT duration did limit eligibility (≥26 hours) in the other patient study groups:

The following table provides stratification results for efficacy analysis:

TABLE B

Stratification Results for Efficacy Analysis

| Strata % of mITT(EE) | ITT 332 patients | mITT(EE) 327 patients | ITTEE 327 patients |
|---|---|---|---|
| Overall 100% | 167 Placebo | 163 Placebo | 165 Placebo |
| | 165 QPI-1002 | 164 QPI-1002 | 162 QPI-1002 |
| ECD/CS 54.4% | 91 Placebo | 88 Placebo | 89 Placebo |
| | 90 QPI-1002 | 90 QPI-1002 | 88 QPI-1002 |
| ECD/MP 11.6% | 18 Placebo | 19 Placebo | 18 Placebo |
| | 20 QPI-1002 | 19 QPI-1002 | 20 QPI-1002 |
| SCD/CS 11.6% | 21 Placebo | 21 Placebo | 21 Placebo |
| | 19 QPI-1002 | 17 QPI-1002 | 19 QPI-1002 |
| SCD/MP 22.4% | 37 Placebo | 35 Placebo | 37 Placebo |
| | 36 QPI-1002 | 38 QPI-1002 | 35 QPI-1002 |

It should be noted that organ donor type was not accurately identified until transplant, hence at time of randomization, final organ type was not identified. As can be seen from Table B, ECD/CS was largest stratum (N=178 (mITT (EE)), with more than 50% of patients included in this stratum. ITT & ITTEE strata are presented in Table B as organ donor type (ECD/SCD) used in randomization. mITT (EE) stratum is presented in Table B as per actual organ donor type (ECD/SCD).

The age of the donors was as detailed in following Table C:

TABLE C

Donor Age

| Age (yrs); mean (range) | Donor | |
|---|---|---|
| | QPI-1002 | Placebo |
| Overall Population | 53.9 (12-84) | 53.6 (9-86) |
| SCD/CS CIT >26 hrs | 38.1 (12-56) | 38.4 (9-59) |
| SCD/MP CIT >26 hrs | 37.1 (12-59) | 38.0 (16-59) |
| ECD/CS | 62.9 (50-84) | 62.4 (51-86) |
| ECD/MP CIT >26 hrs | 58.5 (50-74) | 58.8 (51-69) |

DGF was defined as the need for dialysis within 24 hours following kidney transfer (excluding for hyperkalemia and/or hypervolemia).

Among 327 efficacy-evaluable patients (162 QPI-1002; 165 Placebo), the mean ages were 58.9 and 59.1 yrs, respectively; 64.8% and 68.5%, were male, 23.5% and 22.4% were black (p=ns). There were no significant treatment differences based on recipient weight, body mass index (BMI), peak pre-transfer % panel reactive antibody (PRA), prior transfusion status or HLA mismatching. The pre-transfer DGF risk, determined per Irish nomogram (2010), was 35-36% in both groups (p=ns). Among donors, ~⅔ were ECD and ⅓ SCD in each group; mean CIT and terminal serum creatinine, % with hypertension and cause of death were not significantly different between groups.

Detailed description of recipient and donor demographics is provided in the following Table D:

TABLE D

Stratification Results for Efficacy Analysis

| | Recipients | | Donors | |
|---|---|---|---|---|
| | QPI-1002 | Placebo | QPI-1002 | Placebo |
| Age (yrs); mean (range) | 58.9 (24-85) | 59.1 (23-83) | 53.9 (12-84) | 53.6 (9-86) |
| Sex (% male) | 64.8 | 68.5 | 58.0 | 52.1 |
| Race (% black) | 23.5 | 22.4 | 11.7 | 9.7 |
| Weight*, kg; mean (range) | 79.4 | 79.2 | 80.8 (20.79) | 82.7 (21.11) |
| BMI**, kg/m²; mean (SD) | 27.6 (4.93) | 27.6 (4.36) | — | — |
| Prior blood transfusion, n (%) | 64 (39.8) | 63 (38.2) | — | — |
| Peak % PRA***, mean (range) | 16.9 (0-100) | 14.2 (0-99) | — | — |
| Donor/recipient HLA mismatches, mean (range) | 4.4 (0-6) | 4.4 (0-6) | — | — |

*Weight: Recipient weight at Screening evaluation;
**BMI: Body mass index
***PRA: Panel reactive antibodies Table E provides non-demographic donor DGF risk variables:

TABLE E

Non-Demographic Donor DGF Risk Variables

| | Donor | |
|---|---|---|
| | QPI-1002 | Placebo |
| Donor type: | (N = 162) | (N = 165) |
| ECD, n (%) | 108 (66.7) | 108 (65.5) |
| SCD, n (%) | 54 (33.3) | 57 (34.5) |
| Cold ischemia time, hrs, mean (range) | 22.6 (3-65) | 23 (5-59) |
| Terminal Scr*, mg/dL; mean (SD) | (N = 159) | (N = 165) |
| | 1.2 (0.84) | 1.3 (0.95) |

TABLE E-continued

Non-Demographic Donor DGF Risk Variables

|  | Donor | |
|---|---|---|
|  | QPI-1002 | Placebo |
| History of hypertension, n (%) | (N = 162) | (N = 165) |
|  | 85 (52.5) | 90 (54.5) |
| Cause of death | (N = 112) | (N = 114) |
| Anoxia | 30 (26.8) | 29 (25.4) |
| CVA/stroke | 80 (71.4) | 84 (73.7) |
| Cardiac | 2 (1.8) | 1 (0.9) |
| DGF risk probability, mean (SD) | (N = 162) | (N = 165) |
|  | 0.35 (0.16) | 0.36 (0.18) |

In Table E:
*Scr: serum creatinine concentration;
*PRA: Panel reactive antibodies.

Results

Efficacy Endpoints: The primary endpoint of the study was the incidence of Delayed Graft Function (DGF) in the Intention-to-Treat (ITT) population of all randomized and transplanted patients, where DGF was defined as the need for dialysis initiated within the first 7 days post-transplant excluding the following:
(i) Dialysis performed during the first 24 hours for one or more of the following reasons:
 Treatment of hyperkalemia or hypervolemia
 Hyperacute rejection or other antibody-mediated acute rejection (biopsy confirmed)
 Technical vascular complications involving the allograft: renal arterial and/or venous thrombosis due to vascular injury or technical surgical complications.
(ii) Dialysis performed during the first 7 days post-transplant for one or more of the following reasons:
 Obstructive uropathy (Radiographically confirmed)
 Fulminant recurrence of primary disease (underlying etiology of ESRD, biopsy confirmed), including focal segmental glomerulosclerosis
 A specific diagnosis of thrombotic microangiopathy (Thrombotic Thrombocytopenic Purpura or Hemolytic-Uremic Syndrome, biopsy confirmed).

In addition to the primary endpoint, the following key exploratory efficacy endpoints were also evaluated:
1. The incidence of DGF in the modified Intention-to-Treat ((mITT)(EE)) population of all randomized and transplanted patients who received study drug, where DGF was defined as the need for acute dialysis within the first 7 days post-transplant excluding the following:
 Dialysis performed during the first 24 hours for one or more of the following reasons:
 Treatment of hyperkalemia or hypervolemia
 Hyperacute rejection or other antibody-mediated acute rejection (biopsy confirmed)
 Technical vascular complications involving the allograft: renal arterial and/or venous thrombosis due to vascular injury or technical surgical complications
 Dialysis performed during the first 7 days post-transplant for one or more of the following reasons:
 Obstructive uropathy (Radiographically-confirmed)
 Fulminant recurrence of primary disease (underlying etiology of ESRD), including focal segmental glomerulosclerosis
 A specific diagnosis of thrombotic microangiopathy (Thrombotic Thrombocytopenic Purpura or Hemolytic-Uremic Syndrome, biopsy confirmed)

2. Treatment differences in the rate of improvement in renal function over time
3. Treatment differences in the need for renal replacement therapy.

As defined, DGF occurred in 50 (30.9%) and 60 (36.4%) of QPI-1002 and placebo patients, respectively (p=0.349), a 15.1% relative reduction in DGF risk. In the largest patient group (ECD/CS, n=178), DGF rates were 27.9% and 39.3% for QPI-1002 vs. placebo, respectively, a clinically meaningful 30.7% relative reduction (p=0.111). The probability of remaining dialysis free time-to-first post-transplant dialysis was significantly longer improved for QPI-1002 (log-rank p=0.045) and the mean duration of dialysis was numerically shorter in this stratum (3.5 vs. 9.0 days for QPI-1002 vs. placebo, respectively, p=0.097). The overall safety profile of the drug was consistent with that expected among DDRT recipients during the early post-transplant period, and similar in both treatment groups.

Table F provides primary efficacy endpoint results in ITTEE population (Analyzed as randomized):

TABLE F

Primary Efficacy Endpoint (ITTEE population)

|  | QPI-1002 | | Placebo | | Relative Risk |
|---|---|---|---|---|---|
| Strata | N | DGF n (%) | N | DGF n (%) | Reduction (%) |
| Overall | 162 | 50 (30.86) | 165 | 60 (36.36) | −15.12 |
| SCD/CS | 19 | 7 (36.84) | 21 | 7 (33.33) | 10.53 |
| CIT > 26 h |  |  |  |  |  |
| SCD/MP | 35 | 11 (31.43) | 37 | 10 (27.03) | 16.29 |
| CIT > 26 h |  |  |  |  |  |
| ECD/CS | 88 | 24 (27.27) | 89 | 35 (39.33) | −30.65 |
| ECD/MP | 20 | 8 (40.00) | 18 | 8 (44.44) | −10 |
| CIT > 26 h |  |  |  |  |  |

Results for secondary endpoint dialysis received any time during first 7 days post-transplant (UNOS definition) in ITTEE population and in ECD/CS stratum are provided in the following Table G:

TABLE G

Secondary Endpoint DGF (UNOS Definition) (ITTEE population)

| ITTEE population overall (N = 327) | | | ECD/CS stratum only (N = 178) | | |
|---|---|---|---|---|---|
|  | DGF | |  | DGF | |
|  | N | % |  | N | % |
| QPI-1002 (n = 164) | 62 | 37.80 | QPI-1002 (n = 90) | 32 | 35.56 |
| Placebo (n = 163) | 76 | 46.63 | Placebo (n = 88) | 43 | 48.86 |
| Relative Reduction (%) |  | −18.9 | Relative Reduction (%) |  | −27.2 |
| Risk difference (95% CI) |  | −8.82 (−19.49, 1.84) | Risk difference (95% CI) |  | −13.31 (−27.69, 1.08) |
| Fisher's Exact p-value |  | 0.1176 | Fisher's Exact p-value |  | 0.0947 |

Figure 2A:
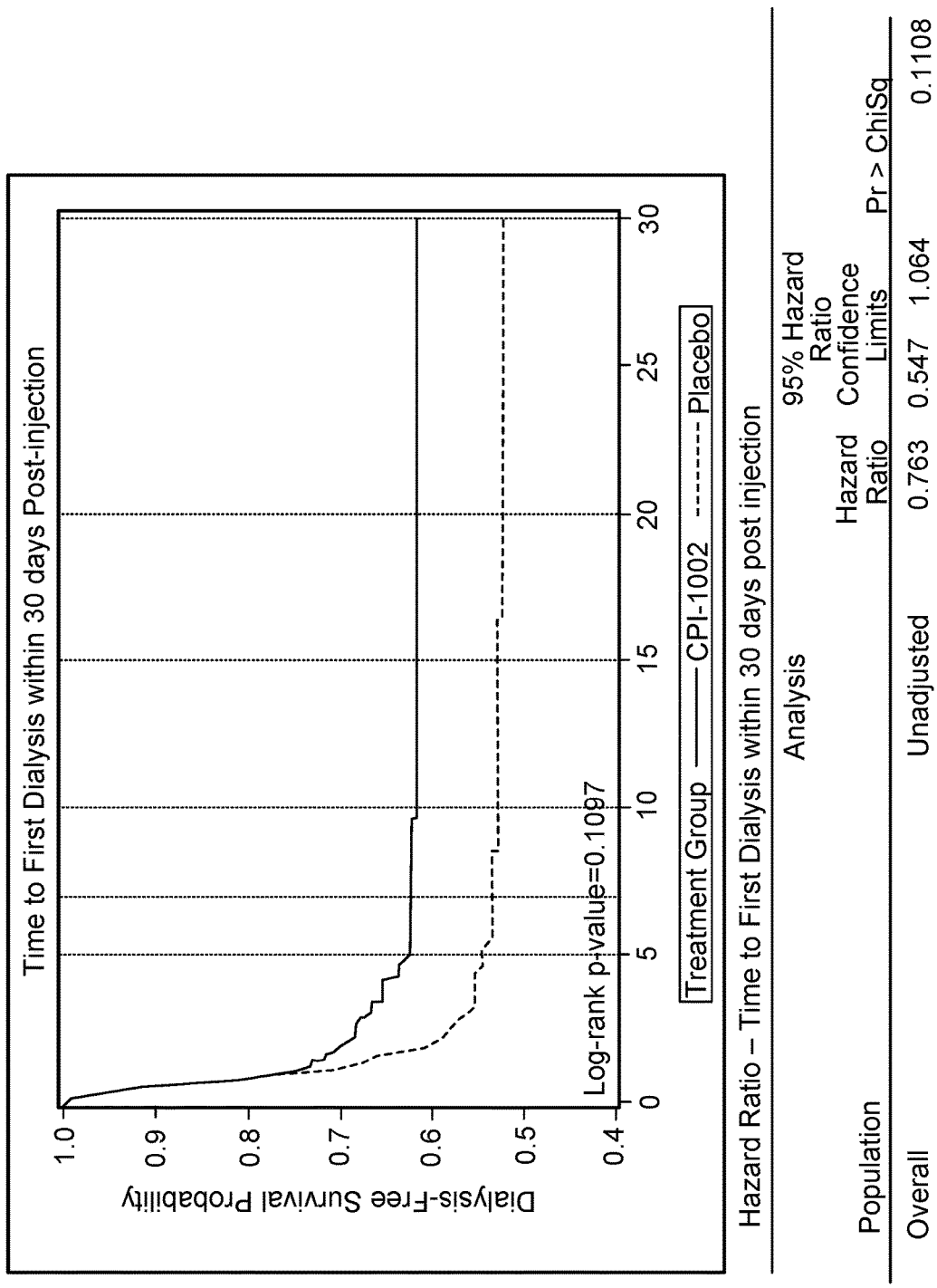
FIGS. 2a and 2b are line graphs showing secondary endpoint time to first post-transplant dialysis in mITT(EE) population (FIG. 2a) and in ECD/CS stratum (FIG. 2b).
Figure 2B:
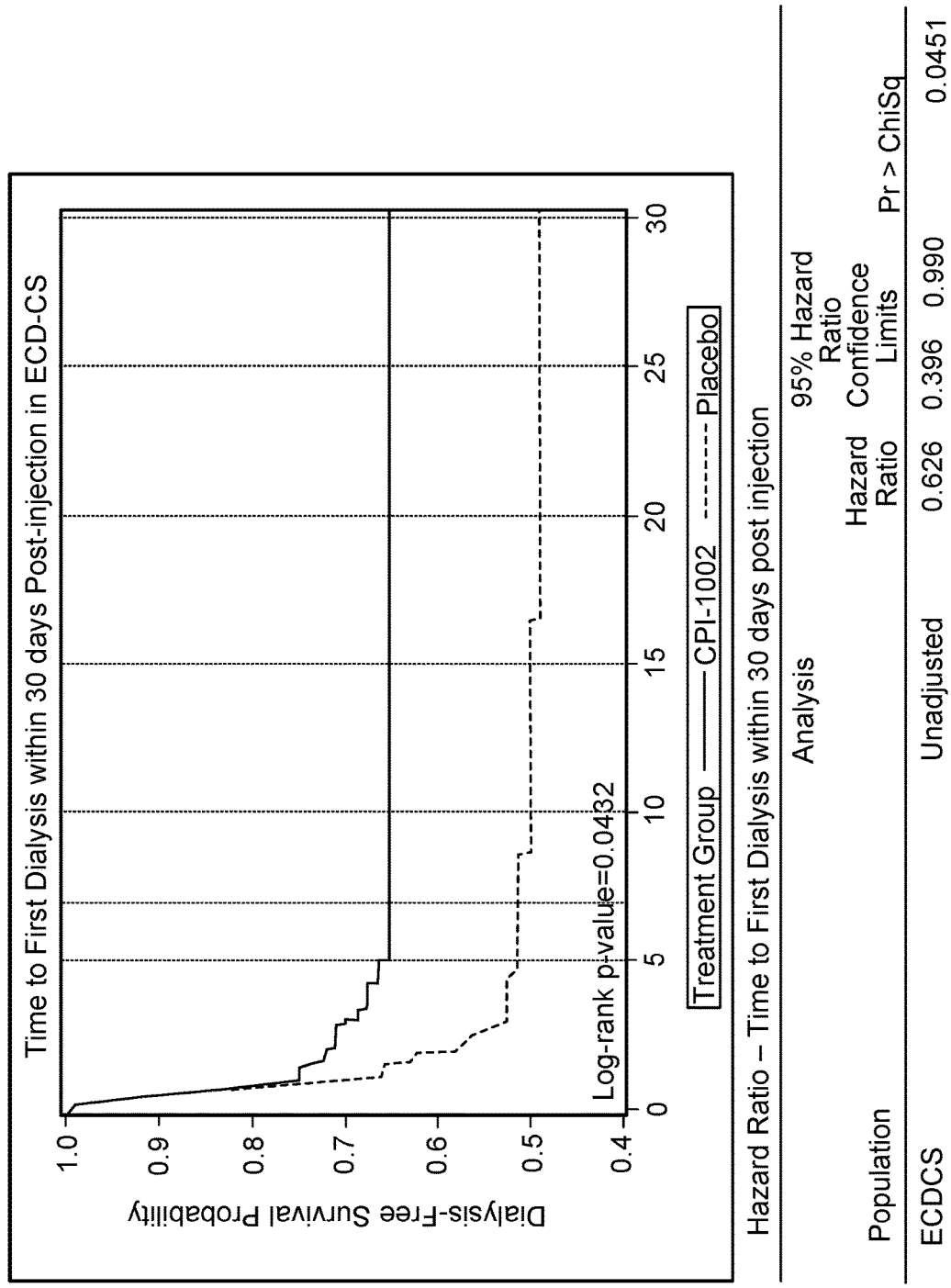

FIGS. 2a and 2b provide results for secondary endpoint probability of remaining dialysis free time to first post-transplant dialysis in mITT(EE) population (FIG. 2a) and in ECD/CS stratum (FIG. 2b), showing a greater reduction improvement in ECD/CS population treated with QP1-1002 as compared to the overall population.

Results for secondary endpoint duration of the initial post-transplant course of dialysis in all patients and in ECD/CS stratum are provided in the following Table H:

TABLE H

Secondary Endpoint Duration of the Initial Post-Transplant Course of Dialysis

|  | QPI-1002 | | Placebo | | | |
|---|---|---|---|---|---|---|
|  | N | Duration (days) Mean (SD) | N | Duration (days) Mean (SD) | Relative Reduction (%) | P-value* |
| All patients** | 51 | 14.1 (27.75) | 59 | 16.9 (30.91) | −17 | 0.620 |
| ECD/CS*** stratum | 26 | 13.40 (34.43) | 34 | 21.06 (39.61) | −36 | 0.436 |

*P-value: (Unpaired t-test)
**All patients who received a course of dialysis that began during the first post-transplant week
***All ECD/CS patients who received a course of dialysis that began during the first post-transplant week Table H shows that clinically significant reduction of more than 30% was achieved in ECD/CS stratum, such that on average one week of dialysis was saved in patients receiving QPI-1002.

Additional secondary efficacy endpoint was incidence of achieving an eGFR>10 mL/min/1.73 m2 for at least 3 of 7 days during the first post-transplant week (non dialysis-based DGF definition). Results are provided in Table I.

TABLE I

Post-transplant Recovery of Renal Function. Incidence of Decrease in Serum Creatinine ≥10%/day for ≥3 of First 7 Days.

|  | QPI-1002 (n = 107)* | Placebo (n = 92)* | Relative Drug Effect (%) | Fisher's Exact P-value |
|---|---|---|---|---|
| All patients n (%) | 63 (58.9) | 52 (56.5) | 4.2 | 0.775 |
|  | (n = 58)* | (n = 50)* | | |

TABLE I-continued

Post-transplant Recovery of Renal Function. Incidence of Decrease in Serum Creatinine ≥10%/day for ≥3 of First 7 Days.

|  | QPI-1002 (n = 107)* | Placebo (n = 92)* | Relative Drug Effect (%) | Fisher's Exact P-value |
|---|---|---|---|---|
| ECD/CS n (%) | 34 (58.6) | 23 (46.0) | 27.4 | 0.247 |

*Analysis restricted to the serum creatinine concentrations of patients who were not receiving a course of dialysis (and had not received any dialysis for at least 48 hours).

Additional non-dialysis DGF secondary efficacy endpoint was slope of estimated GFR (eGFR) versus time post-transplant. Results are provided in Table J.

TABLE J

Non Dialysis DGF Secondary Efficacy Endpoint. Slope of Estimated GFR (eGFR) Versus Time Post-transplant.

|  | QPI-1002 | | Placebo | | | |
|---|---|---|---|---|---|---|
|  | N | eGFR slope*, mL/min/1.73 m²/day; mean (SD) | N | eGFR slope*, mL/min/1.73 m²/day; mean (SD) | Relative Effect (%) | P-value |
| All patients | | | | | | |
| 4-variable MDRD equation | 164 | 2.7 (3.63) | 163 | 2.4 (3.45) | 12.5 | 0.587 |
| Cockroft-Gault equation | 155 | 2.6 (3.79) | 153 | 2.4 (4.18) | 8.3 | 0.701 |
| Nankivell equation "B" | 100 | 2.5 (4.01) | 100 | 2.6 (4.68) | −4.0 | 0.825 |
| ECD/CS patients | | | | | | |
| 4-variable MDRD equation | 90 | 2.6 (3.40) | 88 | 1.8 (2.88) | 44.4 | 0.065 |
| Cockroft-Gault equation | 84 | 2.6 (3.70) | 86 | 1.7 (3.23) | 52.9 | 0.081 |
| Nankivell equation "B" | 60 | 2.7 (4.14) | 64 | 2.4 (4.42) | 12.5 | 0.633 |

*eGFR: Calculated after censoring serum creatinine results obtained during or within 48 hrs of completion of any course of dialysis.

Additional non-dialysis DGF secondary efficacy endpoint was measured GFR at the day 30 study visit, determined with non-radiolabeled iothalamate, using a commercially available protocol (Mayo Clinic, Rochester Minn.), at North American sites only. Patients who were dialysis dependent within 48 hours of the Day 30 visit and those with any history of allergy to shellfish or iodinated radiocontrast were also excluded from participation in this assay. Results are provided in Table K.

TABLE K

Non Dialysis DGF Secondary Efficacy Endpoint. Post-transplant Recovery of Renal Function Measured GFR at the Day 30 Study Visit

| | ITTEE population overall (N = 327) | | | ECD/CS stratum only (N = 178) | | |
|---|---|---|---|---|---|---|
| | | DGF | | | DGF | |
| | N | mGFR mean (SD) | | N | mGFR mean (SD) | |
| QPI-1002 (n = 164) | 62 | 33.8 (31.96) | QPI-1002 (n = 90) | 30 | 34.8 | |
| Placebo (n = 163) Absolute GFR | 76 | 29.3 (28.13) 4.54 | Placebo (n = 88) Absolute GFR | 36 | 21.1 13.72 | |
| difference (95% CI) | | (−5.58, 14.67) | difference (95% CI) | | (1.02, 26.41) | |
| Fisher's Exact p-value | | 0.376 | Fisher's Exact p-value | | 0.035 | |

An additional non-dialysis DGF secondary efficacy endpoint was urine output between 2 and 3 days post-transplant, as determined from the protocol-specified, Day 2-Day 3 quantitated urine output; the total volume reported was normalized to that of a 24-hour collection for each patient. Analysis excluded results from all patients who received, or were still receiving dialysis at any time post-transplant through the end of the (Day 2-Day 3) urine collection period. Results are provided in Table L.

TABLE L

Non Dialysis DGF Secondary Efficacy Endpoint. Urine Output Between 2 and 3 Days Post-transplant

| | QPI-1002 | | Placebo | | | |
|---|---|---|---|---|---|---|
| | N | Day 2-Day 3 urine output (# patients >500 ml/day); mean (SD) | N | Day 2-Day 3 urine output (# patients >500 ml/day) mean (SD) | Relative Effect (%) | P-value |
| All patients | 80 | 71 (88.8) | 79 | 62 (78.5) | 13.1 | 0.090 |
| All ECD/CS patients | 40 | 37 (92.5) | 41 | 28 (68.3) | 35.4 | 0.011 |

Additional non-dialysis DGF secondary efficacy endpoint was based on treatment differences in the percentages of subjects with DGF, SGF and IGF, as defined per the criteria of Humar et al (Clinical Transplantation, 2002) and Johnston et al (NDT, 2006). Results are provided in Table M and the data suggest a shift from DGF to slow graft function (SGF) in QPI-1002 treated group.

TABLE M

Non Dialysis DGF Secondary Efficacy Endpoint. Incidence of Delayed, Slow and Immediate Graft Function (EGF, SGF and IGF).

| Event Subset | QPI-1002 (N = 164) | Placebo (N = 163) | Overall (N = 327) | P-value, unadjusted [2] | Adjusted Odds Ratio [3] |
|---|---|---|---|---|---|
| Humar et al. | | | | | |
| All patients | (n = 133) | (n = 134) | (n = 267) | | |
| IGF | 36 (27.1) | 36 (26.9) | 72 (27.0) | 0.112 | 0.8 (0.5, 1.2) |
| SGF | 35 (26.3) | 22 (16.4) | 57 (21.3) | | |
| DGF | 62 (46.6) | 76 (56.7) | 138 (51.7) | | |
| Johnston et al | | | | | |
| All patients | (n = 132) | (n = 136) | (n = 268) | | |
| IGF | 31 (23.5) | 33 (24.3) | 64 (23.9) | 0.167 | 0.8 (0.5, 1.3) |
| SGF | 39 (29.5) | 27 (19.9) | 66 (24.6) | | |
| DGF | 62 (47.0) | 76 (55.9) | 138 (51.5) | | |

Age Defined Limitations

Figure 3:
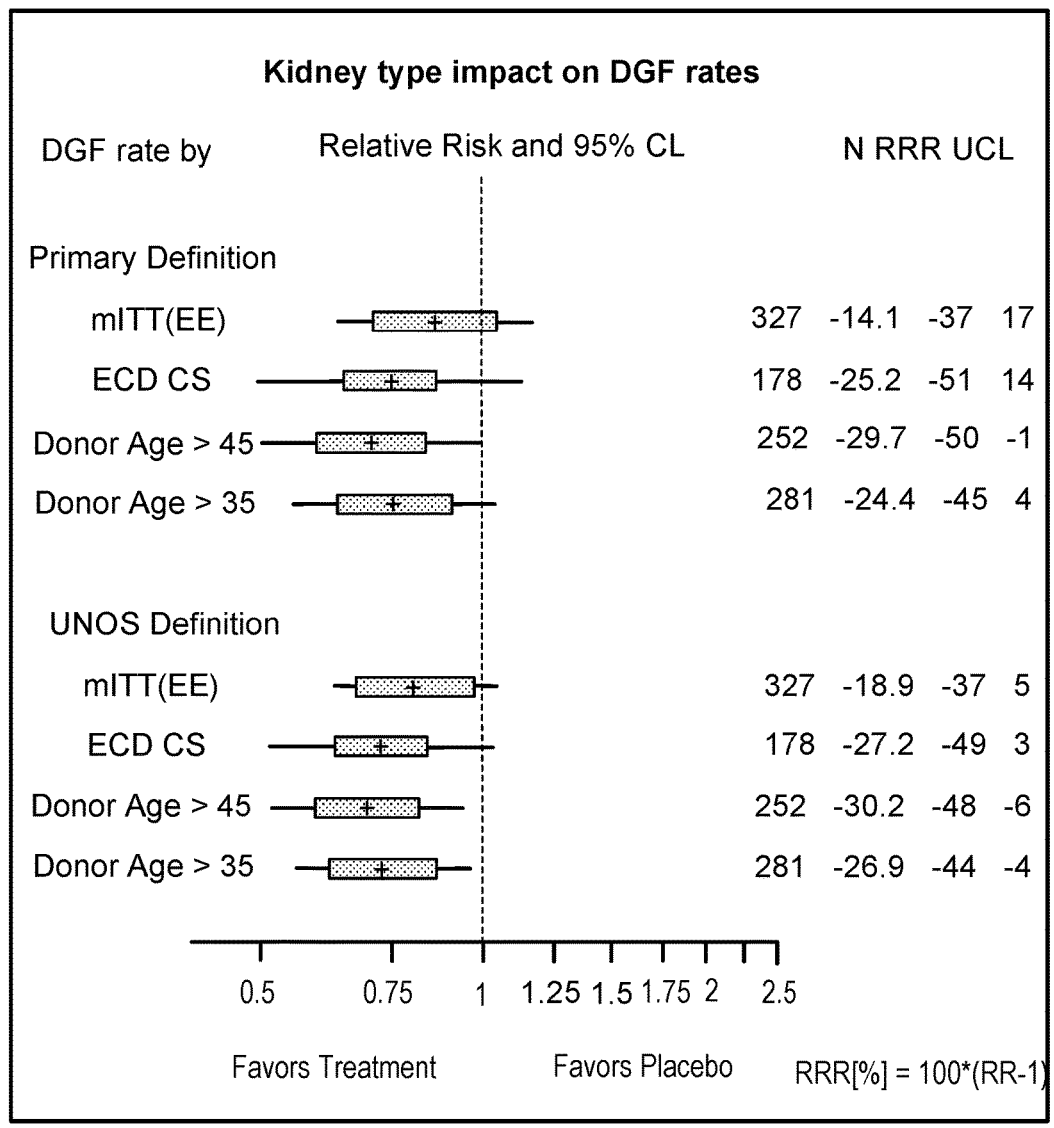
FIG. 3 shows a Forest plot demonstrating the impact of QPI-1002 treatment on DGF relative risk reduction in graft recipients per donor kidney type.

Primary Efficacy End-Point:

The primary protocol definition-based and UNOS definition-based DGF results (relative risks and 95% confidence intervals) in the overall mITT(EE) population, the pre-specified ECD/CS stratum and in patients receiving kidneys from donors older than 45 or older than 35 years of age are shown in FIG. 3. FIG. 3 shows a Forest plot demonstrating the impact of QPI-1002 treatment on DGF relative risk reduction in graft recipients per donor kidney type. Relative risk (RR) is calculated as the ratio between DGF incidence in QPI-1002-treated patients and placebo-treated patients in a given patient subgroup. Box plots: Estimated RR values are marked with "+" inside the boxes. Box sizes are proportional to respective sample sizes. Line ends represent respective calculated RR 95% confidence limits (CL). Other definitions: N—number of patients in a given subgroup. RRR—relative risk reduction (%) calculated as RRR (%)=100*(RR-1). LCL—95% lower confidence limit of RRR. UCL—95% upper confidence limit of RRR.

The strongest drug effect was observed in patients receiving kidneys from donors older than 45 years of age (n=252; 77% of all evaluable patients in this study regardless of subgroup attribution) where QPI-1002 reduced the incidence of DGF by about −30% relative to placebo. The results were the same when either the primary definition of DGF in this protocol or the widely accepted UNOS definition was used. This −30% difference was both statistically significant (protocol-defined DGF–p=0.048; UNOS DGF definition–p=0.016) and clinically meaningful. Furthermore, when the donor age threshold was lowered to 35 years (n=281; 86% of all evaluable patients in this study regardless of subgroup attribution), QPI-1002 still retained its ability to reduce the DGF rate by relative −27%, a clinically and statistically significant difference (UNOS definition of DGF, p=0.023).

These results are compatible with the new OPTN UNOS classification, which are designed to replace the previous ECD, SCD, DCD classification.

Secondary Efficacy Endpoint:

The impact of QPI-1002 on the severity of DGF was evaluated by looking at duration (in days) of the initial course of dialysis and intensity (in number of sessions) of dialysis in the first 30 days post-transplant. For both parameters, QPI-1002 produced numerically superior results in the overall mITT(EE) population (n=110), and in the subgroups of patients receiving ECD/CS kidneys (n=60) or in patients receiving kidneys from older donors at either 45 (n=88) or 35 (n=101) year of age thresholds. Specifically, in dialyzed QPI-1002-treated patients receiving ECD/CS kidneys both the duration and the intensity of dialysis were shorter by −46% relative to the placebo group. In the dialyzed patients receiving older kidneys (whether from donors older than 45 or 35 years of age) as well as in the overall patient population these reductions ranged from −26% to −33%%.

The impact of QPI-1002 on kidney function in the immediate post-transplant period (5 days) in non-dialyzed patients was evaluated by measuring urine output as well as creatinine-based parameters related to glomerular function, i.e. eGFR and serum creatinine concentration. The number of patients in whom urine output was greater than 500 ml from day 2 to day 3 post-transplant was 35% higher among QPI-1002-treated ECD/CS patients when compared to the placebo group (n=81; p=0.011). Among patients receiving kidneys from older donors, the corresponding percentage increases associated with QPI-1002 treatment were 18% and 20% for donor age thresholds of 35 (n=132) and 45 (n=118) years of age, respectively.

Tables 3a, 3b and 3c show endpoint data for overall recipient population, population of recipients who received a kidney from a donor 45 years old and older; and population of recipients who received a kidney from a donor 35 years old and older. "Duration of DGF" (ie., the total number of contiguous days counted from the DGF Start date to the DGF Stop date).

TABLE 3a

| | Overall Population | | | | |
|---|---|---|---|---|---|
| Endpoint | Placebo (N = 163) | QPI-1002 (N = 164) | Absolute Difference | Relative Difference | p-value |
| DGF (Primary Endpoint) | N = 163 | N = 164 | | | |
| Percent | 36.2% | 31.1% | −5.1 | −14.09% | 0.351 |
| DGF (UNOS) | N = 163 | N = 164 | | | |
| Percent | 46.6% | 37.8% | −8.8 | −18.88% | 0.118 |
| Duration of DGF | N = 59 | N = 51 | | | |
| Mean Days (SD) | 19.2 (36.9) | 14.1 (27.8) | −5.13 | −26.72% | 0.417 |
| Intensity of Dialysis | N = 59 | N = 51 | | | |
| Mean Dialysis Sessions (SD) | 8.7 (15.7) | 6.2 (11.8) | −2.48 | −28.51% | 0.356 |
| 24 hr Urine Output >500 ml between Day 2 and Day 3 Percent | N = 79 78.5% | N = 80 88.8% | 10.3 | 13.12% | 0.090 |
| eGFR Slope Cockroft-Gault | N = 153 | N = 155 | | | |
| Mean Coefficient (SD) | 2.4 (4.2) | 2.6 (3.8) | 0.17 | 7.08% | 0.701 |
| eGFR Slope (MDRD) | N = 163 | N = 164 | | | |
| Mean Coefficient (SD) | 2.4 (3.5) | 2.7 (3.6) | 0.21 | 8.75% | 0.587 |
| eGFR Slope Nankivell | N = 100 | N = 100 | | | |
| Mean Coefficient (SD) | 2.6 (4.7) | 2.5 (4.0) | −0.14 | −5.38% | 0.825 |
| eGFR Day 30 Cockroft-Gault | N = 127 | N = 116 | | | |
| Mean (SD) | 42.3 (20.1) | 45.7 (20.2) | 3.46 | 8.18% | 0.183 |
| eGFR Day 30 MDRD | N = 151 | N = 146 | | | |
| Mean (SD) | 41.4 (20.7) | 42.2 (21.2) | 0.83 | 2.00% | 0.734 |
| eGFR Day 30 Nankivell | N = 127 | N = 116 | | | |
| Mean (SD) | 53.3 (23.2) | 56.9 (22.2) | 3.54 | 6.64% | 0.226 |
| mGFR Day 30 | N = 76 | N = 62 | | | |
| Mean (SD) | 42.6 (21.3) | 42.5 (26.5) | −0.13 | −0.31% | 0.974 |

TABLE 3b

| Endpoint | Placebo (N = 163) | QPI-1002 (N = 164) | Absolute Difference | Relative Difference | p-value |
|---|---|---|---|---|---|
| | >45 years of age |||||
| DGF (Primary Endpoint) | N = 127 | N = 125 | | | |
| Percent | 40.94 | 28.8 | −12.14 | −29.66% | 0.048 |
| DGF (UNOS) | N = 127 | N = 125 | | | |
| Percent | 50.39 | 35.2 | −15.19 | −30.15% | 0.016 |
| Duration of DGF | N = 52 | N = 36 | | | |
| Mean Days (SD) | 20.7 (39.0) | 14.3 (32.4) | −6.39 | −30.87% | 0.421 |
| Intensity of Dialysis | N = 52 | N = 36 | | | |
| Mean Dialysis Sessions (SD) | 9.3 (16.6) | 6.2 (13.8) | −3.10 | −33.3% | 0.359 |
| 24 hr Urine Output >500 ml | N = 60 | N = 58 | | | |
| between Day 2 and Day 3 Percent | 73.33 | 87.93 | 14.6 | 19.91% | 0.063 |
| eGFR Slope Cockroft-Gault | N = 121 | N = 117 | | | |
| Mean Coefficient (SD) | 2.0 (4.1) | 2.4 (3.6) | 0.40 | 20.0% | 0.421 |
| eGFR Slope (MDRD) | N = 127 | N = 125 | | | |
| Mean Coefficient (SD) | 2.0 (3.3) | 2.6 (3.6) | 0.65 | 32.5% | 0.136 |
| eGFR Slope Nankivell | N = 83 | N = 81 | | | |
| Mean Coefficient (SD) | 2.4 (4.6) | 2.6 (4.0) | 0.19 | 7.92% | 0.783 |
| eGFR Day 30 Cockroft-Gault | N = 101 | N = 89 | | | |
| Mean (SD) | 39.1 (20.4) | 42.9 (18.7) | 3.81 | 9.74% | 0.183 |
| eGFR Day 30 MDRD | N = 117 | N = 111 | | | |
| Mean (SD) | 37.2 (19.6) | 40.3 (19.9) | 3.12 | 8.39% | 0.235 |
| eGFR Day 30 Nankivell | N = 101 | N = 89 | | | |
| Mean (SD) | 50.2 (24.1) | 54.9 (21.8) | 4.72 | 8.4% | 0.161 |
| mGFR Day 30 | N = 56 | N = 47 | 1.87 | 4.77% | 0.663 |
| Mean (SD) | 39.2 (20.2) | 41.1 (23.2) | | | |

TABLE 3c

| Endpoint | Placebo (N = 163) | QPI-1002 (N = 164) | Absolute Difference | Relative Difference | p-value |
|---|---|---|---|---|---|
| | >35 years of age |||||
| DGF (Primary Endpoint) | N = 139 | N = 142 | | | |
| Percent | 41.01 | 30.99 | −10.02 | −24.44% | 0.084 |
| DGF (UNOS) | N = 139 | N = 142 | | | |
| Percent | 51.08 | 37.32 | −13.76 | −26.93% | 0.023 |
| Duration of DGF | N = 57 | N = 44 | | | |
| Mean Days (SD) | 19.6 (37.4) | 14.0 (29.6) | −5.59 | −28.52% | 0.419 |
| Intensity of Dialysis | N = 57 | N = 44 | | | |
| Mean Dialysis Sessions (SD) | 8.9 (15.9) | 6.2 (12.7) | −2.64 | −29.66% | 0.370 |
| 24 hr Urine Output >500 ml | N = 64 | N = 68 | | | |
| between Day 2 and Day 3 Percent | 73.44 | 86.76 | 13.32 | 18.14% | 0.079 |
| eGFR Slope Cockroft-Gault | N = 131 | N = 134 | | | |
| Mean Coefficient (SD) | 2.0 (4.2) | 2.5 (3.8) | 0.54 | 27.0% | 0.271 |
| eGFR Slope (MDRD) | N = 139 | N = 142 | | | |
| Mean Coefficient (SD) | 2.0 (3.3) | 2.7 (3.7) | 0.66 | 33.0% | 0.115 |
| eGFR Slope Nankivell | N = 90 | N = 87 | | | |
| Mean Coefficient (SD) | 2.3 (4.8) | 2.5 (4.0) | 0.20 | 8.70% | 0.767 |
| eGFR Day 30 Cockroft-Gault | N = 109 | N = 102 | | | |
| Mean (SD) | 40.1 (20.3) | 44.0 (19.2) | 3.92 | 9.78% | 0.152 |
| eGFR Day 30 MDRD | N = 129 | N = 126 | | | |
| Mean (SD) | 38.5 (19.7) | 40.4 (20.0) | 1.93 | 5.01% | 0.439 |
| eGFR Day 30 Nankivell | N = 109 | N = 102 | | | |
| Mean (SD) | 51.0 (23.7) | 55.4 (21.5) | 4.45 | 8.73% | 0.156 |
| mGFR Day 30 | N = 63 | N = 54 | | | |
| Mean (SD) | 41.0 (20.9) | 42.3 (27.6) | 1.33 | 3.24% | 0.768 |

Note that all day 30 GFR values in Tables 3a-3c are observed values and not change from baseline. Conclusions: The clinical benefit of the QPI-1002 in patients undergoing deceased donor renal transplantation with marginal kidneys increases with donor age.

The best primary endpoint results were obtained for patients receiving kidneys from donors older than 45 years of age, regardless of their primary subgroup classification (that constituted 77% of all the evaluable patients in the study). A threshold of 35 years of age (86% of all the evaluable patients in the study regardless of subgroup classification) yielded similar benefits, which are:

Clinically meaningful and, in some subgroups, statistically significant reduction in the incidence of dialysis in the first week post-transplant—the primary endpoint of this study.

Clinically meaningful reductions in the duration and intensity of dialysis in patients who experienced DGF.

Clinically meaningful increases in urine output and eGFR slope over time in the immediate post-transplant period in non-dialyzed patients; and, Clinically meaningful increase in day 30 eGFR.

Non Dialysis/Renal Function Recovery Efficacy Conclusions:

1. eGFR Slope over time. Overall population showed modest increase in the rate of eGFR improvement over time in QPI-1002 treated patients compared to Placebo treated patients. Whereas ECD/CS stratum showed a clinically significant increase (44% MDRD) in the rate of eGFR improvement over time in QPI-1002 treated patients compared with Placebo-treated patients (p=0.065 for the eGRF calculated by the MDRD equation).
2. mGRF at Day 30. Overall population showed 4.5 mL/min/1.73 m2 increase in mGFR for QPI-1002 treated patients vs. placebo. Whereas ECD/CS stratum showed a clinically and statistically increase of 13.72 mL/min/1.73 m2 in mGFR for QPI-1002 treated patients vs. placebo (p=0.035)
3. Urine output post transplantation. Overall population showed 13% increase in urine output in QPI-1002 patients vs. placebo (p=0.09). Whereas ECD/CS stratum showed 35% increase in urine output in QPI-1002 patients vs. placebo. (p=0.011).
4. A shift from DGF to SGF in QPI-1002 treated group.

Conclusion

The rate of DGF was numerically lower among QPI-1002 treated patients as compared to patients receiving placebo in the largest (ECD/CS) group and was accompanied by reduced need for post-transfer dialysis and a comparable safety profile among both treatment groups. Patients undergoing DDRT with entirely cold-stored ECD kidneys may benefit from intraoperative, post-reperfusion treatment with QPI-1002 in terms of reduced need for dialysis and higher GFRs at 1 month post-transfer.

Single-dose treatment with QPI-1002 following vascular reperfusion was associated with a safety profile similar to that of Placebo, and comparable to that expected among recipients of deceased donor renal transplants.

Overall, recipients of single-dose treatment with QPI-1002 demonstrated a 15% lower rate of DGF when compared to Placebo. This result was not statistically significant.

Among recipients of entirely cold-stored ECD kidneys, the largest stratum of study patients, a 30% treatment difference in the rate of DGF in favor of QPI-1002 approached statistical significance (p=0.11).

Secondary endpoint analyses demonstrated clinically significant beneficial treatment differences versus Placebo in the following endpoints:

Rate of DGF by the classical UNOS definition

Time to first dialysis

Severity of DGF: Duration and intensity eGFR Slope

Urine output 2-3 days post transplantation

Shift from DGF to SGF

For many of these secondary endpoints the results for recipients of entirely cold-stored ECD kidneys, the largest stratum of study, more closely approached (and in some cases achieved) statistical significance.

A potential pharmacoeconomic benefit was observed in the ECD/CS stratum in association with single-dose treatment with QPI-1002, in terms of:

A significantly higher probability of remaining dialysis free, as demonstrated by Kaplan-Meier analysis (log-rank p<0.05); and Fewer total dialysis treatments received during the first 30 days post-transplant (lower dialysis "intensity"), a difference that approached statistical significance (p<0.10).

Example 2: Use of an Inhibitor of a p53 Gene for Prophylaxis of Delayed Graft Function (DGF) in a Recipient of a Kidney from Donors of Various Ages A study similar to Example 1 was performed to test the effectiveness of QPI-1002 using kidneys from donors of various ages that did not necessarily meet the criteria for ECD donors.

In the efficacy analysis, the best primary endpoint results were obtained for patients receiving kidneys from donors older than 45 years of age (regardless of their primary subgroup classification) that constituted 77% of all the evaluable patients in the study). Importantly, a threshold of 35 years of age (86% of all the evaluable patients in the study regardless of subgroup classification) yielded similar benefits (listed below):

Clinically meaningful and, in some subgroups, statistically significant reduction in the incidence of dialysis in the first week post-transplant—the primary endpoint of this study.

Clinically meaningful reductions in the duration and intensity of dialysis in patients who experienced DGF.

Clinically meaningful increases in urine output and eGFR slope over time in the immediate post-transplant period in non-dialyzed patients; and, Clinically meaningful increase in day 30 eGFR Example 3: Dialysis Analysis in Phase II Study Objective: Dialysis has a pharmacoeconomic impact as well as health consequences. Therefore, a comparison of the number of dialyses from day 0 to day 180 between treatment groups is of interest.

Statistical Methods: to compare between treatment groups (I5NP, Placebo)
  Zero-inflated Poisson regression model (ZIP), which is a statistical model based on a Poisson probability distribution that allows for frequent zero-valued observations. The dialysis count per patient variable is of such nature.
  Sensitivity analysis: Non-parametric test: Wilcoxon and Median
  Descriptive statistics: using counts, mean, standard deviation (SD), median, minimum and maximum
  The analysis was not limited to the first course only or conditioned on DGF event.
  Analysis scheme: The analysis was performed on the mitt(EE) population.
    Over all patients
    Donor age >35 years patient group
    Donor age >45 years patient group
    Study duration analysis
    0-180 day and
      0-7 days
      7(+)-30 days
      30+

Technical (data) details: Dialysis data is drawn out from 'Dial' file. In general, in 'Dial' data set any record before day 30 is considered as a session and from day 30 and onward the record is regarded as a course which includes the start date and the end date. The number of dialyses in a course is calculated as follow: Number of Dialysis in a course=3* (Last date of the Course−Start date of a course)/7.

Results:
  Overall patients: Overall, 936 dialysis have been performed in the study. Their distribution according to time interval and overall are summarized in Table 4a:

TABLE 4a

Overall dialysis distribution and time intervals - total population
Overall

| Treatment | Count dialysis 0 < days <= 180 | Count dialysis 0 < days <= 7 | Count dialysis 7 < days <= 30 | Count dialysis day >30 |
|---|---|---|---|---|
| I5NP | 375 (40%) | 138 (44%) | 113 (41%) | 124 (36%) |
| Placebo | 561 (60%) | 178 (56%) | 162 (59%) | 221 (64%) |
| Total Dialysis | 936 | 316 | 275 | 345 |

Table 4b summarizes the mean, STD, min, max and median of the number of dialysis per patients for each treatment group. The most right hand side columns include the p-value obtained from the different tests for the treatment comparison.

TABLE 4b comparison of mean number of dialysis per patients
between treatment groups (Total population)
Overall: Count dialysis 0 < days <= 180

| Treatment | N | mean | std | min | median | max | MedianP | wilcoxonP |
|---|---|---|---|---|---|---|---|---|
| I5NP | 164 | 2.29 | 7.31 | 0 | 0 | 78 | 0.0857 | 0.112 |
| Placebo | 163 | 3.44 | 10.47 | 0 | 0 | 86 | | |

The mean number of dialysis per patients in I5NP group is 2.29, which is ~⅔ of the Placebo group (3.44). The p-value is 0.086 according to the median test.

The p-value obtained by the ZIP model is 0.014, which means that there is a significant reduction of the number of dialysis per patient in the I5NP group with respect to the Placebo group.

Donor Age >45 kidneys patients sub-population:
  Overall, 796 dialysis have been performed in the sub population of donor age kidneys >45 years. Their distribution according to time interval and overall are summarized in Table 4c:

TABLE 4c

Overall dialysis distribution and time intervals - Donor Age >45 population
Donor Age >45

| Treatment | Count dialysis 0 < days <= 180 | Count dialysis 0 < days <= 7 | Count dialysis 7 < days <= 30 | Count dialysis day >30 |
|---|---|---|---|---|
| I5NP | 269 (34%) | 93 (38%) | 65 (30%) | 111 (33%) |
| Placebo | 527 (66%) | 151 (62%) | 155 (70%) | 221 (67%) |
| Total Dialysis | 796 | 244 | 220 | 332 |

Table 4d contains the descriptive statistics for the mean number of dialysis per patients according to treatment groups.

TABLE 4d comparison of mean number of dialysis per patients
between treatment groups Donor Age > 45 population
Donor Age > 45: Count dialysis 0 < days <= 180

| Treatment | n | mean | std | min | median | max | MedianP | wilcoxonP |
|---|---|---|---|---|---|---|---|---|
| I5NP | 125 | 2.15 | 7.95 | 0 | 0 | 78 | 0.0076 | 0.0071 |
| Placebo | 127 | 4.15 | 11.74 | 0 | 1 | 86 | | |

The mean number of dialysis per patients in I5NP group is 2.15, which is ~½ of the Placebo group (4.14). The difference is statistically significant p-value is 0.0076 according to the median test.

The p-value obtained by the ZIP model is <0.01, which means that there is a significant reduction of the number of dialysis per patient in the I5NP group with respect to the Placebo group.

Donor Age >35 kidneys patients:
  Overall, 871 dialysis were performed in the sub population of donor age kidneys >35 years. Their distribution according to time interval and overall are summarized in Table 4e:

TABLE 4e

Overall dialysis distribution and time intervals - Donor Age >35 population
Donor Age >35

| Treatment | Count dialysis 0 < days <= 180 | Count dialysis 0 < days <= 7 | Count dialysis 7 < days <= 30 | Count dialysis day >30 |
|---|---|---|---|---|
| I5NP | 322 (37%) | 118 (41%) | 88 (35%) | 116 (34%) |
| Placebo | 549 (63%) | 168 (59%) | 160 (65%) | 221 (66%) |
| Total Dialysis | 871 | 286 | 248 | 337 |

Table 4f contains the descriptive statistics for the mean number of dialysis per patients according to treatment groups.

TABLE 4F comparison of mean number of dialysis per patients
between treatment groups Donor Age > 35 population
Donor Age > 35: Count dialysis 0 < days <= 180

| Treatment | n | mean | std | min | median | max | MedianP | wilcoxonP |
|---|---|---|---|---|---|---|---|---|
| I5NP | 142 | 2.27 | 7.63 | 0 | 0 | 78 | 0.0149 | 0.0186 |
| Placebo | 139 | 3.95 | 11.26 | 0 | 1 | 86 | | |

The mean number of dialysis per patients in I5NP group is 2.27, which is ~⅗ of the Placebo group result (3.95). The difference is statistically significant p-value is 0.0149 according to the median test.

The p-value obtained by the ZIP model is <0.01, which means that there is a significant reduction of the number of dialysis per patient in the I5NP group with respect to the Placebo group.

SUMMARY

In total, the QPI-1002 patient group consumed ~⅔ of dialysis than of the Placebo patients group In the overall mITTEE population there is a significant reduction of the number of dialysis per patient in the I5NP group with respect to the Placebo group according to the ZIP regression model, and it is supported by the sensitivity non-parametric tests.

In the sub-population according to donor age the –p-values are smaller and the difference between treatment groups the mean numbers of dialysis per patient increase.

Example 4: Generation of Novel Sequences for Active dsNA Compounds

Using proprietary algorithms and the known sequence of the mRNA of the p53 gene (SEQ ID NOS:1-7), the sequences of many potential dsNA compounds, were generated. The oligonucleotide sequences were prioritized based on their score in a proprietary algorithm as the best predicted sequences for targeting the human p53 gene expression.

Exemplary sense and antisense sequences useful for generating a dsNA temporary inhibitor of p53 gene are shown in Table 2, supra, and include SEQ ID NOS:36 and 37; 8 and 21; 9 and 22; 9 and 31; 10 and 23; 11 and 24; 12 and 25; 13 and 26; 14 and 27; 15 and 28; 16 and 29; 17 and 30; 18 and 31; 18 and 22; 19 and 32; 19 and 28; 20 and 33; and 20 and 21.

Example 5: Identification of Preferred Sequences for Active Nucleic Acid Compounds and Generation of Double-Stranded Nucleic Acid Compounds The best scoring oligonucleotide sequences were further prioritized based on their activity in vitro. For this purpose, dsRNA compounds were synthesized having the following modification patterns:

dsRNA compounds having unmodified ribonucleotides in the antisense strand and in the sense strand, and a -dTdT$ 3'-end overhang in both the antisense strand and the sense strand, with dT designating thymidine and dT$ designating thymidine with no terminal phosphate.

dsRNA compound having alternating 2'-O-methyl (Me) sugar modified ribonucleotides are present in the first, third, fifth, seventh, ninth, eleventh, thirteenth, fifteenth, seventeenth and nineteenth positions of the antisense strand, whereby the very same modification, i.e. a 2'-O-Methyl sugar modified ribonucleotides are present in the second, fourth, sixth, eighth, tenth, twelfth, fourteenth, sixteenth and eighteenth positions of the sense strand.

The following assay was used for the in vitro activity studies.

Example 6: Generation and Testing of Modified Double-Stranded Nucleic Acid Compounds The preferred sequences (SEQ ID NOS: 8-37) were used for generating modified double-stranded nucleic acid compounds. Some modified double-stranded nucleic acid compounds that were generated using the preferred antisense strand and sense strand sequences are set forth in Tables N and O, below. Table P below shows some preferred modified double-stranded nucleic acid compounds that were generated using the preferred antisense strand and sense strand sequences (SEQ ID NOS: 8-37).

TABLE N

| Duplex Name | Sense strand (5' > 3') | Antisense strand (5' > 3') |
|---|---|---|
| p53_34 | GGAUGUUUGGGAGAUGUAA | UUACAUCUCCCAAACAUCC |
| p53_35 | GACUCAGACUGACAUUCUA | UAGAAUGUCAGUCUGAGUC |
| p53_36 | GGGUUGGUAGUUUCUACAA | UUGUAGAAACUACCAACCC |
| p53_37 | GGGAUGUUUGGGAGAUGUA | UACAUCUCCCAAACAUCCC |
| p53_38 | GGAUCCACCAAGACUUGUA | UACAAGUCUUGGUGGAUCC |
| p53_39 | GAGGGAUGUUUGGGAGAUA | UAUCUCCCAAACAAUCCCUC |
| p53_40 | GGGCCUGACUCAGAACUGAA | UUCAGUCUGAGUCAGGCCC |
| p53_41 | GACUCAGACUGACAUUCUU | AAGAAUGUCAGUCUGAGUC |
| p53_42 | GCAUUUGCACCUACCUCAA | UUGAGGUAGGUGCAAAUGC |
| p53_43 | GGAUGUUUGGGAGAUGUAU | AUACAUCUCCCAAACAUCC |
| p53_44 | GGGCCUGACUCAGACUGAU | AUCAGUCUGAGUCAGGCCC |
| p53_45 | CAGACCUAUGGAAACUACA | UGUAGUUUCCAUAGGUCUG |

Activity Assay

About 1.5-2×10⁵ tested human or rat cells endogenously expressing p53 genes (Human HCT116 cells or Rat REF52 cells) were grown in 6 wells plate in 1.5 ml growth medium for about 24 hours to 30-50% confluence. Cells were then transfected with tested dsNA compound in a required final concentration 0.001-100 nM per well using Liopofectamine 2000 reagent. In order to determine the transfection efficiency, of the study, 5 wells were treated independently with Lipofectamine 2000 reagent and defined as "Negative Control samples" and 5 wells were transfected independently with active dsRNA at final concentration of 5 nM defined as "Control active samples" (positive control). Cy3-labeled siRNA transfected cells were used as positive control for transfection efficiency. Cells were then incubated in a 37±1° C., 5% CO₂ incubator for 48-72 hours. dsRNA transfected cells were harvested and RNA was isolated using EZ-RNA kit [Biological Industries (#20-410-100)]. Reverse transcription was performed as follows: cDNA was synthesized and human and/or rat p53 mRNA levels were determined, accordingly by Real Time qPCR and normalized to those of the Cyclophilin A (CYNA, PPIA) mRNA for each sample. dsRNA activity was determined based on the ratio of the mRNA quantity in siRNA-treated samples versus non-transfected control samples.

As a result of the activity study preferred sequences for novel dsRNA compounds for down regulation of the p53 gene were identified (results not shown). These sequences are set forth in Table 1, supra (SEQ ID NOS: 8-37

In all tables above and below the duplex names are identified by prefixes "p53" and "TP53" that are used interchangeably.

For all dsRNA compounds in Table N:

A, U, G, C—designates an unmodified ribonucleotide;

A, U, G, C—designates a 2-O-methyl sugar modified ribonucleotide;

In various embodiments, in the nucleic acid compounds in Table N, the ribonucleotide at the 3' terminus and at the 5' terminus in each of the antisense strand and the sense strand may be phosphorylated or non-phosphorylated. In some embodiments, of the nucleic acid compounds in Table N, in each of the antisense strand and the sense strand the ribonucleotide at the 3' terminus is phosphorylated and the ribonucleotide at the 5' terminus is non-phosphorylated. In some embodiments, in each of the nucleic acid compound in Table N, the antisense strand and the sense strand are non-phosphorylated at both the 3' terminus and the 5' terminus.

Certain exemplary duplexes for generation of double-stranded nucleic acid compounds for down-regulation of a p53 gene are set forth herein below in Table O. Additional duplexes are provided in the Examples section below.

TABLE O

P53 duplexes.

| Duplex Name | Sense (N')y 5 -> 3 | Antisense (N)x 5 -> 3 |
|---|---|---|
| p53_13 | cap-CAGACCUAUGGAAACUACU-C3-pi | AGUAGUuCCAUAGGUCUG-C3-C3 |
|  | cap-CAGACCUAUGGAAAcuacu-C3-pi | AGUAGUuCCAUAGGUCUG-C3-C3 |
|  | cap-CAGACCUAUGGAAACUACU-pi | AGUAGUUCCAUAGGUCUG-pi |
|  | cap-CAGACCUAUGGAAAcuaca-C3-pi | UGUAGUuCCAUAGGUCUG-C3-C3 |
|  | cap-CAGACCUAUGGAAACUACA-C3-pi | UGUAGUUCCAUAGGUCUG**-pi |
|  | cap-CAGACCUAUGGAAACUACA-pi | UGUAGUUCCAUAGGUCUG |
|  | cap-CAGACCUAUGGAAACUACA | UGUAGUUCCAUAGGUCUG |
| p53_34 | cap-GGAUGUUUGGGAGAUGUAA-C3-pi | UUACAuUCCCAAACAUCC-C3-C3 |
|  | cap-GGAUGUUUGGGAGAuguaa-C3-pi | UUACAuUCCCAAACAUCC-C3-C3 |
|  | cap-GGAUGUUUGGGAGAuguaa-C3-pi | AUACAuUCCCAAACAUCC-C3-C3 |
|  | cap-GGAUGUUUGGGAGAUGUAU-C3-pi | UUACAuUCCCAAACAUCC-C3-C3 |
|  | cap-GGAUGUUUGGGAGAuguaa-C3-pi | AUACAuUCCCAAACAUCC-C3-C3 |
|  | GGAUGUUUGGGAGAUGUAUzdTzdT$ | AUACAUCUCCCAAACAUCCzdTzdT$ |
| p53_35 | cap-GACUCAGACUGACAuucua-C3-pi | UAGAAUuUCAGUCUGAGUC-C3-C3 |
|  | cap-GACUCAGACUGACAUUCUA-C3-pi | UAGAAUuUCAGUCUGAGUC-C3-C3 |
|  | cap-GACUCAGACUGACAUUCUA-C3-pi | UAGAAuGUCAGUCUGAGUC-C3-C3 |
|  | cap-GACUCAGACUGACAUUCUA-C3-pi | UAGAAUuUCAGUCUGAGUC-C3-C3 |
|  | GACUCAGACUGACAUUCUAzdTzdT$ | UAGAAUGUCAGUCUGAGUCzdTzdT$ |
| p53_40 | cap-GGGCCUGACUCAGACUGAA-C3-pi | UUCAGUUGAGUCAGGCCC-C3-C3 |
|  | cap-GGGCCUGACUCAGAcugaa-C3-pi | UUCAGuUGAGUCAGGCCC-C3-C3 |
|  | cap-GGGCCUGACUCAGACUGAU-C3-pi | UUCAGuCUGAGUCAGGCCC-C3-C3 |
|  | cap-GGGCCUGACUCAGAcugau-C3-pi | AUCAGuCUGAGUCAGGCCC-C3-C3 |
|  | cap-GGGCCUGACUCAGACUGAA-C3-pi | UUCAGUUGAGUCAGGCCC-C3-C3 |
|  | cap-GGGCCUGACUCAGACUGAU-C3-pi | AUCAGUUGAGUCAGGCCC-C3-C3 |
|  | cap-GGGCCUGACUCAGACUGAA-C3-pi | UUCAGuCUGAGUCAGGCCC-C3-C3 |
|  | GGGCCUGACUCAGACUGAAzdTzdT$ | UUCAGUCUGAGUCAGGCCCzdTzdT$ |
| p53_41 | cap-GACUCAGACUGACAuucuu-C3-pi | AAGAAUuUCAGUCUGAGUC-C3-C3 |
|  | cap-GACUCAGACUGACAUUCUU-C3-pi | AAGAAUuUCAGUCUGAGUC-C3-C3 |
|  | cap-GACUCAGACUGACAUUCUU-C3-pi | AAGAAUuUCAGUCUGAGUC-C3-C3 |
|  | cap-GACUCAGACUGACAUUCUU-C3-pi | AAGAAuGUCAGUCUGAGUC-C3-C3 |
|  | GACUCAGACUGACAUUCUUzdTzdT$ | AAGAAUGUCAGUCUGAGUCzdTzdT$ |
| p53_43 | cap-GGAUGUUUGGGAGAuguaa-C3-pi | AUACAuUCCCAAACAUCC-C3-C3 |
|  | cap-GGAUGUUUGGGAGAUGUAU-C3-pi | AUACAuUCCCAAACAUCC-C3-C3 |
| p53_44 | cap-GGGCCUGACUCAGACUGAU-C3-pi | AUCAGuCUGAGUCAGGCCC-C3-C3 |
|  | cap-GGGCCUGACUCAGAcugau-C3-pi | AUCAGuCUGAGUCAGGCCC-C3-C3 |
|  | cap-GGGCCUGACUCAGACUGAU-C3-pi | AUCAGuCUGAGUCAGGCCC-C3-C3 |
|  | cap-GGGCCUGACUCAGACUGAU-C3-pi | AUCAGUUGAGUCAGGCCC**-C3-C3 |

TABLE O-continued

P53 duplexes.

| Duplex Name | Sense (N')y 5 -> 3 | Antisense (N)x 5 -> 3 |
|---|---|---|
| p53_45 | cap-CAGACCUAUGGAAAcuacu-C3-pi | UGUAGUuUCCAUAGGUCUG-C3-C3 |
|  | cap-CAGACCUAUGGAAACUACA-C3-pi | UGUAGUUUCCAUAGGUCUG-pi |
|  | cap-CAGACCUAUGGAAACUACA-pi | UGUAGUUUCCAUAGGUCUG |

For all double-stranded nucleic acid compounds in Table O:

A, U, G, C—designates an unmodified ribonucleotide;
A, U, G, C—designates a 2-O-methyl sugar modified ribonucleotide;
a, u, c, g —designates a nucleotide joined to an adjacent nucleotide by a 2'-5' internucleotide phosphate bond (5'>3');
cap—designates a capping moiety. In some preferred embodiments the capping moiety is the group consisting of an abasic ribose moiety, an abasic deoxyribose moiety, an inverted deoxyribose moiety, an inverted deoxyabasic moiety (idAb), amino-C6 moiety (AM-c6), C6-amino-pi, a non-nucleotide moiety, a mirror nucleotide, a 5,6,7,8-tetrahydro-2-naphthalene butyric phosphodiester (THNB) and a conjugate moiety.

pi—designates 3'-phosphate.
z—designates capping moiety
$—designates no terminal phosphate
dT$—designates thymidine (no phosphate)
C3—designates 1,3-Propanediol, mono(dihydrogen phosphate) (C3) [CAS RN: 13507-42-1].
C3-C3—designates two consecutive C3 molecules.

In various embodiments of the nucleic acid compounds described in Table O, supra, the C3-C3 non-nucleotide overhang covalently attached at the 3' terminus of the antisense strand is phosphorylated (—C3-C3-pi).

In some embodiments of the nucleic acid compounds described in Table O, supra, in each of the nucleic acid compounds, the ribonucleotide at the 5' terminus in the antisense strand is phosphorylated. In some embodiments of the nucleic acid compounds described in Table O, supra, in each of the nucleic acid compounds, the ribonucleotide at the 5' terminus in the antisense strand is non-phosphorylated.

TABLE P

| dsRNA Compound | Sense (N')y 5 -> 3 | Antisense (N)x 5 -> 3 |
|---|---|---|
| TP53_13_S2275 | C3-CAGACCUAUGGAAACUACU-C3-pi | 5' phos-AGUAGUuUCCAUAGGUCUG-C3;C3-pi |
| TP53_13_S2276 | C3-CAGACCUAUGGAAACUACU-C3-pi | 5' phos-AGUAGUuUCCAUAGGUCUG-C3;C3-pi |
| TP53_13_S2277 | C3-CAGACCUAUGGAAAcuacu-C3-pi | 5' phos-AGUAGUuUCCAUAGGUCUG-C3;C3-pi |
| TP53_13_S2278 | C3-CAGACCUAUGGAAAcuacu-C3-pi | 5' phos-AGUAGUuUCCAUAGGUCUG-C3;C3-pi |
| TP53_41-S709 | GACUCAGACUGACAUUCUU-dTdT$ | AAGAAUGUCAGUCUGAGUC-dTdT$ |
| TP53_41_S2279 | C3-GACUCAGACUGACAUUCUU-C3-pi | 5' phos-AAGAUgUCAGUCUGAGUC-C3;C3-pi |
| TP53_41_S2298 | C3-GACUCAGACUGACauucuu-C3-pi | 5' phos-AAGAAUgUCAGUCUGAGUC-C3;C3-pi |
| TP53_41_S2299 | C3-GACUCAGACUGACauucuu-C3-pi | 5' phos-AAGAAUgUCAGUCUGAGUC-C3;C3-pi |
| TP53_41_S2300 | C3-GACUCAGACUGACAUUCUU-C3-pi | 5' phos-AAGAAUgUCAGUCUGAGUC-C3;C3-pi |
| TP53_44_S2301 | C3-GGGCCUGACUCAGAcugau-C3-pi | 5' phos-AUCAGUcUGAGUCAGGCCC-C3;C3-pi |
| TP53_44_S2302 | C3-GGGCCUGACUCAGAcugau-C3-pi | 5' phos-AUCAGUcUGAGUCAGGCCC-C3;C3-pi |
| TP53_44_S2303 | C3-GGGCCUGACUCAGACUGAU-C3-pi | 5' phos-AUCAGUcUGAGUCAGGCCC-C3;C3-pi |
| TP53_44_S2304 | C3-GGGCCUGACUCAGACUGAU-C3-pi | 5' phos-AUCAGUcUGAGUCAGGCCC-C3;C3-pi |

In all tables above and below the duplex names are identified by prefixes "p53" and "TP53" that are used interchangeably. Thus, for example a compound identified by prefix "p53_13" and "TP53_13" designates a double-stranded nucleic acid compound having a sense strand sequence 5' CAGACCUAUGGAAACUACU 3' (SEQ ID NO:8) and an antisense strand sequence 5' AGUAGUUUC-CAUAGGUCUG 3' (SEQ ID NO: 21).

For all dsRNA compounds in Table P:
A, U, G, C—designates an unmodified ribonucleotide;
A, U, G, C designates a 2-O-methyl sugar modified ribonucleotide;
a, u, c, g —designates a nucleotide joined to an adjacent nucleotide (5'>3') by a 2'-5' internucleotide phosphate bond;
C3—designates 1,3-Propanediol, mono(dihydrogen phosphate) also identified as 3-Hydroxypropane-1-phosphate capping moiety [CAS RN: 13507-42-1].

49

C3C3—designates a capping moiety consisting of two consecutive C3 molecules pi—designates 3'-phosphate.

5'-phos—designates 5'-phosphate

These and other chemical modifications may be found in inter alia US patent and US application publications U.S. Pat. No. 8,362,229; 20120283309; 20130035368; 20130324591, to the assignee of the present application and incorporated by reference herein.

Activity of modified double-stranded nucleic acid compounds was studies in human HCT116 cells and in rat REF52 cells.

Table Q summarizes the in vitro activity results obtained for some of the double-stranded nucleic acid molecules in human HCT116 cell line. All of the dsNA compounds are described in Table P, supra.

The p53_13_S500 compound has sense strand SEQ ID NO: 8 and antisense strand SEQ ID NO: 21 and the following modification pattern: alternating 2'-O-methyl (Me) sugar modified ribonucleotides are present in the first, third, fifth, seventh, ninth, eleventh, thirteenth, fifteenth, seventeenth and nineteenth positions of the antisense strand, whereby the very same modification, i. e. a 2'-O-Methyl sugar modified ribonucleotides are present in the second, fourth, sixth, eighth, tenth, twelfth, fourteenth, sixteenth and eighteenth positions of the sense strand.

The in-vitro activity in Table Q is demonstrated as the % residual target mRNA relative to control.

TABLE Q

| Sample Description (dsRNA compound used) | Concentration of dsRNA compound | p53 residual mRNA % of control |
|---|---|---|
| None (control) | | 100 |
| p53_13_S500 | 50 nM | 25 |
| p53_13_S500 | 25 nM | 14 |
| p53_13_S500 | 5 nM | 33 |
| p53_13_S500 | 1 nM | 55 |
| p53_1_S500 | 50 nM | 22 |
| p53_1_S500 | 25 nM | 16 |
| p53_1_S500 | 5 nM | 52 |
| p53_1_S500 | 1 nM | 107 |
| p53_13_S2275 | 50 nM | 19 |
| p53_13_S2275 | 25 nM | 14 |
| p53_13_S2275 | 5 nM | 25 |
| p53_13_S2275 | 1 nM | 60 |
| p53_13_S2276 | 50 nM | 19 |
| p53_13_S2276 | 25 nM | 19 |
| p53_13_S2276 | 5 nM | 44 |
| p53_13_S2276 | 1 nM | 112 |
| p53_13_S2277 | 50 nM | 22 |
| p53_13_S2277 | 25 nM | 14 |
| p53_13_S2277 | 5 nM | 38 |
| p53_13_S2277 | 1 nM | 112 |
| p53_13_S2278 | 50 nM | 41 |
| p53_13_S2278 | 25 nM | 25 |
| p53_13_S2278 | 5 nM | 49 |
| p53_13_S2278 | 1 nM | 99 |
| p53_41_S709 | 50 nM | 5 |
| p53_41_S709 | 25 nM | 8 |
| p53_41_S709 | 5 nM | 14 |
| p53_41_S709 | 1 nM | 30 |
| p53_41_S2279 | 50 nM | 3 |
| p53_41_S2279 | 25 nM | 8 |
| p53_41_S2279 | 5 nM | 3 |
| p53_41_S2279 | 1 nM | 5 |
| p53_41_S2298 | 50 nM | 5 |
| p53_41_S2298 | 25 nM | 8 |
| p53_41_S2298 | 5 nM | 5 |
| p53_41_S2299 | 1 nM | |
| p53_41_S2299 | 50 nM | 3 |
| p53_41_S2299 | 25 nM | 3 |
| p53_41_S2299 | 5 nM | 5 |

50

TABLE Q-continued

| Sample Description (dsRNA compound used) | Concentration of dsRNA compound | p53 residual mRNA % of control |
|---|---|---|
| p53_41_S2299 | 1 nM | 5 |
| p53_41_S2300 | 50 nM | 3 |
| p53_41_S2300 | 25 nM | 3 |
| p53_41_S2300 | 5 nM | 2 |
| p53_41_S2300 | 1 nM | 3 |
| p53_44_S2301 | 50 nM | 5 |
| p53_44_S2301 | 25 nM | 5 |
| p53_44_S2301 | 5 nM | 3 |
| p53_44_S2301 | 1 nM | 14 |
| p53_44_S2302 | 50 nM | 3 |
| p53_44_S2302 | 25 nM | 3 |
| p53_44_S2302 | 5 nM | 5 |
| p53_44_S2302 | 1 nM | 8 |
| p53_44_S2303 | 50 nM | 3 |
| p53_44_S2303 | 25 nM | 5 |
| p53_44_S2303 | 5 nM | 3 |
| p53_44_S2303 | 1 nM | 3 |
| p53_44_S2304 | 50 nM | 5 |
| p53_44_S2304 | 25 nM | 5 |
| p53_44_S2304 | 5 nM | 11 |
| p53_44_S2304 | 1 nM | 19 |

Table R summarizes the in vitro activity results obtained for some of the double-stranded nucleic acid molecules in rat REF52 cell line.

The in-vitro activity in Table R is demonstrated as the % residual target mRNA relative to control.

TABLE R

| Sample Description (dsRNA compound used) | Concentration of dsRNA compound | p53 residual mRNA % of control |
|---|---|---|
| REF52 control | None | 100 |
| p53_13_S500 | 50 nM | 26 |
| | 25 nM | 30 |
| | 5 nM | 63 |
| | 1 nM | 68 |
| p53_41_S709 | 50 nM | 40 |
| | 25 nM | 87 |
| | 5 nM | 96 |
| | 1 nM | 211 |
| p53_41_S2279 | 50 nM | 38 |
| | 25 nM | 20 |
| | 5 nM | 21 |
| | 1 nM | 60 |
| p53_41_S2298 | 50 nM | 137 |
| | 25 nM | 81 |
| | 5 nM | 71 |
| | 1 nM | 113 |
| p53_41_S2299 | 50 nM | 116 |
| | 25 nM | 122 |
| | 5 nM | 107 |
| | 1 nM | 153 |
| p53_41_S2300 | 50 nM | 102 |
| | 25 nM | 81 |
| | 5 nM | 112 |
| | 1 nM | 149 |
| p53_44_S2301 | 50 nM | 12 |
| | 25 nM | 14 |
| | 5 nM | 25 |
| | 1 nM | 55 |
| p53_44_S2302 | 50 nM | 14 |
| | 25 nM | 9 |
| | 5 nM | 18 |
| | 1 nM | 59 |
| p53_44_S2303 | 50 nM | 20 |
| | 25 nM | 12 |
| | 5 nM | 12 |
| | 1 nM | 38 |

TABLE R-continued

| Sample Description (dsRNA compound used) | Concentration of dsRNA compound | p53 residual mRNA % of control |
|---|---|---|
| p53_44_S2304 | 50 nM | 22 |
| | 25 nM | 33 |
| | 5 nM | |
| | 1 nM | |

Example 7: Evaluation of the Knock Down Activity of Double-Stranded RNA Molecules Using psiCHECK™-2-System Three psiCHECK™-2-based (Promega) constructs were prepared for the evaluation of the potential activity. The psiCHECK constructs contained single copies of matched complementary guide (AS-CM). $1.3-1.5 \times 10^6$ human HeLa cells were inoculated in 10 cm dish. Cells were then incubated in $37 \pm 1°$ C., 5% $CO_2$ incubator for 24 hours. Growth medium was replaced one day post inoculation by 8 ml fresh growth medium and each plate was transfected with one of the plasmids mentioned above, using Lipofectamine™ 2000 reagent according to manufacturer's protocol and incubated for 5 hours at $37 \pm 1°$ C. and 5% $CO_2$. Following incubation, cells were re-plated in a 96-well plate at final concentration of $5 \times 10^3$ cells per well in 80 µl growth medium. After 16 hours, cells were transfected with transfection RNA compound using Lipofectamine™ 2000 reagent at final concentrations ranging from 0.01 nM to 100 nM in a 100 µl final volume. Cells were then incubated for 48 hours at $37 \pm 1°$ C. following assessment of Renilla and FireFly luciferase activities as described below.

48 hours following transfection with double-stranded RNA compound, Renilla and FireFly luciferase activities were measured in each of the siRNA transfected samples, using Dual-Luciferase® Assay kit (Promega, Cat#E1960) according to manufacturer procedure. Renilla luciferase activity value was divided by Firefly luciferase activity value for each sample (normalization). Renilla luciferase activity is finally expressed as the percentage of the normalized activity value in tested sample relative to the normalized value obtained in cells transfected with the corresponding psiCHECK™-2 plasmid only but with no double-stranded RNA.

The results of the activity study in psiCHECK™-2-System (results not shown) were used to select the best highly active sequences for generating highly active double-stranded nucleic acid compound for down-regulating the p-53 gene.

Although the above examples have illustrated particular ways of carrying out embodiments of the invention, in practice persons skilled in the art will appreciate alternative ways of carrying out embodiments of the invention, which are not shown explicitly herein. It should be understood that the present disclosure is to be considered as an exemplification of the principles of this invention and is not intended to limit the invention to the embodiments illustrated.

Those skilled in the art will recognize, or be able to ascertain using no more than routine experimentation, equivalents of the specific embodiments of the invention described herein. Such equivalents intended to be encompassed by the following claims.

The invention claimed is:

1. A method of prophylaxis of ischemic reperfusion injury (IRI) in a kidney at risk of IRI transplanted into a subject, the method comprising contacting the kidney with a temporary inhibitor of a p53 gene in an amount effective to provide prophylaxis of IRI in the kidney,
wherein the kidney is from a donor aged 35 years or older, and
wherein the inhibitor is a synthetic small interfering ribonucleic acid (siRNA) having the structure:

(SEQ ID NO: 37)
5' UGAAGGGUGAAAUAUUCUC 3' (antisense strand)

(SEQ ID NO: 36)
3' ACUUCCCACUUUAUAAGAG 5' (sense strand)

wherein each of A, C, U and G is a ribonucleotide and each consecutive ribonucleotide is joined to the next ribonucleotide by a covalent bond; and
wherein alternating ribonucleotides in both the antisense strand and the sense strand are 2'-O-methyl sugar modified ribonucleotides and a 2'-O-methyl sugar modified ribonucleotide is present at both the 5' terminus and the 3' terminus of the antisense strand and an unmodified ribonucleotide is present at both the 5' terminus and the 3' terminus of the sense strand; or a pharmaceutically acceptable salt thereof.

2. The method of claim 1, wherein contacting the kidney with the temporary inhibitor comprises administering the temporary inhibitor to the subject possessing the kidney at risk of IRI after transplantation.

3. The method of claim 1, wherein contacting the kidney with the temporary inhibitor comprises contacting the kidney with the temporary inhibitor ex vivo prior to transplantation of the kidney into the subject.

4. The method claim 1, wherein the kidney at risk of IRI is from a donor aged 45 years old or older.

5. The method of claim 1, wherein prophylaxis of IRI results in prophylaxis of IRI-associated kidney dysfunction or IRI-associated delayed graft function (DGF) of the kidney.

6. The method of claim 5, wherein the prophylaxis of DGF results in the reduction of the amount, intensity, and duration of dialytic support during at least the first 7 days post-transplantation in a dialysis-dependent end stage renal disease (ESRD) patient undergoing deceased donor renal transplantation.

7. The method of claim 5, wherein prophylaxis of DGF results in at least one of a longer time interval between transplantation and the first dialysis treatment post-transplantation, a shorter mean duration of initial post-transplantation course of dialysis, and a higher measured glomerular filtration rate (mGFR) at the end of the first post-transplantation month.

8. The method of claim 5, wherein the prophylaxis of IRI results in the reduction of the amount, intensity, and/or duration of dialytic support during the first 180 days post-transplantation in a dialysis-dependent end stage renal disease (ESRD) patient undergoing deceased donor renal transplantation.

9. The method of claim 1, wherein the kidney is preserved entirely by cold storage following removal from the donor and prior to implantation into the subject.

10. The method claim 1, wherein the kidney is preserved by machine-perfusion for at least a portion of time following removal from the donor and prior to implantation into the subject.

11. The method of claim 1, further comprising the steps of (a) selecting a recipient having a kidney from an Expanded Criteria Donor, and (b) administering to the subject the temporary inhibitor in an amount effective to provide prophylaxis of DGF in the subject.

12. The method of claim 1, wherein the kidney is from a donor who is or was between the ages of 50 and 59 (inclusive) who does not have at least two of the following: a history of high blood pressure, terminal serum creatinine level greater than 1.5 mg/dl, and cardiovascular cause of brain death.

13. The method of claim 1, wherein the 5' termini and the 3' termini are unphosphorylated.

14. The method of claim 1, wherein the pharmaceutically acceptable salt is a sodium salt.

15. The method claim 1, wherein the temporary inhibitor of a p53 gene is administered at a dose of about 1 to about 50 mg/kg.

16. The method of claim 15, wherein the temporary inhibitor of a p53 gene is administered at a dose of about 10 mg/kg.

17. The method of claim 1, wherein the temporary inhibitor is administered by intravenous (IV) injection.

18. The method of claim 17, wherein the intravenous (IV) injection is administered in a single treatment, wherein the single treatment comprises a single dose or multiple doses.

19. The method of claim 18, wherein the single treatment is a single intravenous push (IVP).

20. The method of claim 17, wherein the intravenous (IV) injection is administered directly into a proximal port of a central venous line or through a peripheral line.

21. The method of claim 1, wherein the temporary inhibitor is conjugated or formulated in liposomes or nanoparticles.

22. The method of claim 1, wherein the subject is further administered a medication selected from the group consisting of an antiviral agent, an antifungal agent, an antimicrobial agent, an immunosuppressant agent, and any combination thereof.

23. The method of claim 22, wherein the medication is an immunosuppressant agent that is a calcineurin inhibitor.

24. The method of claim 22, wherein the immunosuppressant agent is selected from the group consisting of tacrolimus (TAC), mycophenolate mofetil (MMF), mycophenolic acid (MPA), a corticosteroid, a cyclosporine, an azathioprine, a sirolimus, and any combination thereof.

25. The method of claim 24, wherein the immunosuppressant agent is tacrolimus (TAC).

26. The method of claim 1, wherein the subject is further administered an antibody induction therapy agent.

27. The method of claim 26, wherein the antibody induction therapy agent comprises a polyclonal anti-thymocyte globulin (ATG) or an anti-CD25 (anti-IL-2R) monoclonal antibody.

* * * * *

UNITED STATES PATENT AND TRADEMARK OFFICE
CERTIFICATE OF CORRECTION

PATENT NO. : 9,868,953 B2
APPLICATION NO. : 15/650297
DATED : January 16, 2018
INVENTOR(S) : Elizabeth C. Squiers et al.

Page 1 of 1

It is certified that error appears in the above-identified patent and that said Letters Patent is hereby corrected as shown below:

Column 1, Line 4, below the title please insert:
--CROSS-REFERENCE TO RELATED APPLICATIONS
This application is a continuation application of U.S. Application Serial No. 15/312,425, filed on November 18, 2016, which is the U.S. National Stage of International Application No. PCT/US2015/032499, filed on May 27, 2015, which claims the benefit of U.S. Provisional Application Serial No. 62/004,239, filed on May 29, 2014. The contents of each of these applications are incorporated herein by reference in their entireties.--.

Column 77, Line 62, in Claim 4, after "method" insert --of--.

Column 78, Line 48, in Claim 10, after "method" insert --of--.

Column 79, Line 1, in Claim 15, after "method" insert --of--.

Signed and Sealed this
Twenty-second Day of May, 2018

Andrei Iancu
*Director of the United States Patent and Trademark Office*

SEQUENCE LISTING

<160> NUMBER OF SEQ ID NOS: 37

<210> SEQ ID NO 1
<211> LENGTH: 2586
<212> TYPE: RNA
<213> ORGANISM: Homo sapiens

<400> SEQUENCE: 1

```
gauuggggu uucccuccc augugcucaa gacuggcgcu aaaaguuuug agcuucucaa      60
aagucuagag ccaccgucca gggagcaggu agcugcuggg cuccggggac acuuugcguu     120
cgggcuggga gcgugcuuuc cacgacggug acacgcuucc cuggauuggc agccagacug    180
ccuuccgggu cacugccaug gaggagccgc agucagaucc uagcgucgag cccccucuga    240
gucaggaaac auuuucagac cuauggaaac uacuuccuga aaacaacguu cuguccccu     300 ugccguccca agcaauggau gauuugaugc uguccccgga cgauauugaa caauggucua    360
cugaagaccc agguccagau gaagcuccca gaaugccaga ggcugcuccc cccguggccc     420
cugcaccagc agcuccuaca ccggcggccc cugcaccagc cccuccugg ccccugucau    480 cuucugcucc uucccagaaa accaccagg gcagcuacgg uuuccgucug ggcuucuugc    540
auucugggac agccaagucu gugacuugca cguacucccc ugcccucaac aagauguuuu    600
gccaacuggc caagaccugc ccugugcagc uguggguuga uuccacaccc ccgcccggca    660
cccgcguccg cgccauggcc aucuacaagc agucacagca caugacggag guugugaggc    720
gcugccccca ccaugagcgc ugcucagaua gcgauggucu ggcccccucu cagcaucuua    780
uccgagugga aggaaauuug cguguggagu auuuggauga cagaaacacu uuucgacaua    840
```

| | |
|---|---|
| gugugguggu gcccuaugag ccgccugagg uuggcucuga cuguaccacc auccacuaca | 900 |
| acuacaugug uaacaguucc ugcaugggcg gcaugaaccg gaggcccauc cucaccauca | 960 |
| ucacacugga agacuccagu gguaaucuac ugggacggaa cagcuuugag gugcguguuu | 1020 |
| gugccugucc ugggagagac cggcgcacag aggaagagaa ucuccgcaag aaagggagc | 1080 |
| cucaccacga gcugccccca gggagcacua agcgagcacu gcccaacaac accagcuccu | 1140 |
| cuccccagcc aaagaagaaa ccacuggaug gagaauauuu cacccuucag auccgugggc | 1200 |
| gugagcgcuu cgagauguuc cgagagcuga augaggccuu ggaacucaag gaugcccagg | 1260 |
| cugggaagga gccaggggg agcagggcuc acuccagcca ccugaaguc aaaaagggu c| 1320 |
| agucuaccuc ccgccauaaa aaacucaugu ucaagacaga agggccugac ucagacugac | 1380 |
| auucuccacu ucuuguuccc cacugacagc cucccaccc caucucccc uccccugcca | 1440 |
| uuuuggguuu uggucuuug aacccuugcu ugcaauaggu gugcgucaga agcacccagg | 1500 |
| acuuccauuu gcuuugucc ggggcuccac ugaacaaguu ggccugcacu ggugunuugu | 1560 |
| ugugggagg aggaugggga guaggacaua ccagcuuaga uuuuaagguu uuacuguga | 1620 |
| gggauguuug ggagauguaa gaaauguucu gcaguuaag gguuaguuua caaucagcca | 1680 |
| cauucuaggu agggccccac uucaccguac uaaccaggga agcugucccu cacuguuaa | 1740 |
| uuuucucuaa cuucaaggcc cauaucugug aaaugcuggc auuugcaccu accucacaga | 1800 |
| gugcauugug agggguuaaug aaauaaugua caucuggccu ugaaaccacc uuuuauuaca | 1860 |
| uggggucuag aacuugaccc ccuugagggu gcuuguuccc ucccuguu ggucgguggg | 1920 |
| uugguaguuu cuacaguugg gcagcugguu agguagaggg aguugucaag ucucugcugg | 1980 |
| cccagccaaa cccugucuga caaccucuug gugaaccuua guaccuaaaa ggaaaucuca | 2040 |
| ccccauccca cacccuggag gauuucaucu cuuguauaug augaucugga uccaccaaga | 2100 |
| cuuguuuau gcucagggu aauuucuuuu ucuuuuuuu uuuuuuuuu ucuuuucuu | 2160 |
| ugagacuggg ucucgcuuug uugcccaggc uggaguggag uggcgugauc uuggcuuacu | 2220 |
| gcagccuuug ccucccggc ucgagcaguc cugccucagc cuccggagua gcuggacca | 2280 |
| cagguucaug ccaccauggc cagcaacuu ugcauguuu uguagagaug gggucucaca | 2340 |
| guguugccca ggcuggucuc aaaucccugg gcucaggcga uccaccuguc ucagccuccc | 2400 |
| agagugcugg gauuacaauu gugagccacc acguccagcu ggaaggguca acaucuuuua | 2460 |
| cauucugcaa gcacaucugc auuuucaccc cacccuuccc cuccuucucc cuuuuuauau | 2520 |
| cccauuuuua uaucgaucuc uuauuuuaca auaaaacuuu gcugccaccu guguguucuga | 2580 |
| gggguig | 2586 |

<210> SEQ ID NO 2
<211> LENGTH: 2583
<212> TYPE: RNA
<213> ORGANISM: Homo_Sapiens

<400> SEQUENCE: 2

| | |
|---|---|
| gauuggggun uuccccuccc augugcucaa gacuggcgcu aaaaguuuug agcuucucaa | 60 |
| aagucuagag ccaccgucca gggagcaggu agcugcuggg cuccggggac acuuugcguu | 120 |
| cgggcuggga gcgugcuuuc cacgacggug acacgcuucc cuggauuggc cagacugccu | 180 |
| uccgggucac ugccauggag gagccgcagu cagauccuag cgucgagccc ccucugaguc | 240 |
| aggaaacauu uucagaccua uggaaacuac uuccugaaaa caacguucug uccccuugc | 300 |
| cgucccaagc aauggaugau uugaugcugu ccccggacga uauugaacaa ugguucacug | 360 |

| | |
|---|---|
| aagacccagg uccagaugaa gcucccagaa ugccagaggc ugcuccccc guggcccug | 420 |
| caccagcagc uccuacaccg gcggccccug caccagcccc cuccuggccc cugucaucuu | 480 |
| cugucccuuc ccagaaaacc uaccagggca gcuacgguuu ccgucugggc uucuugcauu | 540 |
| cuggacagc caagucugug acuugcacgu acuccccugc ccuaacaag auguuugcc | 600 |
| aacuggccaa gaccugcccu gugcagcugu ggguugauuc cacacccccg cccggcaccc | 660 |
| gcguccgcgc cauggccauc uacaagcagu cacagcacau gacggagguu gugaggcgcu | 720 |
| gcccccacca ugagcgcugc ucagauagcg augguucuggc cccuccucag caucuuaucc | 780 |
| gagugggaagg aaauuugcgu guggaguauu uggaugacag aaacacuuuu cgacauagug | 840 |
| uggugugcc cuaugagccg ccugagguug gcucugacug uaccaccauc cacuacaacu | 900 |
| acauguguaa caguuccgc augggcggca ugaaccggag gcccauccuc accaucauca | 960 |
| cacuggaaga ucccaguggu aaucuacugg gacggaacag cuuugaggug cguguuugug | 1020 |
| ccuguccugg gagagaccgg cgcacagagg aagagaaucu ccgcaagaaa ggggagccuc | 1080 |
| accacgagcu gccccaggg agcacuaagc gagcacugcc caacaacacc agcuccucuc | 1140 |
| cccagccaaa gaagaaacca cuggauggag aauauuucac ccuucagauc cgugggcgug | 1200 |
| agcgcuucga gauguuccga gagcugaaug aggccuugga acucaaggau gcccaggcug | 1260 |
| ggaaggagcc aggggggagc agggcucacu ccagccaccu gaaguccaaa aagggucagu | 1320 |
| cuaccucccg ccauaaaaaa cucauguuca agacagaagg gccugacuca gacugacauu | 1380 |
| cuccacuucu uguuccccac ugacagccuc ccaccccau cucccccc ccugccauuu | 1440 |
| ugggguuuugg gucuuugaac ccuugcuugc aauaggugug cgucagaagc acccaggacu | 1500 |
| uccauugcu uugucccggg gcuccacuga acaaguggc cugcacuggu guuuuguugu | 1560 |
| ggggaggagg auggggagua ggacauacca gcuuagauuu uaagguuuuu acugugaggg | 1620 |
| auguuuggga gauguaagaa auguucucgc aguuaagggu uaguuuacaa ucagccacau | 1680 |
| ucuagguagg ggcccacuuc accguacuaa ccagggaagc ugucccucac guugaauuu | 1740 |
| ucucuaacuu caaggcccau aucgugaaa ugcuggcauu ugcaccuacc ucacagagug | 1800 |
| cauugugagg guuaaugaaa uaaugacauu cuggccuuga aaccaccuuu uauuacaugg | 1860 |
| ggucuagaac uugaccccu ugagggugcu uguucccucu cccguugguu cgguggguug | 1920 |
| guaguuucua caguugggca gcugguuagg uagagggagu gucaagucu cugcuggccc | 1980 |
| agccaaaccc ugucugacaa ccucuuggug aaccuuagua ccuaaaagga aaucucaccc | 2040 |
| caucccacac ccuggaggau uucaucucuu guauaugaug aucuggaucc accaagacuu | 2100 |
| guuuuaugcu cagggucaau uucuuuuuc uuuuuuuu uuuuuuucu uuucuuuga | 2160 |
| gacuggucu cgcuuuguug cccaggcugg agugagugg cgugaucuug gcuuacugca | 2220 |
| gccuuugccu ccccggcucg agcaguccug ccucagccuc cggaguagcu gggaccacag | 2280 |
| guucaugcca ccauggccag ccaacuuuug cauguuugu agagauggg ucucacagug | 2340 |
| uugcccaggc uggucucaaa cuccugggcu caggcgaucc accugucuca gccucccaga | 2400 |
| gugcugggau acaauugug agccaccacg uccagcugga agggucaaca ucuuuuacau | 2460 |
| ucugcaagca caucugcauu uucaccccac ccuuccccuc cuucucccuu uuuauauccc | 2520 |
| auuuuuauau cgaucucuua uuuuacaaua aaacuuugcu gccaccugug ugucugaggg | 2580 |
| gug | 2583 |

<210> SEQ ID NO 3

```
<211> LENGTH: 2719
<212> TYPE: RNA
<213> ORGANISM: Homo_Sapiens

<400> SEQUENCE: 3
gauuggggua uucccuuccc augugcucaa gacuggcgcu aaaaguuuug agcuucucaa      60
aagucuagag ccaccgucca gggagcaggu agcugcuggg uccggggac acuuugcguu     120
cgggcuggga gcgugcuuuc cacgacggug acacgcuucc cuggauuggc agccagacug    180
ccuuccgggu cacugccaug gaggagccgc agucagaucc uagcgucgag cccccucuga    240
gucaggaaac auuucagac cuauggaaac uacuuccuga aaacaacguu cugucccccu     300
ugccguccca agcaauggau gauuugaugc uguccccgga cgauauugaa caaugguuca    360
cugaagaccc agguccagau gaagucccca gaaugccaga ggcugcuccc ccgguggccc    420
cugcaccagc agcuccuaca ccggcggccc cugcaccagc ccccuccugg ccccugucau    480
cuucuguccc uucccagaaa accuaccagg gcagcuacgg uuccgucug ggcuucuugc     540
auucgggac agccaagucu ugacuugca cguacucccc ugcccucaac aagauguuuu      600
gccaacuggc caagaccugc ccgugcagc ugugggиuga uccacacccc ccgcccggca     660
cccgcguccg cgccauggcc aucuacaagc agucacagca caugcggag guugugaggc     720
gcugccccca ccaugagcgc ugcucagaua gcgauggucu ggccccuccu cagcaucuua    780
uccgagugga aggaaauuug cgugugagu auuuggauga cagaaacacu uuucgacaua    840
guguggugu gcccuaugag ccgccugagg uuggcucuga cuguaccacc auccacuaca    900
acuacauguɡ uaacaguucc ugcauggcg gcaugaaccg gaggcccauc cucaccauca    960
ucacacugga agauccagu gguaaucuac ugggacggaa cagcuuugag gugcguguuu   1020
gugccugucc ugggagagac cggcgcacag aggaagagau ucccgcaag aaaggggagc   1080
cucaccacga gcugccccca gggagcacua agcgagcacu gcccaacaac accagcuccu   1140
cuccccagcc aaagaagaaa ccacuggaug agaauauuuu cacccuucag gaccagacca   1200
gcuuucaaaa agaaaauugu aaagagagc augaaaaugg uucuaugacu uugccugaua   1260
cagaugcuac uugacuuacg auggugиuac uuccugauaa acucgucgua aguugaaaau   1320
auuauccgug ggcgugagcg cuucgagaug uuccgagagc ugaaugaggc cuuggaacuc   1380
aaggaugccc aggcugggaa ggagccaggg gggagcaggg cucacuccag ccaccugaag   1440
uccaaaaagg gucagucuac cucccgccau aaaaaacuca uuucaagac agaagggccu   1500
gacucagacu gacauucucc acuucuuguu ccccacugac agccucccac ccccaucucu   1560
cccuccccug ccauuuuggg uuuugggucu uugaacccuu gcuugcaaua ggugugcguc   1620
agaagcaccc aggacuucca uuugcuuugu ccggggcuc cacugaacaa guuggccugc   1680
acugguguuu uguguggggg aggaggaugg ggaguaggac auaccagcuu agauuuuaag   1740
guuuuuacug ugagggaugu uugggagaug uaagaaaugu ucuugcaguu aagggиuagu   1800
uuacaaucag ccacauucua gguaggggcc cacuucaccg uacuaaccag ggaagcuguc   1860
ccucacuguu gaauuuucuc uaacuucaag gcccauaucu gugaaaugcu ggcauuuugca  1920
ccuaccucac agagugcauu gugagggиua augaaauaau gucaucugg ccuugaaacc   1980
accuuuuauu acauggggиc uagaacuuga ccсccиugag ggugcuuguu cccucucccu   2040
guuggucggu gggииuggиag uuucuacagu ugggcagcug guuagguaga gggaguиguc   2100
aagcucucug uggcccagcc aaaccccuguс ugacaaccuc uggиugaacc uuagиaccua   2160
aaaggaaauc ucaccсccauc ccacacccug gaggauиuca ucucuuguau augaugaucu  2220
```

| | |
|---|---|
| ggauccacca agacuuguuu uaugcucagg gucaauuucu uuuucuuuu uuuuuuuuu | 2280 |
| uuuucuuuuu cuuugagacu gggucucgcu uguugccca ggcuggagug gauggcgug | 2340 |
| aucuuggcuu acugcagccu ugccucccc ggcucgagca guccugccuc agccuccgga | 2400 |
| guagcuggga ccacagguuc augccaccau ggccagccaa cuuuugcaug uuuuguagag | 2460 |
| auggggucuc acaguguugc ccaggcuggu cucaaacucc ugggcucagg cgauccaccu | 2520 |
| gucucagccu cccagagugc ugggauuaca auugugagcc accacgucca gcuggaaggg | 2580 |
| ucaacaucuu uuacauucug caagcacauc ugcauuuuca ccccacccuu ccccuccuuc | 2640 |
| ucccuuuuua uacccauuu uuauaucgau cucuuauuuu acaauaaaac uuugcugcca | 2700 |
| ccugugaguc ugaggggug | 2719 |

<210> SEQ ID NO 4
<211> LENGTH: 2646
<212> TYPE: RNA
<213> ORGANISM: Homo_Sapiens

<400> SEQUENCE: 4

| | |
|---|---|
| gauuggggu uucccuccc augugcucaa acuggcgcu aaaaguuuug agcuucucaa | 60 |
| aagucuagag ccaccgucca gggagcaggu agcugcuggg uccggggac acuuugcguu | 120 |
| cgggcuggga gcgugcuuuc cacgacggug acacgcuucc cuggauuggc agccagacug | 180 |
| ccuuccgggu cacugccaug gaggagccgc agucagaucc uagcgucgag ccccucuga | 240 |
| gucaggaaac auuucagac cuauggaaac uacuuccuga aaacaacguu cuguccccu | 300 |
| ugccgucccca agcaauggau gauuugaugc uguccccgga cgauauugaa caauggguuca | 360 |
| cugaagaccc aggucccagau gaagcuccca gaaugccaga ggcugcuccc ccgugggccc | 420 |
| cugcaccagc agcuccuaca ccggcggccc cugcaccagc ccccuccugg ccccugucau | 480 |
| cuucugucc uucccagaaa accuaccagg gcagcuacgg uuccgucug ggcuucuugc | 540 |
| auucuggac agccaagucu ugacauugca cguacucccc ugcccucaac aagauguuuu | 600 |
| gccaacuggc caagaccugc ccugugcagc ugugggguga uuccacaccc cgcccggca | 660 |
| cccgcguccg cgccauggcc aucuacaagc agucacagca caugcgagc uugugagggc | 720 |
| gcugccccca ccaugagcgc ugcucagaua gcgauggucu ggcccucccu cagcaucuua | 780 |
| uccgaguga aggaaauuug cgugugagu auuggauga cagaaacacu uuucgacaua | 840 |
| gugugguggu gcccuaugag ccgccugagg uuggcucuga cuguaccacc auccacuaca | 900 |
| acuacaugug uaacaguucc ugcaugggcg gcaugaaccg gaggcccauc cuaccauca | 960 |
| ucacacugga agacuccagu gguaaucuac ugggacggaa cagcuuugag gugcguguuu | 1020 |
| gugccugucc ugggagagac cggcgcacag aggaagagaa ucccgcaag aaagggagc | 1080 |
| cucaccacga gcugccccca gggagcacua agcgagcacu gcccaacaac accagcuccu | 1140 |
| cucccagcc aaagaagaaa ccacuggaug agaauauuu cacccuucag augcuacuug | 1200 |
| acuuacgaug uguuacuuc cugauaaacu cgucguaagu ugaaaauauu auccgugggc | 1260 |
| gugagcgcuu cgagauguuc cgagagcuga augaggccuu ggaacucaag gaugcccagg | 1320 |
| cuggaaagga gccaggggg agcagggcuc acuccagcca ccugaagucc aaaaagggguc | 1380 |
| agucuaccuc ccgccauaaa aaacucaugu caagacaga agggccugac ucagacugac | 1440 |
| auucuccacu ucuuguuccc cacugacagc cucccacccc caucucuccc ucccugcca | 1500 |
| uuuugggguuu ugggucuuug aacccuugcu ugcaauaggu gugcgucaga agcacccagg | 1560 |

| | |
|---|---|
| acuuccauuu gcuuugucce ggggcuccac ugaacaaguu ggccugcacu ggugaunuugu | 1620 |
| ugugggggagg aggaugggga guaggacaua ccagcuuaga uuuuaagguu uuuacuguga | 1680 |
| gggauguuug ggagauguaa gaaauguucu ugcaguuaag gguuaguuua caaucagcca | 1740 |
| cauucuaggu aggggcccac uucaccguac uaaccaggga agcugucccu cacuguugaa | 1800 |
| uuuucucuaa cuucaaggcc cauaucugug aaaugcuggc auuugcaccu accucacaga | 1860 |
| gugcauugug aggguuaaug aaauaaugua caucuggccu ugaaaccacc uuuuauuaca | 1920 |
| uggggucuag aacuugaccc ccuugagggu gcuuguuccc ucccuguu ggucgguggg | 1980 |
| uugguaguuu cuacaguugg gcagcugguu agguagaggg aguugucaag ucucugcugg | 2040 |
| cccagccaaa cccugucuga caaccucuug gugaaccuua guaccuaaaa ggaaaucuca | 2100 |
| ccccaucccca cacccuggag gauuucaucu cuuguauaug augaucugga uccaccaaga | 2160 |
| cuuguuuuau gcucagagguc aauuucuuuu ucuuuuuuuu uuuuuuuu ucuuuuucuu | 2220 |
| ugagacuggg ucucgcuuug uugcccaggc uggaguggag uggcgugauc uuggcuuacu | 2280 |
| gcagccuuug ccuccccggc ucgagcaguc cugcccagc cuccggagua gcugggacca | 2340 |
| cagguucaug ccaccauggc cagccaacuu uugcauguuu uguagagaug gggucucaca | 2400 |
| guguugccca ggcuggucuc aaacuccugg gcucaggcga uccaccgguc ucagccuccc | 2460 |
| agagugcugg gauuacaauu gugagccacc acgccagcu ggaagggca acaucuuuua | 2520 |
| cauucugcaa gcaucugc auuucaccce caccuucccc cuccuucccc cuuuuauau | 2580 |
| cccauuuuua uaucgaucuc uuauuuuaca auaaaacuuu gcugccaccu gugugucuga | 2640 |
| ggggug | 2646 |

<210> SEQ ID NO 5
<211> LENGTH: 2271
<212> TYPE: RNA
<213> ORGANISM: Homo_Sapiens

<400> SEQUENCE: 5

| | |
|---|---|
| ugaggccagg agauggaggc ugcagugagc ugugaucaca ccacugugcu ccagccugag | 60 |
| ugacagagca agacccuauc ucaaaaaaaa aaaaaaaaa gaaaagcucc ugaggguguag | 120 |
| acgccaacuc ucucuagcuc gcuagugggu ugcaggaggu gcuuacgcau guuuguuucu | 180 |
| uugcugccgu cuuccaguug cuuuaucugu ucacuugugc ccugacuuuc aacucugucu | 240 |
| ccuuccucuu ccuacaguac uccccugccc ucaacaagau guuuugccaa cuggccaaga | 300 |
| ccugcccugu gcagcugugg guugauucca cacccccgcc cggcacccgc guccgcgcca | 360 |
| uggccaucua caagcagucu cagcacauga cggagguugu gaggcgcugc ccccaccaug | 420 |
| agcgcugcuc agauagcgau ggucuggccc uccucagca ucuuauccga guggaaggaa | 480 |
| auuugcgugu ggaguauuug gaugacagaa acacuuuucg acauagugug guggugcccu | 540 |
| augagccgcc ugagguugc ucugacugua ccaccaucca cuacaacuac auguguaaca | 600 |
| guccugcau gggcggcaug aaccggaggc ccauccucac caucaucaca cuggaagacu | 660 |
| ccagugguaa ucuacuggga cggaacagcu uugaggugcg uguuugugcc uguccuggga | 720 |
| gagaccggcg cacagaggaa gagaaucucc gcaagaaagg ggagccucac cacgagcugc | 780 |
| ccccagggag cacuaagcga gcacugccca acaacaccag cuccucuccc cagccaaaga | 840 |
| agaaaccacu ggauggagaa uauuucaccc uucagauccg ugggcgugag cgcuucgaga | 900 |
| uguuccgaga gcugaaugag gccuuggaac ucaaggaugc ccaggcuggg aaggagccag | 960 |
| gggggagcag ggcucacucc agccaccuga aguccaaaaa gggucagucu accucccgcc | 1020 |

| | | | | |
|---|---|---|---|---|
| auaaaaaacu | cauguucaag | acagaagggc | cugacucaga | cugacauucu ccacuucuug | 1080 |
| uuccccacug | acagccuccc | accccauau | cucccucccc | ugccauuuug gguuuugggu | 1140 |
| cuuugaaccc | uugcuugcaa | uaggugugcg | ucagaagcac | ccaggacuuc cauuugcuuu | 1200 |
| gucccggggc | uccacugaac | aaguuggccu | gcacugugu | uuuguugugg ggaggaggau | 1260 |
| ggggaguagg | acauaccagc | uuagauuuua | agguuuuuac | ugugagggau guuugggaga | 1320 |
| uguaagaaau | guucuugcag | uuaaggguua | guuuacaauc | agccacauuc uagguagggg | 1380 |
| cccacuucac | cguacuaacc | agggaagcug | ucccucacug | uugaauuuuc ucuaacuuca | 1440 |
| aggcccauau | cugugaaaug | cuggcauuug | caccuaccuc | acagagugca uugugagggu | 1500 |
| uaaugaaaua | auguacaucu | ggccuugaaa | ccaccuuuua | uuacauggggg ucuagaacuu | 1560 |
| gaccccuug | agggugcuug | uucccucucc | cguuggucg | gugggguuggu aguuucuaca | 1620 |
| guugggcagc | ugguuaggua | gagggaguug | ucaagucucu | gcuggccag ccaaacccug | 1680 |
| ucugacaacc | ucuuggugaa | ccuuaguacc | uaaaaggaaa | ucucaccca ucccacaccc | 1740 |
| uggaggauuu | caucucuugu | auaugaugau | cuggauccac | caagacuugu uuuaugcuca | 1800 |
| ggucaauuu | cuuuuucuu | uuuuuuuuu | uuuuucuuu | uucuuugaga cugggucucg | 1860 |
| cuuuguugcc | caggcuggag | uggaguggcg | ugaucuuggc | uuacugcagc cuuugccucc | 1920 |
| ccggcucgag | caguccugcc | ucagcccccg | gaguagcugg | gaccacaggu ucaugccacc | 1980 |
| auggccagcc | aacuuuugca | uguuuugaug | agauggggc | ucacagucguu gcccaggcug | 2040 |
| gucucaaacu | ccugggcuca | ggcgauccac | cugucucagc | cucccagagu gcugggauua | 2100 |
| caauugugag | ccaccacguc | cagcuggaag | ggucaacauc | uuuuacauuc ugcaagcaca | 2160 |
| ucugcauuuu | caccccaccc | uuccccuccu | ucccuuuu | uauaucccau uuuuauaucg | 2220 |
| aucucuuauu | uuacaauaaa | acuuugcugc | caccugugug | ucugagggggu g | 2271 |

<210> SEQ ID NO 6
<211> LENGTH: 2404
<212> TYPE: RNA
<213> ORGANISM: Homo_Sapiens

<400> SEQUENCE: 6

| | | | | |
|---|---|---|---|---|
| ugaggccagg | agauggaggc | ugcagugagc | ugugaucaca | ccacugugcu ccagccugag | 60 |
| ugacagagca | agacccuauc | ucaaaaaaaa | aaaaaaaaaa | gaaaagcucc ugagguguag | 120 |
| acgccaacuc | ucucuagcuc | gcuagugggu | ugcaggaggu | gcuacgcau guugguuucu | 180 |
| uugcugccgu | cuuccaguug | cuuuaucugu | ucacuugugc | ccugacuuuc aacucugucu | 240 |
| ccuuccucuu | ccuacaguac | uccccugccc | ucaacaagau | guuuugccaa cuggccaaga | 300 |
| ccugcccugu | gcagcugugg | guugauucca | caccccgcc | cggcacccgc gucccgcgcca | 360 |
| uggccaucua | caagcaguca | cagcacauga | cggagguugu | gaggcgcugc ccccaccaug | 420 |
| agcgcugcuc | agauagcgau | ggucuggccc | cucucagca | ucuuauccga guggaaggaa | 480 |
| auuugcgugu | ggaguauuug | gaugacagaa | acacuuuucg | acauagugug guggugcccu | 540 |
| augagccgcc | ugagguuggc | ucugacugua | ccaccaucca | cuacaacuac auguguaaca | 600 |
| guccugcau | gggcggcaug | aaccggaggc | ccauccucac | caucaucaca cuggaagacu | 660 |
| ccaguggguaa | ucuacuggga | cggaacagcu | uugaggugcg | uguuugugcc uguccuggga | 720 |
| gagaccggcg | cacagaggaa | gagaaucucc | gcaagaaagg | ggagccucac cacgagcugc | 780 |
| ccccagggag | cacuaagcga | gcacugccca | acaacaccag | cuccucuccc cagccaaaga | 840 |

| | |
|---|---|
| agaaaccacu ggauggagaa uauuucaccc uucaggacca gaccagcuuu caaaaagaaa | 900 |
| auuguuaaag agagcaugaa aaugguucua ugacuuugcc ugauacagau gcuacuugac | 960 |
| uuacgauggu guuacuuccu gauaaacucg ucguaaguug aaaauauuau ccgugggcgu | 1020 |
| gagcgcuucg agauguuccg agagcugaau gaggccuugg aacucaagga ugcccaggcu | 1080 |
| gggaaggagc cagggggggag cagggcucac uccagccacc ugaaguccaa aaagggucag | 1140 |
| ucuaccuccc gccauaaaaa acucauguuc aagacagaag gccugacuc agacugacau | 1200 |
| ucuccacuuc uuguucccca cugacagccu cccaccccca ucucucccuc cccugccauu | 1260 |
| uugggguuuug ggucuuugaa cccuugcuug caauaggugu gcgucagaag cacccaggac | 1320 |
| uuccauuugc uuugucccgg ggcuccacug aacaaguugg ccugcacugg guuuuguug | 1380 |
| ugggaggag gaugggagu aggacauacc agcuuagauu uuaagguuuu uacgugagg | 1440 |
| gauguuuggg agauguaaga aauguucuug caguuaaggg uuaguuuaca aucagccaca | 1500 |
| uucuagguag gggcccacuu caccguacua accaggaag cugucccuca cuguugaauu | 1560 |
| uucucuaacu ucaaggccca uaucugugaa augcuggcau uugcaccuac cucacagagu | 1620 |
| gcauugugag gguuaaugaa auaauguaca ucuggccuug aaaccaccuu uuauuacaug | 1680 |
| gggucuagaa cuugaccccc uugagggugc uuguccccuc ucccguuugg ucggugggu | 1740 |
| gguaguuucu acaguugggc agcugguuag guagagggag uugucaaguc ucugcuggcc | 1800 |
| cagccaaacc cugucugaca acccucuuggu gaaccuuagu accuaaaagg aaaucucacc | 1860 |
| ccaucccaca cccuggagga uuucaucucu uguauaugau gaucuggauc caccaagacu | 1920 |
| uguuuuaugc ucagggucaa uuucuuuuu cuuuuuuuu uuuuuuuuc uuuuucuuug | 1980 |
| agacuggguc ucgcuuuguu gcccaggcug gaguggagug gcgugaucuu ggcuuacugc | 2040 |
| agccuuugcc uccccggcuc gagcagguccu gccucagccu ccggaguagc ugggaccaca | 2100 |
| gguucaugcc accauggcca gccaacuuuu gcauguuuug uagagauggg gucucacagu | 2160 |
| guugcccagg cuggucucaa acuccugggc ucaggcgauc caccgucuc agccuccag | 2220 |
| agugcuggga uuacaauugu gagccaccac guccagcugg aagggucaac aucuuuuaca | 2280 |
| uucugcaagc acaucugcau uuucacccca cccuucccu ccuucccccu uuuuauaucc | 2340 |
| cauuuuuaua ucgaucucuu auuuuacaau aaaacuuugc ugccaccugu gugucugagg | 2400 |
| ggug | 2404 |

<210> SEQ ID NO 7
<211> LENGTH: 2331
<212> TYPE: RNA
<213> ORGANISM: Homo_Sapiens

<400> SEQUENCE: 7

| | |
|---|---|
| ugaggccagg agauggaggc ugcagugagc ugugaucaca ccacugugcu ccagccugag | 60 |
| ugacagagca agacccuauc ucaaaaaaaa aaaaaaaaa gaaaagcucc ugagguguag | 120 |
| acgccaacuc ucucuagcuc gcuagugggu ugcaggaggu gcuuacgcau guuuguuucu | 180 |
| uugcugccgu cuuccaguug cuuuaucugu ucacuugugc ccugacuuuc aacucugucu | 240 |
| ccuuccucuu ccuacaguac uccccugccc ucaacaagau guuugccaa cuggccaaga | 300 |
| ccugcccugu gcagcugugg guugauucca cacccccgcc cggcacccgc guccgcgcca | 360 |
| uggccaucua caagcaguca cagcacauga cggagguugu gaggcgcugc ccccaccaug | 420 |
| agcgcugcuc agauagcgau ggucuggccc cucucagca ucuuauccga guggaaggaa | 480 |
| auuugcgugu ggaguauuug gaugacagaa acacuuuucg acauagugug guggugcccu | 540 |

```
augagccgcc ugagguuggc ucugacugua ccaccaucca cuacaacuac auguguaaca      600
guuccugcau gggcggcaug aaccggaggc ccauccucac caucaucaca cuggaagacu      660
ccagugguaa ucuacuggga cggaacagcu uugaggugcg uguuugugcc uguccuggga      720
gagaccggcg cacagaggaa gagaaucucc gcaagaaagg ggagccucac cacgagcugc      780
ccccagggag cacuaagcga gcacugccca acaaccag cuccucuccc cagccaaaga       840
agaaaccacu ggauggagaa uauuucaccc uucagaugcu acugacuua cgauggyguu      900 acuccugau aaacucgucg uaaguugaaa auauuauccg ugggcgugag cgcuucgaga       960
uguuccgaga gcugaaugag gccuuggaac ucaaggaugc ccaggcuggg aaggagccag     1020
gggggagcag ggcucacucc agccaccuga aguccaaaaa gggucagucu accucccgcc     1080 auaaaaacu cauguucaag acagaagggc cugacucaga cugacauucu ccacuucuug      1140
uuccccacug acagccuccc accccaucu cucccucccc ugccauuuug gguuugggu       1200 cuuugaaccc uugcuugcaa uaggugugcg ucagaagcac ccaggacuuc cauucgcuuu     1260
gucccggggc uccacugaac aaguuggccu gcacuggugu uuuguugugg ggaggaggau     1320
gggagugagg acauaccagc uuagauuuua agguuuuuac ugagggggau guuugggaga     1380
uguaagaaau guucuugcag uuaagggua guuuacaauc agccacauuc uagguagggg      1440
cccacuucac cguacuaacc agggaagcug ucccucacug uugaauuuuc ucuaacuuca     1500
aggcccauau cugugaaaug cuggcauuug caccuaccuc acagagugca uugugagggu     1560
uaaugaaaua auguacaucu ggccuugaaa ccaccuuuua uuacauggg ucuagaacuu      1620 gaccccuug agggugcuug uucccucucc cguuggucg ggguuggu aguucuaca          1680 guugggcagc ugguuaggua gagggaguug ucaagucucu gcuggcccag ccaaacccug     1740
ucugacaacc ucuggugaa ccuuaguacc uaaaaggaaa ucuccccca ucccacaccc       1800 uggaggauuu caucucuugu auaugaugau cuggauccac caagacuugu uuuaugcuca     1860
gggucaauuu cuuuuucuu uuuuuuuuu uuuuuucuuu uucuuugaga cugggucucg       1920
cuuuguugcc caggcuggag uggagugcg ugaucuuggc uuacgcagc cuuugccucc       1980 ccggcucgag caguccugcc ucagccuccg gaguagcugg gaccacaggu ucaugccacc     2040 augccagcc aacuuuugca uguuuuguag agauggggguc ucacaguguu gcccaggcug     2100
gucucaaacu ccugggcuca ggcgauccac cugucucagc cucccagagu gcuggagaua     2160
caauugugag ccaccacguc cagcuggaag ggucaacauc uuuuacauuc ugcaagcaca     2220
ucugcauuuu caccccaccc uuccccuccu cucccuuuu auaucccau uuuuauaucg       2280 aucucuuauu uuacaauaaa acuuugcugc caccugugug ucugagggu g              2331
```

<210> SEQ ID NO 8
<211> LENGTH: 19
<212> TYPE: RNA
<213> ORGANISM: artificial
<220> FEATURE:
<223> OTHER INFORMATION: Chemically Synthesized

<400> SEQUENCE: 8
cagaccuaug gaaacuacu                                                   19

<210> SEQ ID NO 9
<211> LENGTH: 19
<212> TYPE: RNA
<213> ORGANISM: artificial
<220> FEATURE:

<223> OTHER INFORMATION: Chemically Synthesized

<400> SEQUENCE: 9
ggauguuugg gagauguaa                                                    19

<210> SEQ ID NO 10
<211> LENGTH: 19
<212> TYPE: RNA
<213> ORGANISM: artificial
<220> FEATURE:
<223> OTHER INFORMATION: Chemically Synthesized

<400> SEQUENCE: 10
gacucagacu gacauucua                                                    19

<210> SEQ ID NO 11
<211> LENGTH: 19
<212> TYPE: RNA
<213> ORGANISM: artificial
<220> FEATURE:
<223> OTHER INFORMATION: Chemically Synthesized

<400> SEQUENCE: 11
ggguugguag uuucuacaa                                                    19

<210> SEQ ID NO 12
<211> LENGTH: 19
<212> TYPE: RNA
<213> ORGANISM: artificial
<220> FEATURE:
<223> OTHER INFORMATION: Chemically Synthesized

<400> SEQUENCE: 12
gggauguuug ggagaugua                                                    19

<210> SEQ ID NO 13
<211> LENGTH: 19
<212> TYPE: RNA
<213> ORGANISM: artificial
<220> FEATURE:
<223> OTHER INFORMATION: Chemically Synthesized

<400> SEQUENCE: 13
ggauccacca agacuugua                                                    19

<210> SEQ ID NO 14
<211> LENGTH: 19
<212> TYPE: RNA
<213> ORGANISM: artificial
<220> FEATURE:
<223> OTHER INFORMATION: Chemically Synthesized

<400> SEQUENCE: 14
gagggauguu ugggagaua                                                    19

<210> SEQ ID NO 15
<211> LENGTH: 19
<212> TYPE: RNA
<213> ORGANISM: artificial
<220> FEATURE:
<223> OTHER INFORMATION: Chemically Synthesized

<400> SEQUENCE: 15
gggccugacu cagacugaa                                                    19

```
<210> SEQ ID NO 16
<211> LENGTH: 19
<212> TYPE: RNA
<213> ORGANISM: artificial
<220> FEATURE:
<223> OTHER INFORMATION: Chemically Synthesized

<400> SEQUENCE: 16
gacucagacu gacauucuu                                              19

<210> SEQ ID NO 17
<211> LENGTH: 19
<212> TYPE: RNA
<213> ORGANISM: artificial
<220> FEATURE:
<223> OTHER INFORMATION: Chemically Synthesized

<400> SEQUENCE: 17
gcauuugcac cuaccucaa                                              19

<210> SEQ ID NO 18
<211> LENGTH: 19
<212> TYPE: RNA
<213> ORGANISM: artificial
<220> FEATURE:
<223> OTHER INFORMATION: Chemically Synthesized

<400> SEQUENCE: 18
ggauguuugg gagauguau                                              19

<210> SEQ ID NO 19
<211> LENGTH: 19
<212> TYPE: RNA
<213> ORGANISM: artificial
<220> FEATURE:
<223> OTHER INFORMATION: Chemically Synthesized

<400> SEQUENCE: 19
gggccugacu cagacugau                                              19

<210> SEQ ID NO 20
<211> LENGTH: 19
<212> TYPE: RNA
<213> ORGANISM: artificial
<220> FEATURE:
<223> OTHER INFORMATION: Chemically Synthesized

<400> SEQUENCE: 20
cagaccuaug gaaacuaca                                              19

<210> SEQ ID NO 21
<211> LENGTH: 19
<212> TYPE: RNA
<213> ORGANISM: artificial
<220> FEATURE:
<223> OTHER INFORMATION: Chemically Synthesized

<400> SEQUENCE: 21
aguaguuucc auaggucug                                              19

<210> SEQ ID NO 22
<211> LENGTH: 19
<212> TYPE: RNA
<213> ORGANISM: artificial
<220> FEATURE:
<223> OTHER INFORMATION: Chemically Synthesized
```

```
<400> SEQUENCE: 22
uuacaucucc caaacaucc                                                    19

<210> SEQ ID NO 23
<211> LENGTH: 19
<212> TYPE: RNA
<213> ORGANISM: artificial
<220> FEATURE:
<223> OTHER INFORMATION: Chemically Synthesized

<400> SEQUENCE: 23
uagaauguca gucugaguc                                                    19

<210> SEQ ID NO 24
<211> LENGTH: 19
<212> TYPE: RNA
<213> ORGANISM: artificial
<220> FEATURE:
<223> OTHER INFORMATION: Chemically Synthesized

<400> SEQUENCE: 24
uuguagaaac uaccaaccc                                                    19

<210> SEQ ID NO 25
<211> LENGTH: 19
<212> TYPE: RNA
<213> ORGANISM: artificial
<220> FEATURE:
<223> OTHER INFORMATION: Chemically Synthesized

<400> SEQUENCE: 25
uacaucuccc aaacauccc                                                    19

<210> SEQ ID NO 26
<211> LENGTH: 19
<212> TYPE: RNA
<213> ORGANISM: artificial
<220> FEATURE:
<223> OTHER INFORMATION: Chemically Synthesized

<400> SEQUENCE: 26
uacaagucuu gguggaucc                                                    19

<210> SEQ ID NO 27
<211> LENGTH: 19
<212> TYPE: RNA
<213> ORGANISM: artificial
<220> FEATURE:
<223> OTHER INFORMATION: Chemically Synthesized

<400> SEQUENCE: 27
uaucucccaa acaucccuc                                                    19

<210> SEQ ID NO 28
<211> LENGTH: 19
<212> TYPE: RNA
<213> ORGANISM: artificial
<220> FEATURE:
<223> OTHER INFORMATION: Chemically Synthesized

<400> SEQUENCE: 28
uucagucuga gucaggccc                                                    19

<210> SEQ ID NO 29
<211> LENGTH: 19
```

```
<212> TYPE: RNA
<213> ORGANISM: artificial
<220> FEATURE:
<223> OTHER INFORMATION: Chemically Synthesized

<400> SEQUENCE: 29
aagaauguca gucugaguc                                                  19

<210> SEQ ID NO 30
<211> LENGTH: 19
<212> TYPE: RNA
<213> ORGANISM: artificial
<220> FEATURE:
<223> OTHER INFORMATION: Chemically Synthesized

<400> SEQUENCE: 30
uugagguagg ugcaaaugc                                                  19

<210> SEQ ID NO 31
<211> LENGTH: 19
<212> TYPE: RNA
<213> ORGANISM: artificial
<220> FEATURE:
<223> OTHER INFORMATION: Chemically Synthesized

<400> SEQUENCE: 31
auacaucucc caaacaucc                                                  19

<210> SEQ ID NO 32
<211> LENGTH: 19
<212> TYPE: RNA
<213> ORGANISM: artificial
<220> FEATURE:
<223> OTHER INFORMATION: Chemically Synthesized

<400> SEQUENCE: 32
aucagucuga gucaggccc                                                  19

<210> SEQ ID NO 33
<211> LENGTH: 19
<212> TYPE: RNA
<213> ORGANISM: Artificial Sequence
<220> FEATURE:
<223> OTHER INFORMATION: Chemically Synthesized

<400> SEQUENCE: 33
uguaguuucc auaggucug                                                  19

<210> SEQ ID NO 34
<211> LENGTH: 19
<212> TYPE: RNA
<213> ORGANISM: artificial
<220> FEATURE:
<223> OTHER INFORMATION: Chemically synthesized

<400> SEQUENCE: 34
ccgaguggaa ggaaauuug                                                  19

<210> SEQ ID NO 35
<211> LENGTH: 19
<212> TYPE: RNA
<213> ORGANISM: artificial
<220> FEATURE:
<223> OTHER INFORMATION: Chemically synthesized

<400> SEQUENCE: 35
```

```
caaauuuccu uccacucgg                                                    19

<210> SEQ ID NO 36
<211> LENGTH: 19
<212> TYPE: RNA
<213> ORGANISM: artificial
<220> FEATURE:
<223> OTHER INFORMATION: Chemically synthesized

<400> SEQUENCE: 36
gagaauauuu cacccuuca                                                    19

<210> SEQ ID NO 37
<211> LENGTH: 19
<212> TYPE: RNA
<213> ORGANISM: Artificial Sequence
<220> FEATURE:
<223> OTHER INFORMATION: Chemically synthesized

<400> SEQUENCE: 37
ugaaggguga aauauucuc                                                    19
```